US009771380B2

(12) United States Patent
Hutchison et al.

(10) Patent No.: US 9,771,380 B2
(45) Date of Patent: Sep. 26, 2017

(54) GOLD NANOPARTICLES AND METHODS OF MAKING AND USING GOLD NANOPARTICLES

(71) Applicant: University of Oregon, Eugene, OR (US)

(72) Inventors: James E. Hutchison, Eugene, OR (US); Edward W. Elliott, III, Eugene, OR (US); Zachary Kennedy, Eugene, OR (US); Patrick Haben, Eugene, OR (US)

(73) Assignee: University of Oregon, Eugene, OR (US)

( * ) Notice: Subject to any disclaimer, the term of this patent is extended or adjusted under 35 U.S.C. 154(b) by 0 days.

(21) Appl. No.: 14/634,676

(22) Filed: Feb. 27, 2015

(65) Prior Publication Data

US 2015/0353580 A1   Dec. 10, 2015

Related U.S. Application Data

(60) Provisional application No. 62/009,897, filed on Jun. 9, 2014.

(51) Int. Cl.
| | |
|---|---|
| *G01N 21/00* | (2006.01) |
| *C07F 1/00* | (2006.01) |
| *G01N 33/543* | (2006.01) |
| *G01N 33/551* | (2006.01) |
| *G01N 33/58* | (2006.01) |
| *G01N 23/201* | (2006.01) |
| *G01N 15/02* | (2006.01) |
| *C07F 5/00* | (2006.01) |

(52) U.S. Cl.
CPC ............ *C07F 1/005* (2013.01); *C07F 5/003* (2013.01); *G01N 15/0227* (2013.01); *G01N 23/201* (2013.01); *G01N 33/54346* (2013.01); *G01N 33/54353* (2013.01); *G01N 33/551* (2013.01); *G01N 33/587* (2013.01)

(58) Field of Classification Search
None
See application file for complete search history.

(56) References Cited

U.S. PATENT DOCUMENTS

2013/0066115 A1* 3/2013 Emonds ............... B01J 19/0093
568/6

OTHER PUBLICATIONS

Burghelea, T. et al. Chaotic flow and efficient mixing in a microchannel with a polymer solution, 2004, Physicl Review E vol. 69, pp. 0663305.*

(Continued)

*Primary Examiner* — Robert Xu
(74) *Attorney, Agent, or Firm* — Klarquist Sparkman, LLP

(57) ABSTRACT

Disclosed herein are embodiments of gold nanoparticles and methods of making and using the gold nanoparticles. The disclosed gold nanoparticles have core sizes and polydispersities controlled by the methods of making the gold nanoparticles. In some embodiments, the methods of making the gold nanoparticles can concern using flow reactors and reaction conditions controlled to make gold nanoparticles having a desired core size. The gold nanoparticles disclosed herein also comprise various ligands that can be used to facilitate the use of the gold nanoparticles in a variety of applications.

18 Claims, 39 Drawing Sheets
(35 of 39 Drawing Sheet(s) Filed in Color)

(56) References Cited

OTHER PUBLICATIONS

McKenzie, L.C., et al. Determining Nanoparticle Size in Real Time by Small-Angle X-ray Scattering in a Microscale Flow System, 2010, Journal of Physical Chemistry, vol. 114, pp. 22055-22063.*

Elliott et al. "Direct Synthesis of "click-able" mixed ligand gold nanoparticles with controlled reactive group densities," Poster, Mar. 2013.

Baranov et al., "Synthesis and characterization of azidoalkyl-functionalized gold nanoparticles as scaffolds for "click"-chemistry derivatization," *J. Mater. Chem.* 21:6152-6157, Mar. 2011.

Boisselier et al., "How to very efficiently functionalize gold nanoparticles by "click" chemistry," *Chem. Commun.* 44:5788-5790, Oct. 2008.

Brennan et al., "Bionanoconjugation via Click Chemistry: The Creation of Functional Hybrids of Lipases and Gold Nanoparticles," *Bioconjugate Chem.* 17:1373-1375, Sep. 2006.

Gobbo et al., "Facile synthesis of gold nanoparticle (AuNP)-carbon nanotube (CNT) hybrids through an interfacial Michael addition reaction," *Chem. Commun.* 49:2831-2833, Feb. 2013.

Gobbo et al., "Interfacial strain-promoted alkyne-azide cycloaddition (I-SPAAC) for the synthesis of nanomaterial hybrids," *Chem. Commun.* 49:3982-3984, Mar. 2013.

Gobbo et al., "Versatile strained alkyne modified water-soluble AUNPs for *interfacial* strain promoted azide-alkyne cycloaddition (I-SPAAC)," *J. Mater. Chem. B* 2:1764-1769, Jan. 2014.

Ji et al., "Size Control of Gold Nanocrystals in Citrate Reduction: The Third Role of Citrate," *J. Am. Chem. Soc.* 129:13939-13948, Oct. 2007.

Wang et al., "Influence of Speciation of Aqueous $HAuCl_4$ on the Synthesis, Structure, and Property of Au Colloids," *J. Phys. Chem. C* 113:6505-6510, Mar. 2009.

Zhang et al., "Clickable Gold Nanoparticles as the Building Block of Nanobioprobes," *Langmuir* 26(12):10171-10176, May 2010.

Elliott et al. "Direct Synthesis of "click-able" mixed ligand gold nanoparticles with controlled reactive group densities," Poster, Mar. 2014.

Lohse et al. "Direct Synthesis of Large Water-Soluble Functionalized Gold Nanoparticles Using Bunte Salts as Ligand Precursors," *Langmuir*, 26 (10), 7504-7511, Feb. 2010.

* cited by examiner f1 (ppm)

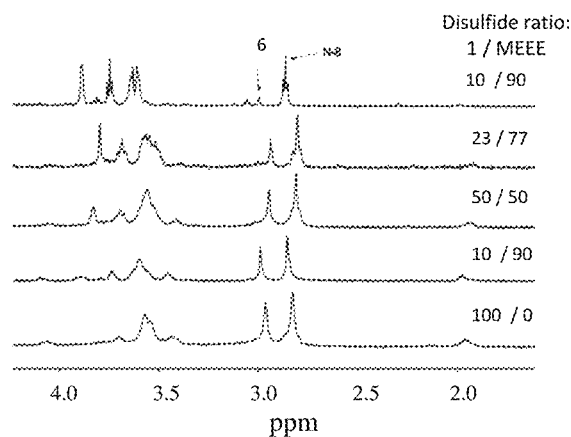
FIG. 25
FIG. 26A
FIG. 26B
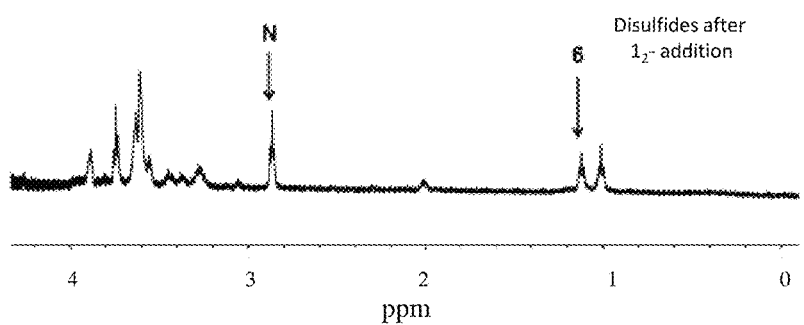

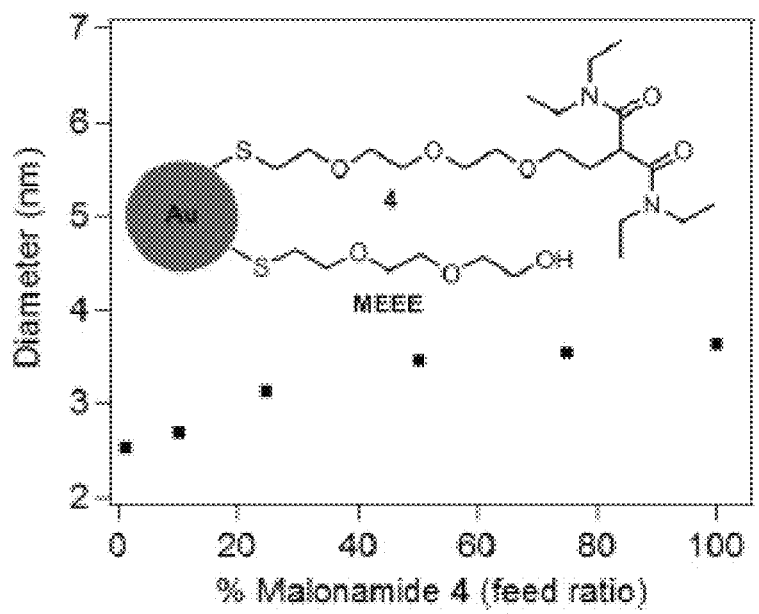
FIG. 32
FIG. 33A
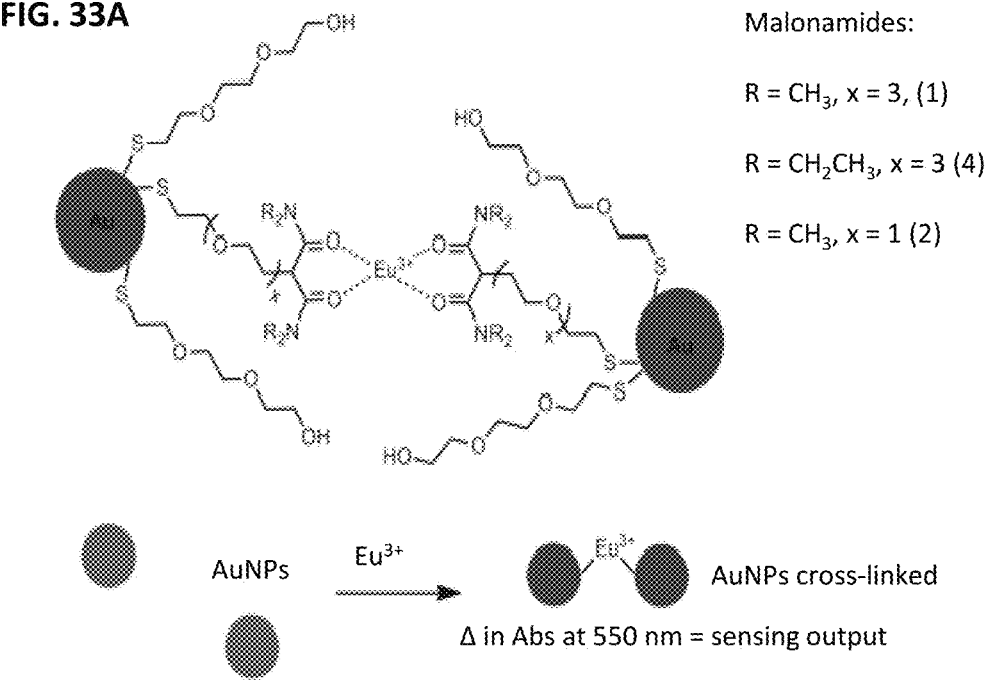
Malonamides:
R = CH$_3$, x = 3, (1)
R = CH$_2$CH$_3$, x = 3 (4)
R = CH$_3$, x = 1 (2)

GOLD NANOPARTICLES AND METHODS OF MAKING AND USING GOLD NANOPARTICLES

CROSS REFERENCE TO RELATED APPLICATION

This application claims the benefit of U.S. Provisional Patent Application No. 62/009,897, filed on Jun. 9, 2014, which is incorporated herein by reference in its entirety.

ACKNOWLEDGMENT OF GOVERNMENT SUPPORT

This invention was made with government support under Grant Numbers CHE-1102637 and PFI-BIC-1237890 awarded by the National Science Foundation, and FA8650-05-1-5041 awarded by the Air Force Research Laboratory. The government has certain rights in the claimed invention.

FIELD

The present disclosure concerns gold nanoparticle embodiments, methods of making and using the gold nanoparticles, and kits comprising the gold nanoparticles.

BACKGROUND

Gold nanoparticles possess a variety of size-dependent optical phenomena that can be harnessed for applications such as the detection of analytes in solution, the construction of microscale optical devices, and biomedical assays or treatments. Effective application of those properties is realized by controlling the nanoparticle surface chemistry (functionality). The principal attribute of gold nanoparticles harnessed in these applications is the surface plasmon resonance (SPR) phenomenon that manifests itself as an intense absorption at 520 nm. The intensity of this absorption and energy at which it occurs are determined by the size of the gold nanoparticle. Because gold nanoparticles possess such important size-related effects, the ability to control the size of the gold nanoparticle is an important factor of an effective nanoparticle synthesis. However, for many applications, precise size control is useless if the functionality of the particle cannot also be controlled. It is the surface chemistry of the particle that enables many of the applications detailed above.

A number of chemical strategies have been developed for synthesizing functionalized gold nanoparticles of various sizes. Yet even the most commonly used techniques (e.g., the Brust synthesis and ligand-exchange techniques) still suffer from limitations that make it a challenge to synthesize gold nanoparticles of a particular size with precisely controlled surface chemistry. In the Brust synthesis, gold nanoparticles are synthesized in the presence of functionalized thiols, producing thiolate monolayer-protected gold nanoparticles. However, because gold nanoparticle growth is quickly passivated by the formation of thiolate bonds, gold nanoparticles with core diameters greater than 4 nm cannot effectively be made in this way.

In contrast, ligand-exchange techniques require a stepwise synthesis approach that involves producing a gold nanoparticle stabilized by an exchangeable ligand (citrate, phosphines, or amines) that is replaced with a functionalized thiol in a subsequent step to yield the monolayer-protected particle. Such methods, however, cannot be used to make large AuNPs in an efficient and reproducible manner because incomplete ligand exchange becomes a problem and the reaction is sensitive to changes in ionic strength and interactions between incoming and outgoing functionalities. The differences in reaction efficiency may be related to the curvature of the particle, the reactivity of the particle surface, and other size-related changes in the surface chemistry of the particle.

Accordingly, traditional approaches to making gold nanoparticles face limits to and challenges in the ability to make functionalized gold nanoparticles having desired core sizes, and there is a significant long-felt need for the development of methods that produce specifically functionalized gold nanoparticles with tuneable core sizes.

SUMMARY

Disclosed herein are embodiments of a method for making a gold nanoparticle, comprising adding a reducing composition comprising a reducing agent into a flow reactor; adding a pre-determined amount of a ligand precursor composition comprising at least one ligand precursor having a thiosulfate terminal functional group, a polar linker, and a reactive moiety selected from polar functional group, a clickable functional group, a detectable label, or an enzyme-reactive moiety into the flow reactor; adding a gold nanoparticle precursor composition comprising a gold nanoparticle precursor into the flow reactor; and isolating a functionalized gold nanoparticle coupled to at least one ligand of the ligand precursor composition.

In some embodiments, the method further comprises adding a base to reducing composition, the gold nanoparticle precursor composition, or a combination thereof so as to change the speciation of the gold nanoparticle precursor, change the pH of the reducing composition, or a combination thereof. The base can be selected from any base capable of producing hydroxide in aqueous solutions. In some embodiments, the base can be selected from NaOH, LiOH, KOH, and combinations thereof.

In some embodiments, the reducing composition can be added to the flow reactor at a flow rate that results in turbulent mixing of the reducing composition, the ligand precursor composition, the gold nanoparticle composition, or any combination thereof.

The ligand precursor used in the disclosed methods can have a formula

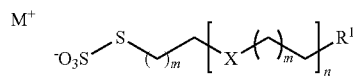

wherein each X independently is selected from oxygen or sulfur; $R^1$ is selected from —OH, —N($R^2$)$_2$, —CO$_2R^2$, —P(O)(O$R^2$)$_3$, —PO$_4^{-3}$—P(O$R^2$)$_3$, —SO$_4$, —CH(C(O)N($R^2$)$_2$)$_2$, —N$_3$, alkynyl, a fluorophore, an enzyme, a hapten, lisinopril, enalapril, captopril, ramipril, or losartan, wherein $R^2$ is selected from hydrogen, alkyl, alkenyl, alkynyl, or aryl; each m independently is 0 to 5; and n is 1 to 10.

In some embodiments, the reducing composition, the ligand precursor composition, and the gold nanoparticle precursor composition are added to the main flow channel sequentially. In some embodiments, the reducing composition is first added into the flow reactor followed by the ligand precursor composition and the gold nanoparticle precursor composition, sequentially or simultaneously. In other embodiments, the gold nanoparticle precursor composition is first added into the flow reactor followed by the ligand precursor composition and the reducing composition, sequentially or simultaneously.

In some embodiments, the gold nanoparticle precursor composition has a pH ranging from 2 to 9. In exemplary embodiments, the pH of the gold nanoparticle precursor composition is 3, 5, or 7. Some embodiments of the methods disclosed herein can make gold nanoparticles comprising a core diameter ranging from 1.5 nm to 10 nm.

In yet additional embodiments, the methods can comprise adding a first ligand precursor composition and a second ligand precursor composition simultaneously or sequentially, wherein the first ligand precursor composition comprises a first ligand precursor and the second ligand precursor composition comprises a second ligand precursor and wherein the first ligand precursor composition and the second ligand precursor composition are added at a feed ratio of first ligand precursor composition to second ligand precursor composition ranging from 80:20 to 99:1.

In some embodiments, the method further comprises reacting an isolated gold nanoparticle with a compound comprising a clickable functional group capable of reacting with the clickable functional group of the isolated gold nanoparticle.

Some embodiments of the method can further comprise using SAXS analysis to characterize gold nanoparticles prior to isolation to determine the gold nanoparticles' core size.

In exemplary embodiments of the method embodiments described above, the reducing composition can be added to the main flow channel at a total flow rate of 40 mL/minute to 80 mL/minute; the ligand precursor composition can comprise (a) a first ligand precursor composition comprising a ligand precursor having a thiosulfate terminal functional group, a polar linker, and a polar functional group and (b) a second ligand precursor composition comprising a ligand precursor having a thiosulfate terminal functional group, a polar linker, and a clickable functional group and wherein the first ligand precursor composition and the second ligand precursor composition are added at a feed ratio of first ligand precursor composition to second ligand precursor composition ranging from 80:20 to 99:1; the gold nanoparticle precursor composition can have a pH ranging from 2 to 9; and the functionalized gold nanoparticle can have a functionalization ratio of the ligand precursor of the first composition to the ligand precursor of the second composition equal to the feed ratio.

Also disclosed herein are gold nanoparticles, such as gold nanoparticles comprising a gold nanoparticle core; at least one ligand consisting of a polyethylene glycol linker and a polar terminal functional group other than a methoxy group; and at least one ligand consisting of a polyethylene glycol linker and terminal azide.

In some embodiments, the nanoparticle has a formula wherein r and s are numerical values present in a ratio ranging from 80:20 to 99:1.

Also disclosed herein are embodiments of a combination comprising a gold nanoparticle precursor composition comprising a gold nanoparticle precursor; a first ligand precursor composition comprising a first ligand precursor having a thiosulfate terminal functional group, a polyethylene linker, and clickable functional group; and a second ligand precursor composition comprising a second ligand precursor having a thiosulfate terminal functional group, a polyethylene linker, and a polar functional group. In some embodiments, the combination further comprises a composition comprising a reducing agent. In exemplary embodiments, the gold nanoparticle precursor has a formula $HAuCl_{4-x}(OH)_x$ wherein x is 0, 1, 2, 3, or 4; the first ligand precursor is a hydroxy-terminated polyethylene glycol thiosulfate ligand precursor; and the second ligand precursor is an azide-terminated polyethylene glycol thiosulfate ligand precursor.

Also disclosed herein are embodiments of a kit comprising:

a first container comprising a gold nanoparticle having a formula

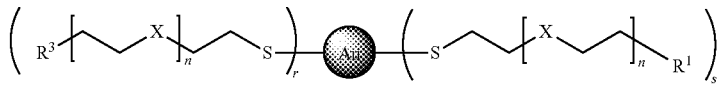

wherein
each X independently is selected from oxygen;
each of $R^1$ and $R^3$ independently is selected from —OH, —N($R^2$)$_2$, —CO$_2$R$^2$, —P(O)(OR$^2$)$_3$, —PO$_4^{-3}$—P(OR$^2$)$_3$, —SO$_4$, —CH(C(O)N($R^2$)$_2$)$_2$, —N$_3$, or alkynyl, wherein $R^2$ is selected from hydrogen, alkyl, alkenyl, alkynyl, or aryl;
each n is 1 to 10; and
r and s are numerical values present in a ratio ranging from 80:20 to 99:1; and a second container comprising a compound capable of forming a covalent bond with at least one $R^1$ or $R^3$ when $R^1$ or $R^3$ is —N$_3$, —CO$_2$R$^2$, or alkynyl.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

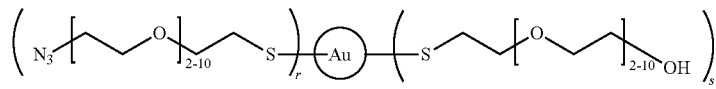

Figure 1:
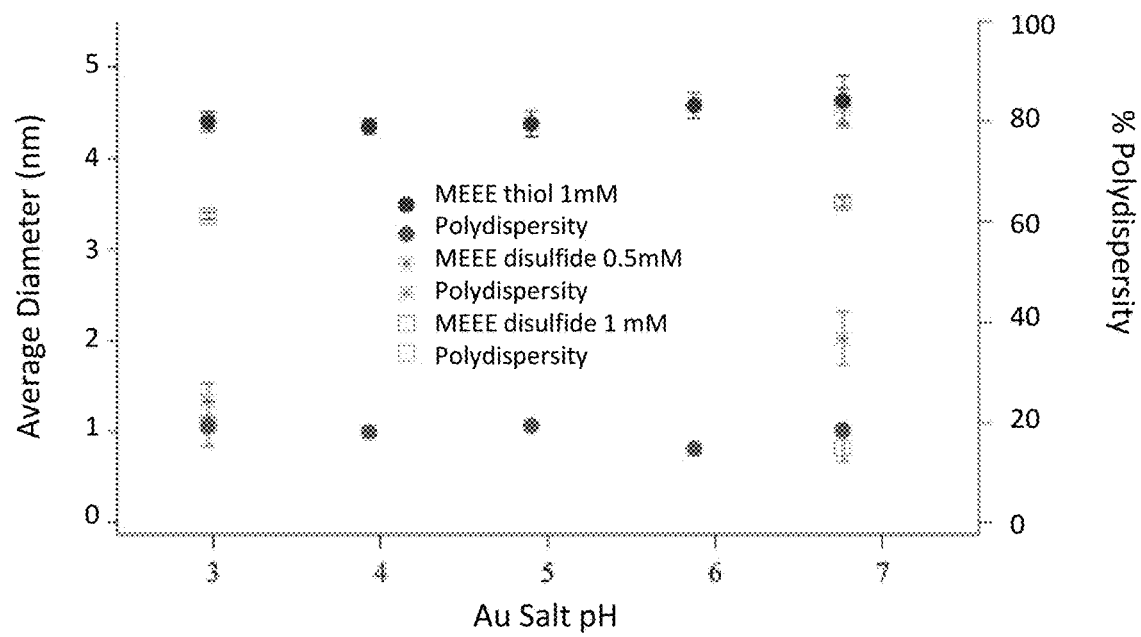
FIG. 1 is a graph illustrating average diameter (nm) and % polydispersity obtained from SAXS analysis of gold nanoparticle compounds made using thiol- or disulfide-containing ligand precursors.
Figure 2:
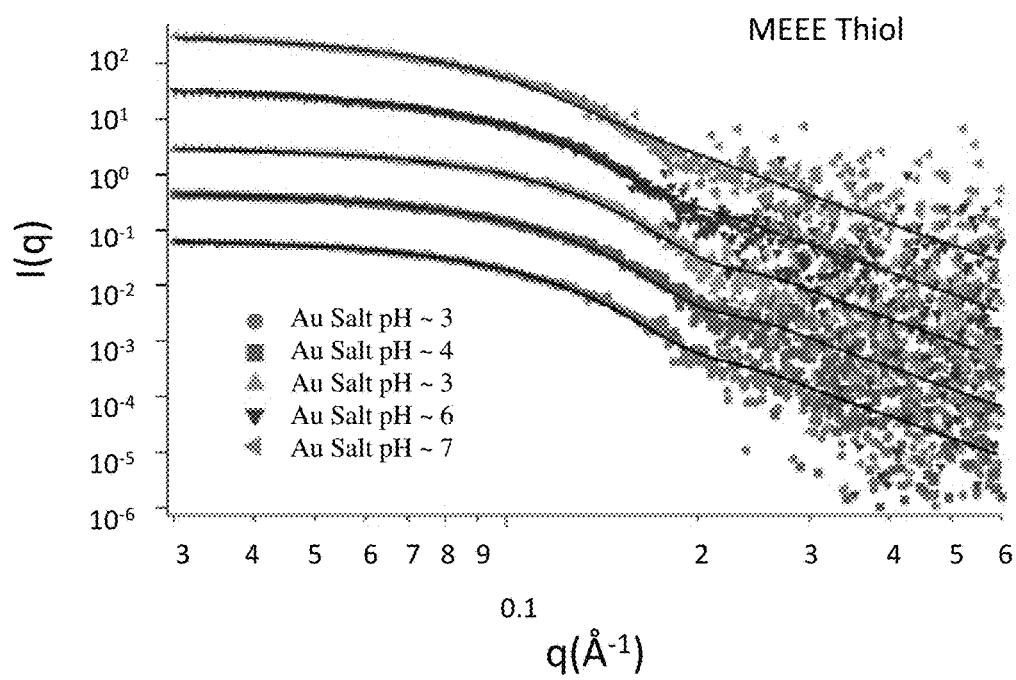
FIG. 2 is a graph illustrating SAXS data obtained from gold nanoparticles made with a thiol-containing ligand precursor across a pH range of 3 to 7, illustrating minimal nanoparticle diameter variation across the pH range.
Figure 3:
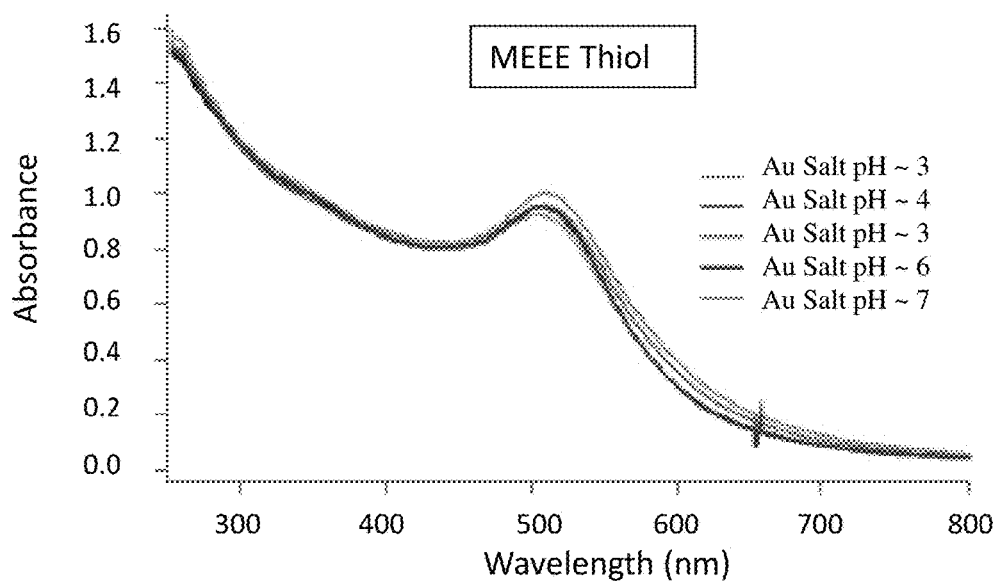
FIG. 3 is a combined UV/vis spectrum obtained from gold nanoparticles made with a thiol-containing ligand precursor across a pH range of 3 to 7, illustrating minimal nanoparticle diameter variation across the pH range.
Figure 4:
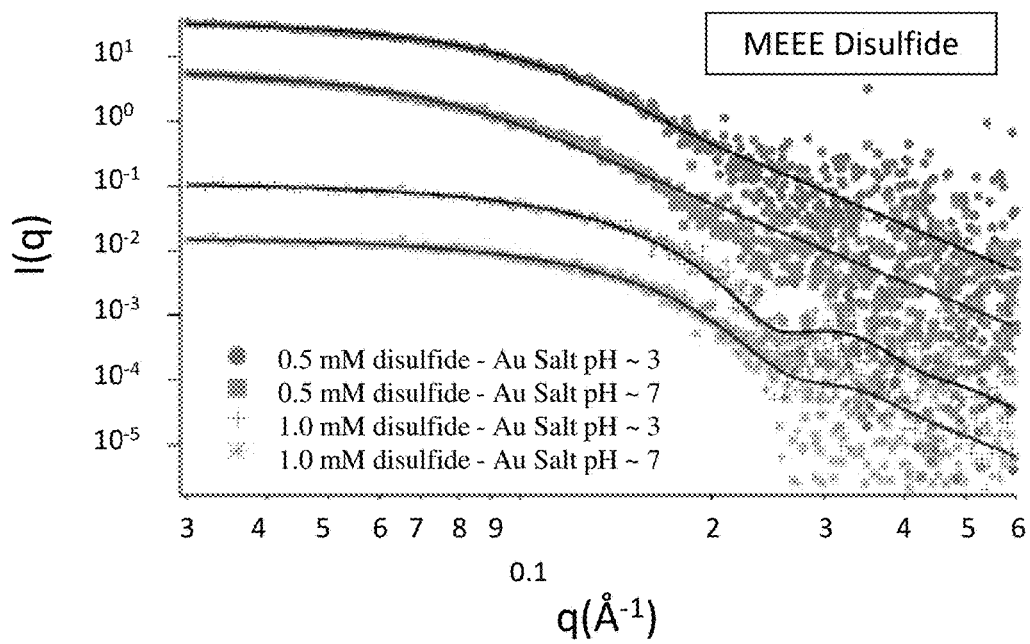

FIG. 4 is a graph illustrating SAXS data obtained from gold nanoparticles made with a disulfide-containing ligand precursor across a pH range of 3 to 7, illustrating minimal nanoparticle diameter variation across the pH range.

Figure 5:
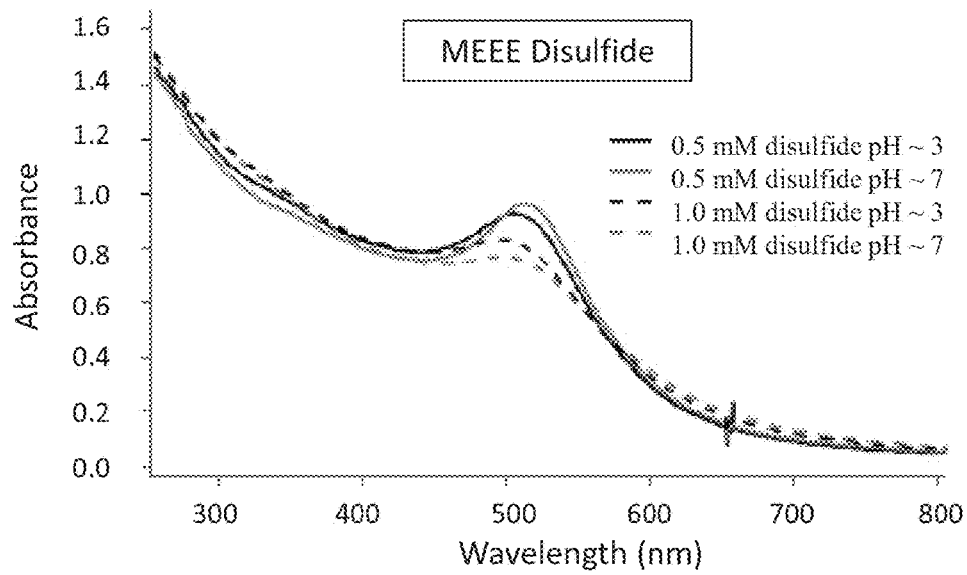

FIG. 5 is a combined UV/vis spectrum obtained from gold nanoparticles made with a disulfide-containing ligand across a pH range of 3 to 7, illustrating minimal nanoparticle diameter variation across the pH range.

Figure 6:
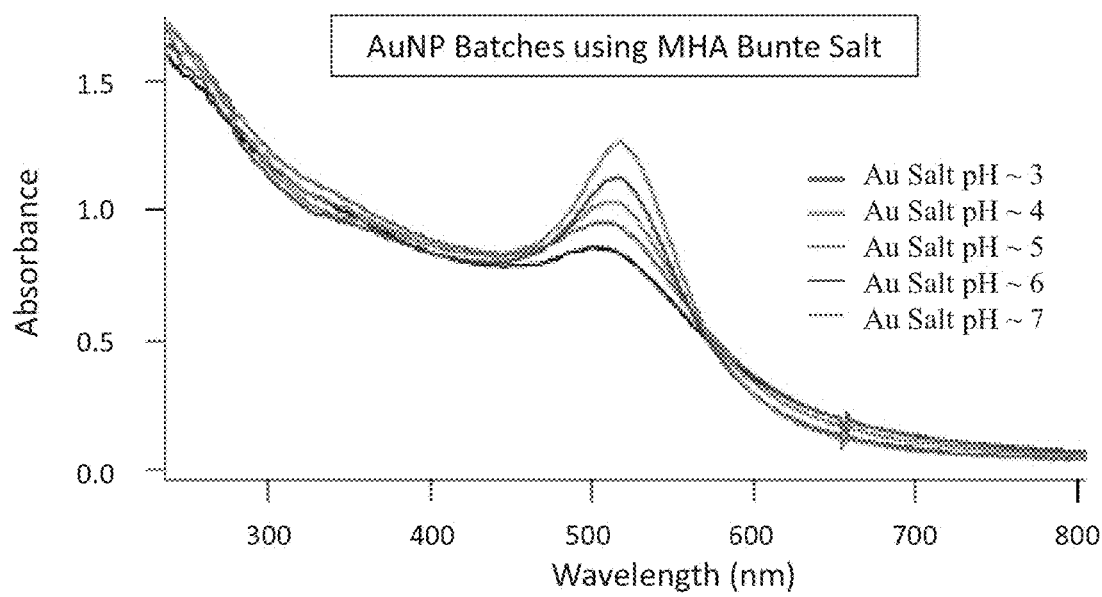

FIG. 6 is a combined UV/Vis spectrum obtained from gold nanoparticles made using novel methods disclosed herein that exhibit core diameter variation with pH modification.

Figure 7A:
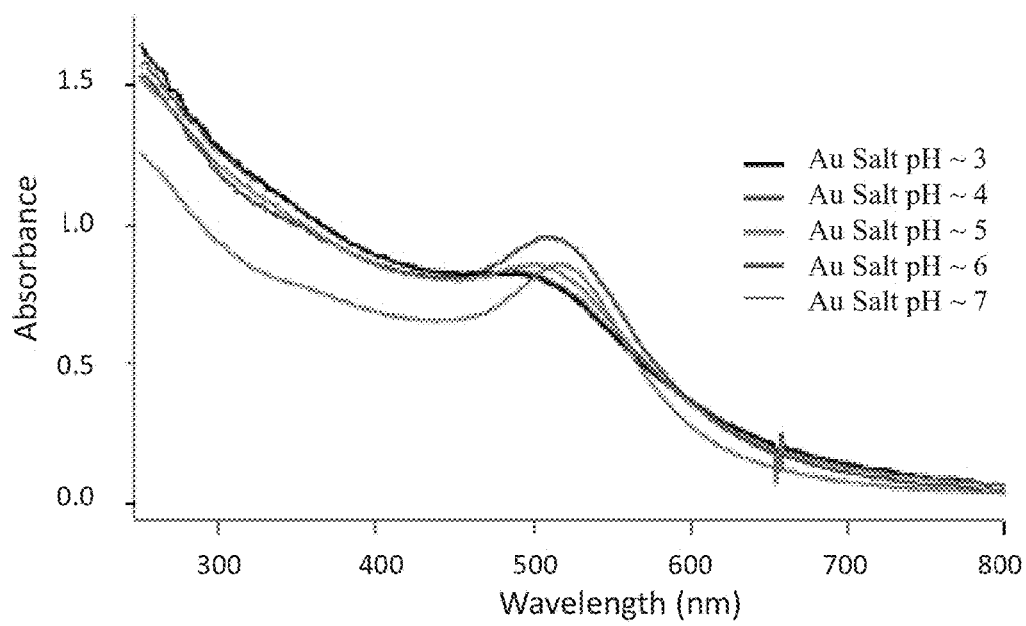
Figure 7B:
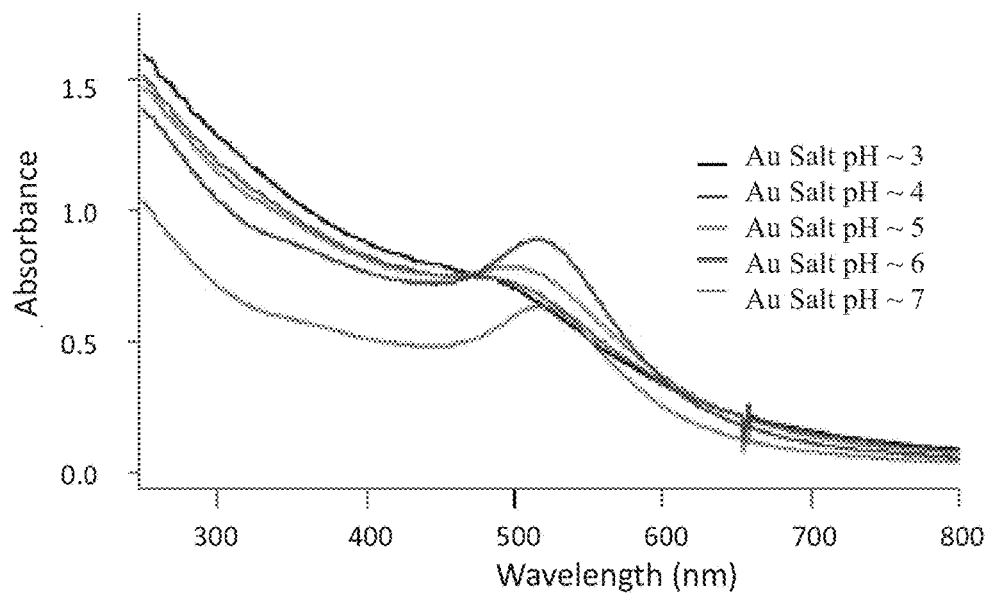
Figure 7C:
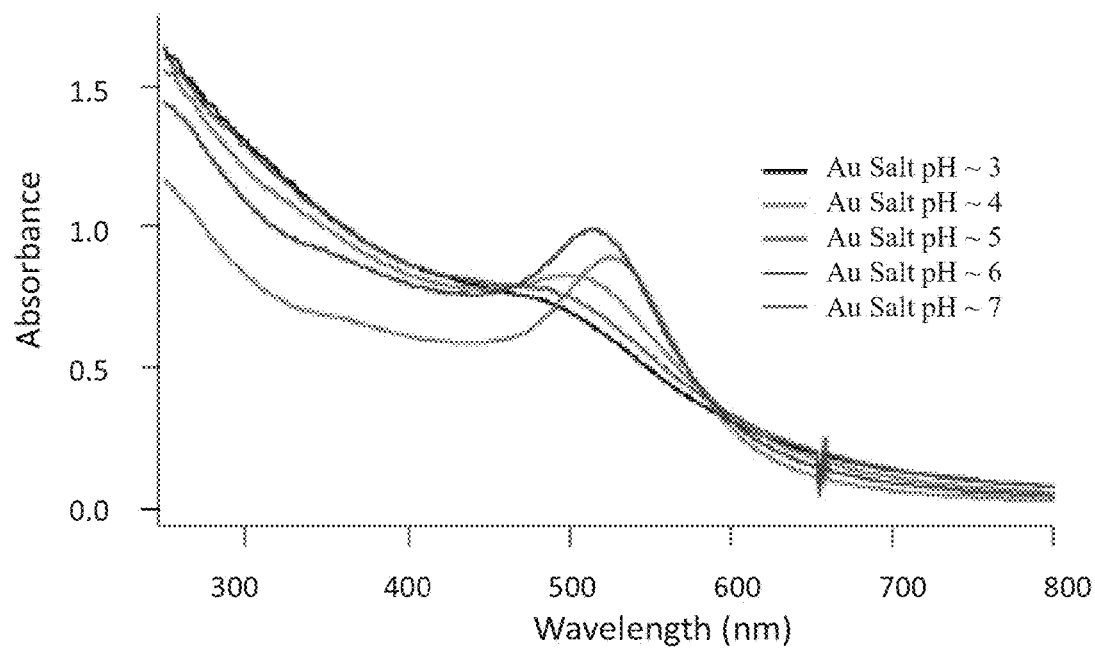

FIGS. 7A-7C are UV/vis spectrum of exemplary gold nanoparticle embodiments disclosed herein.

Figure 8:
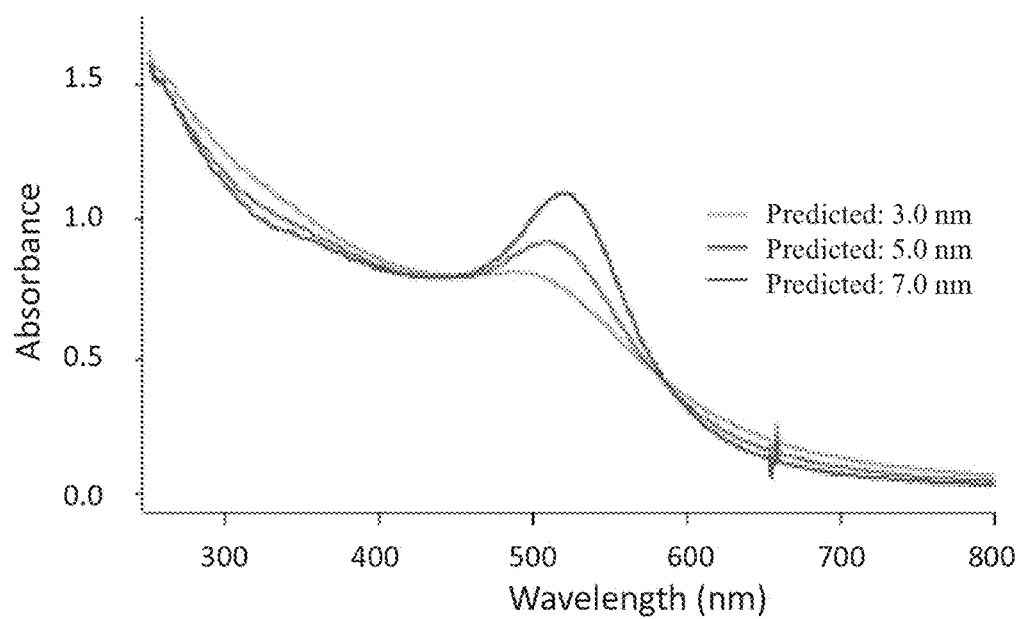

FIG. 8 is a UV/vis spectrum of exemplary gold nanoparticle embodiments made using novel methods disclosed herein and comparing the size of the gold nanoparticles made with predicted sizes.

Figure 9A:
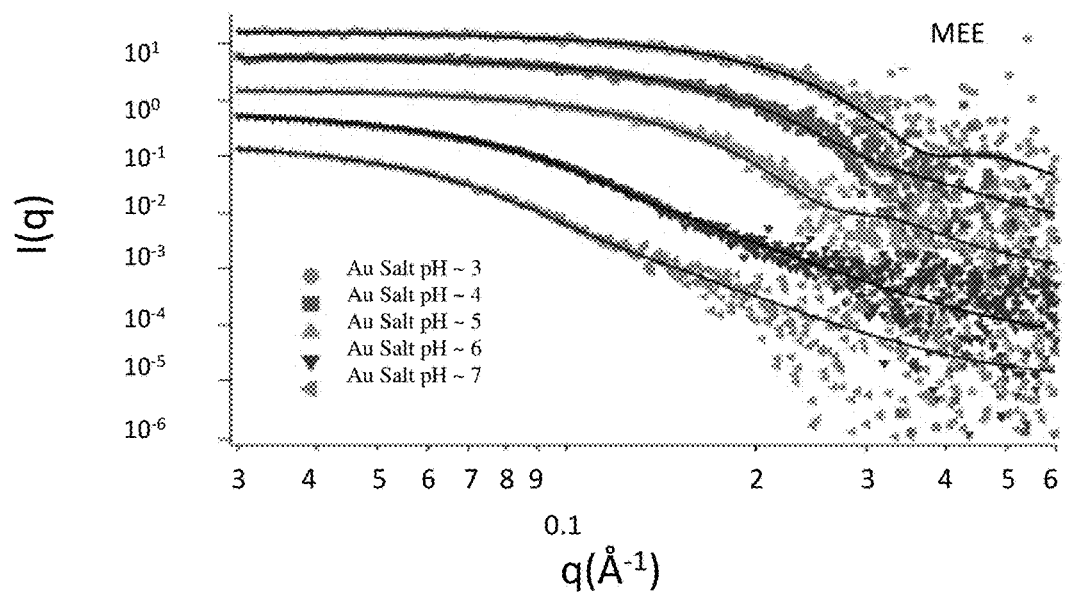
Figure 9B:
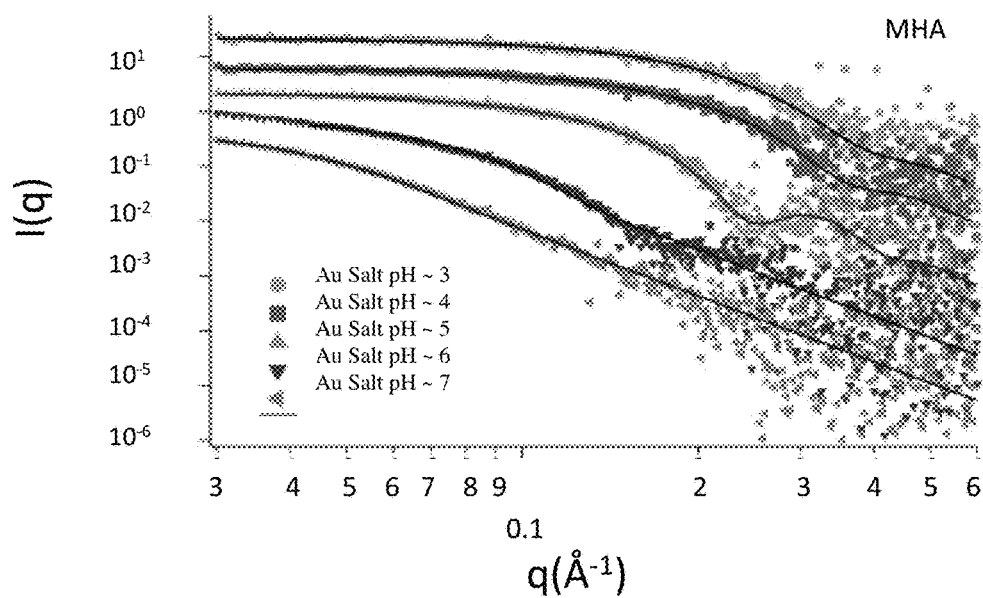
Figure 9C:
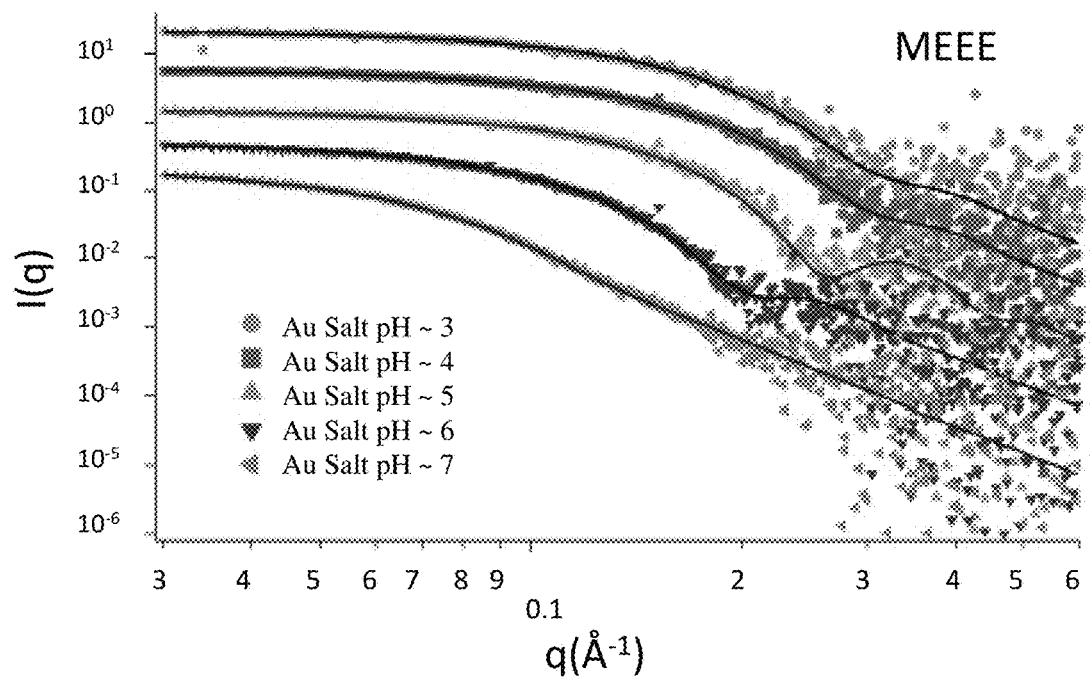

FIGS. 9A-9C are SAXS graphs illustrating SAXS patterns for each pH point of exemplary working curves disclosed herein.

Figure 10:
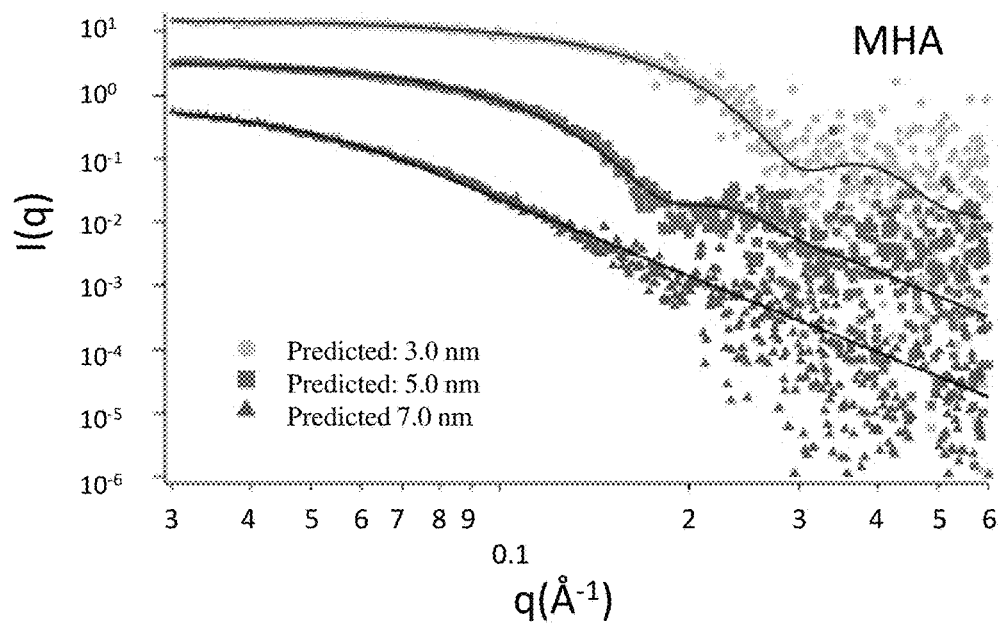

FIG. 10 is an SAXS graph illustrating predictive SAXS data for gold nanoparticles comprising an exemplary ligand disclosed herein.

Figure 11A:
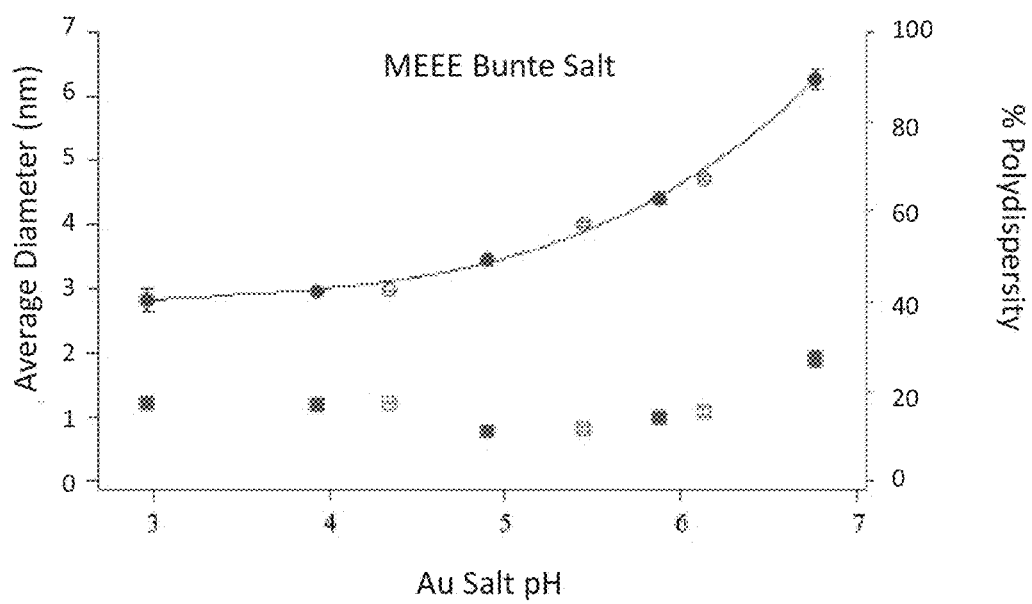
Figure 11B:
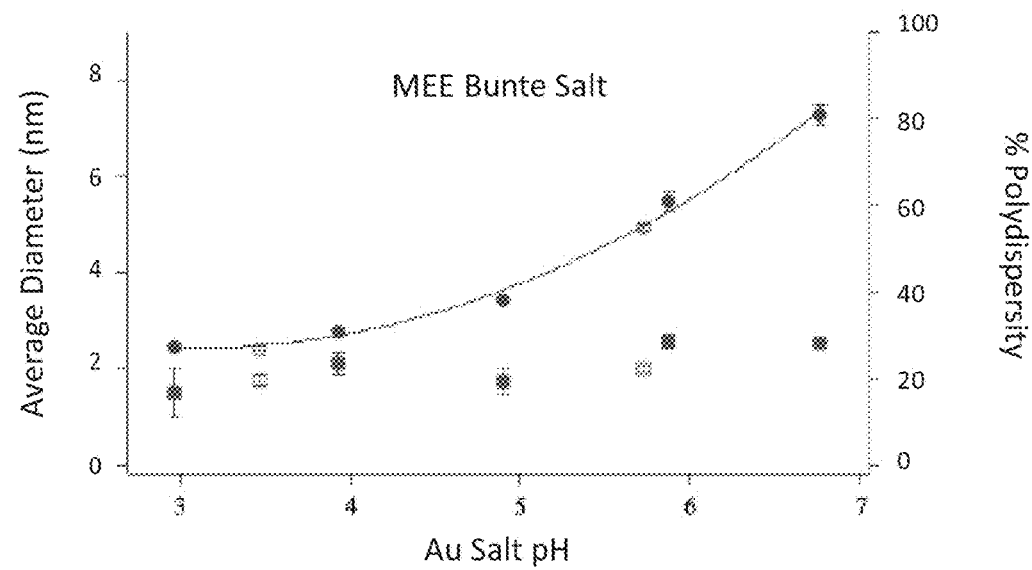
Figure 11C:
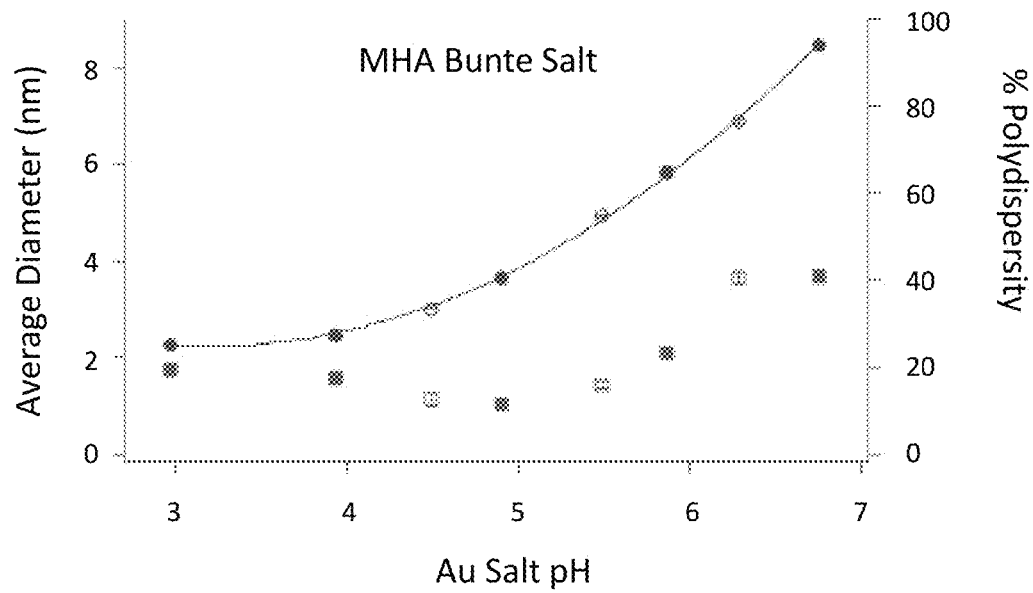

FIGS. 11A-11C are graphs illustrating average diameter (nm) and % polydispersity obtained from SAXS analysis of exemplary gold nanoparticle embodiments.

Figure 12:
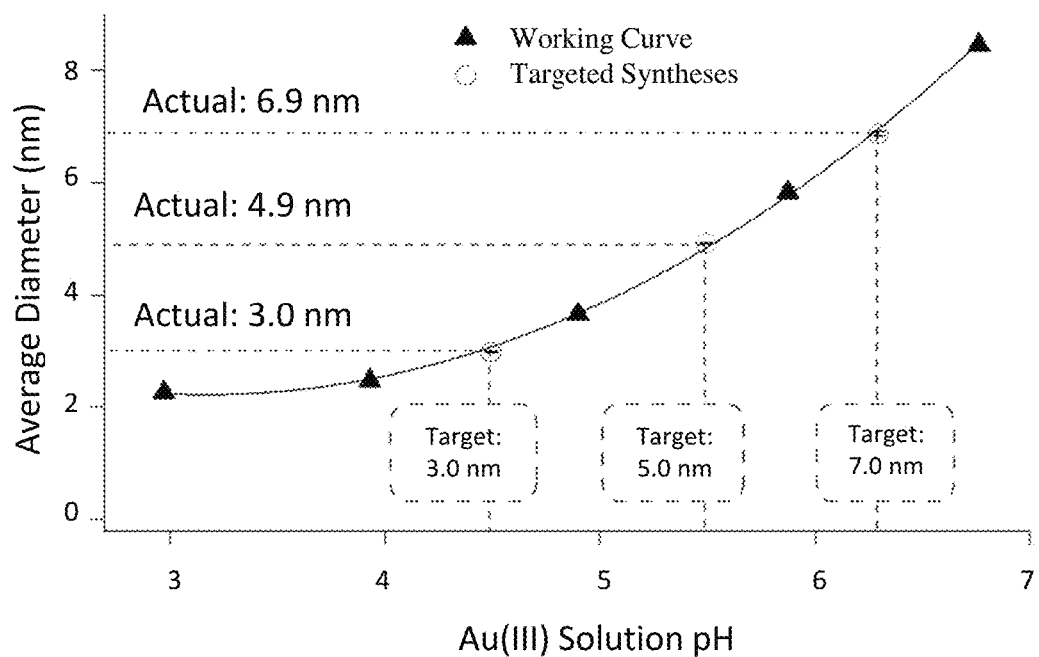

FIG. 12 is a graph of pH versus average diameter (nm) and provides a working curve that can be used determine appropriate pH values for the Au(III) solutions to obtain a particular nanoparticle diameter.

Figure 13:
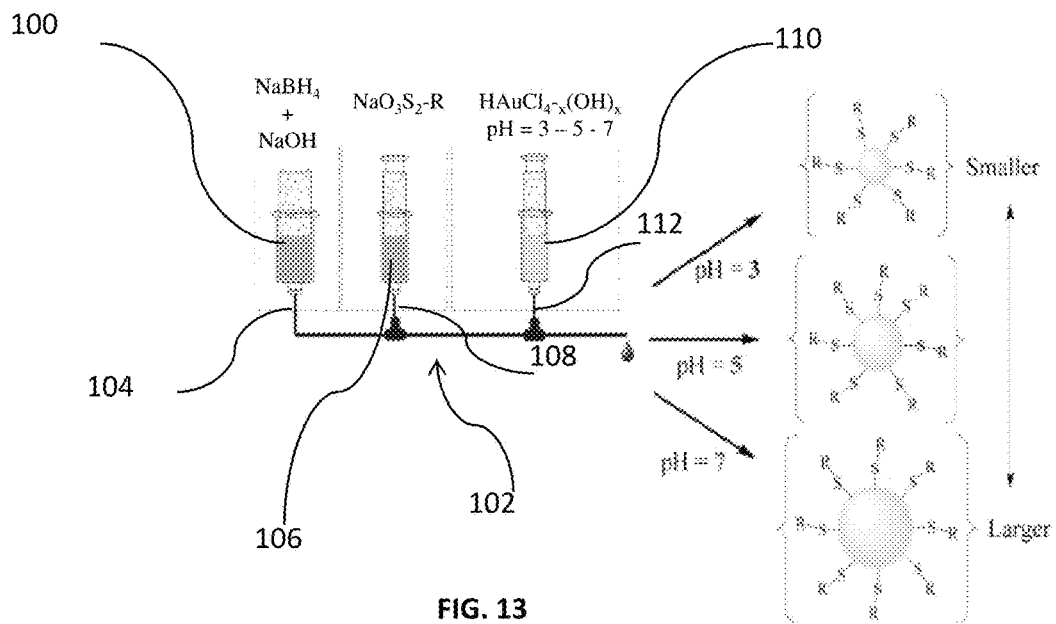

FIG. 13 is a schematic diagram illustrating an exemplary method of making gold nanoparticles using pH variation to control nanoparticle core size.

Figure 14A:
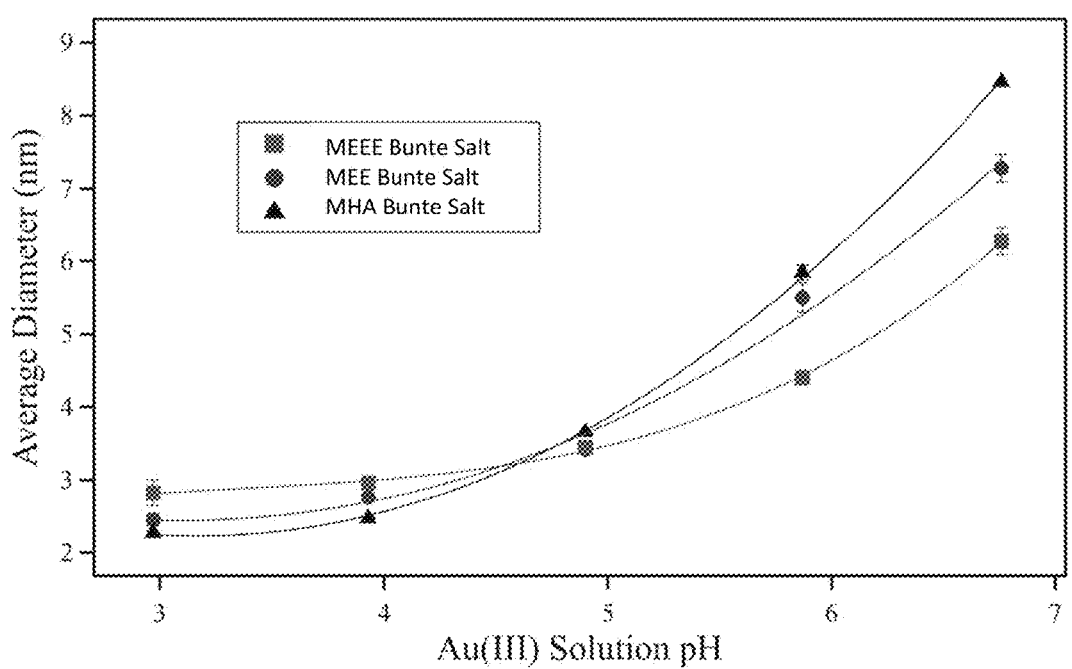
Figure 14B:
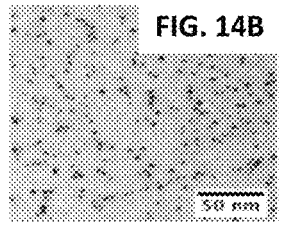
Figure 14C:
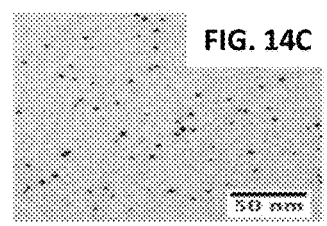
Figure 14D:
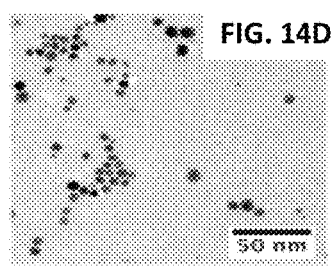
Figure 14E:
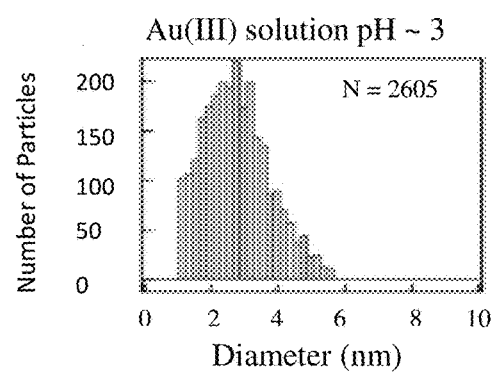
Figure 14F:
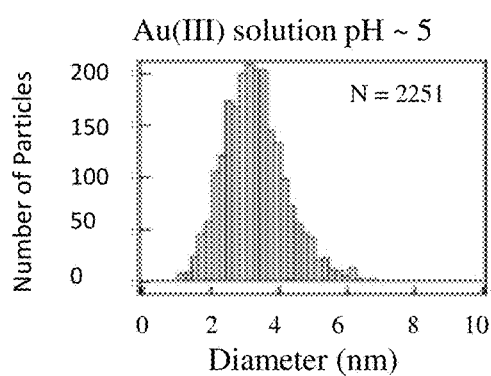
Figure 14G:
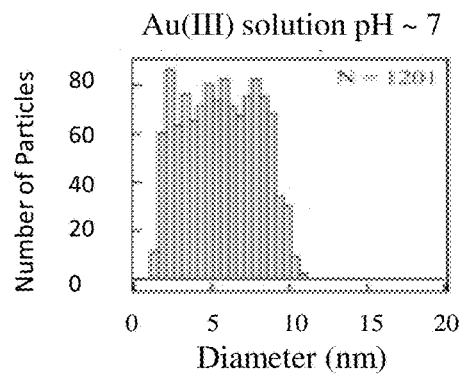

FIGS. 14A-14G illustrate results obtained from characterization analysis of particular gold nanoparticle embodiments disclosed herein; FIG. 14A is a graph of pH versus average diameter (nm) for different gold nanoparticle embodiments obtained using small-angle x-ray scatting (SAXS) analysis; FIGS. 14B and 14E illustrate a representative TEM micrograph and a size analysis graph (nm versus number of particles), respectively, for a particular gold nanoparticle embodiment made at pH 3, wherein N is the number of particles analyzed across multiple images for each sample; FIGS. 14C and 14F illustrate a representative TEM micrograph and a size analysis graph (nm versus number of particles), respectively, for a particular gold nanoparticle embodiment made at pH 5; and FIGS. 14D and 14G illustrate a representative TEM micrograph and a size analysis graph (nm versus number of particles), respectively, for a particular gold nanoparticle embodiment made at pH 7.

Figure 15:
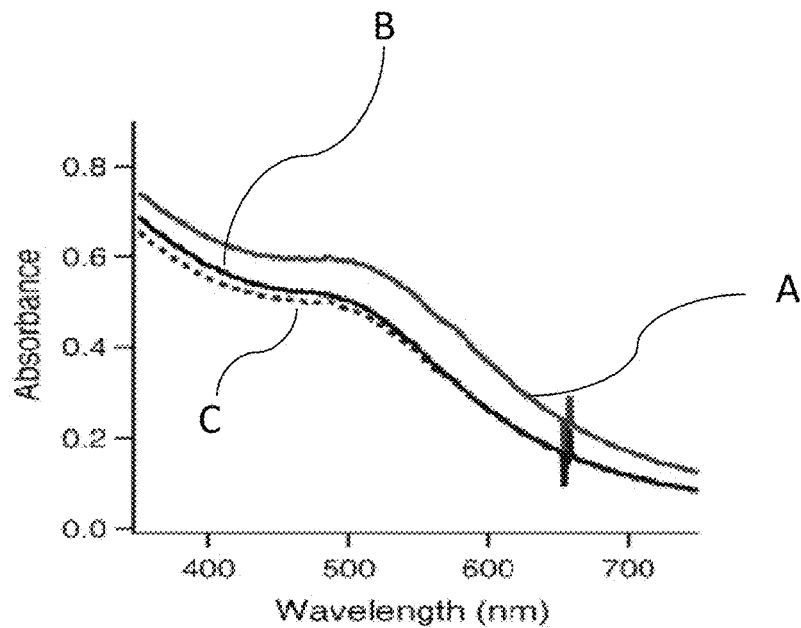

FIG. 15 is a combined UV/vis spectrum illustrating results obtained from analysis of a gold nanoparticle embodiment (line "B"), a gold nanoparticle embodiment cross-linked with $Eu^{3+}$ (line "A") and a gold nanoparticle exposed to $Eu^{3+}$ and EDTA (dotted line "C").

Figure 16A:
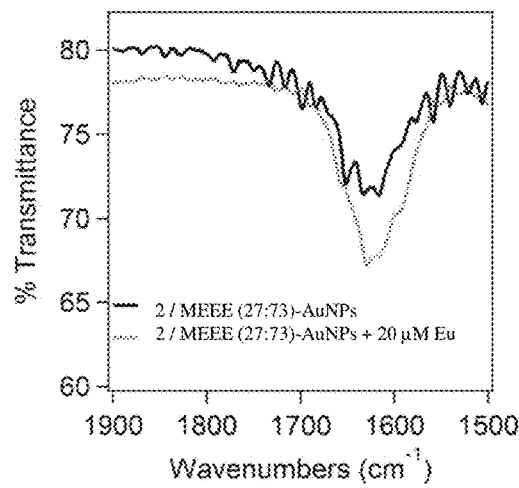
Figure 16B:
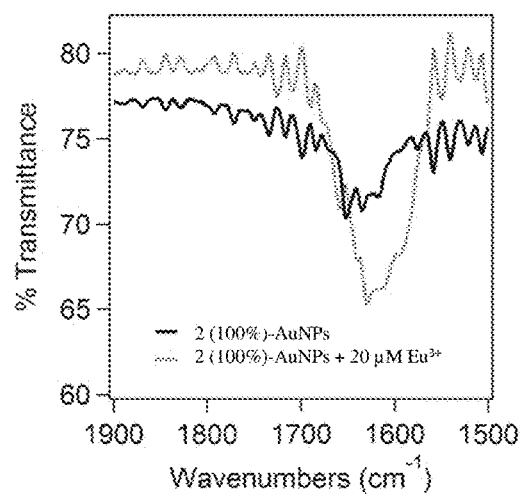

FIGS. 16A and 16B are FT-IR spectra comparing differences in % transmittance of different gold nanoparticle embodiments; FIG. 16A illustrates a particular spectral region of an exemplary gold nanoparticle embodiment comprising a mixture of ligands before and after addition of $Eu^{3+}$; and FIG. 16B illustrates a particular spectral region of an exemplary gold nanoparticle embodiment comprising a single ligand species before and after addition of $Eu^{3+}$.

Figure 17A:
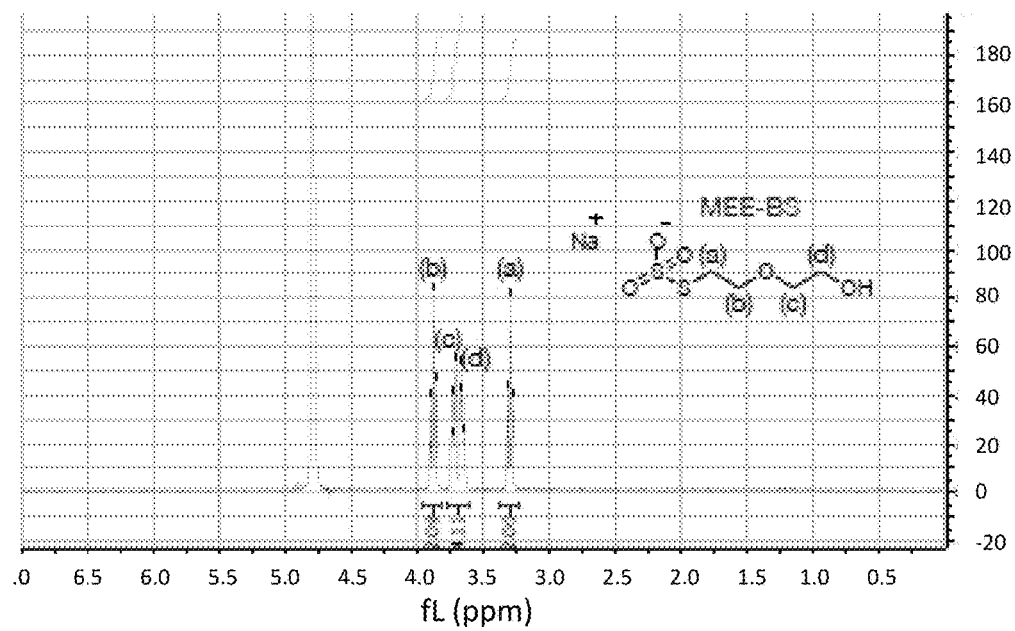
Figure 17B:
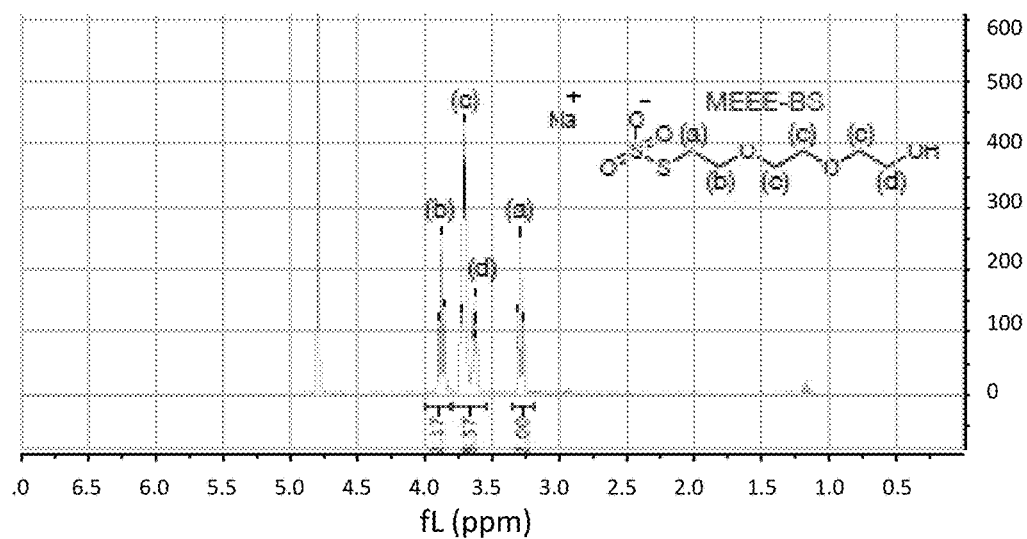
Figure 17C:
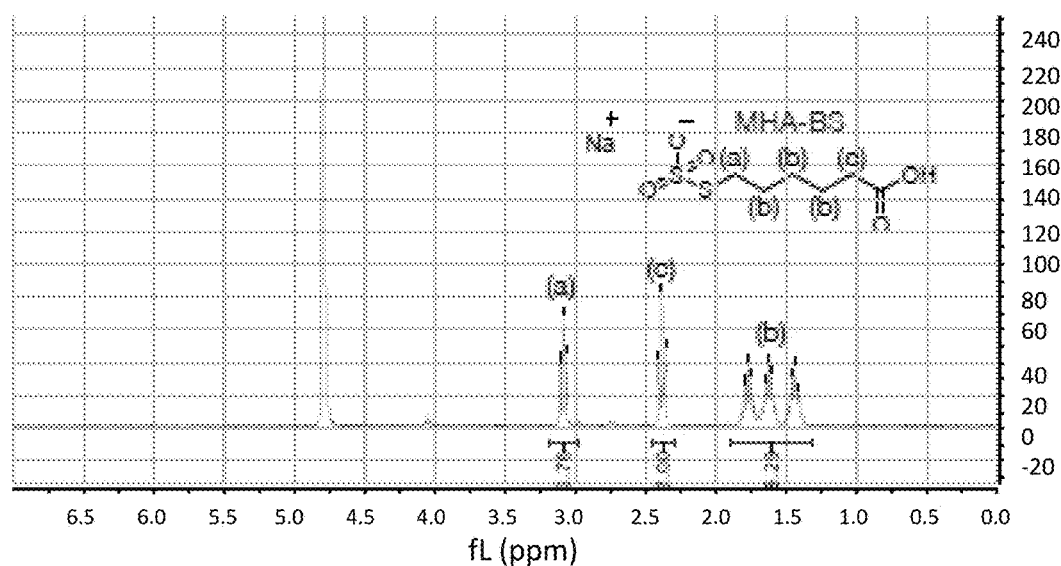

FIGS. 17A-17C are $^1$H-NMR spectra of exemplary ligand precursors disclosed herein.

Figure 18A:
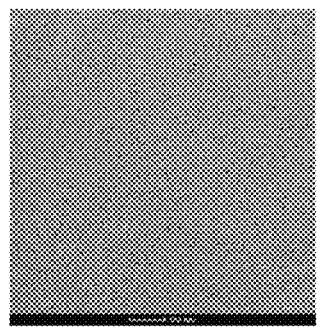
Figure 18B:
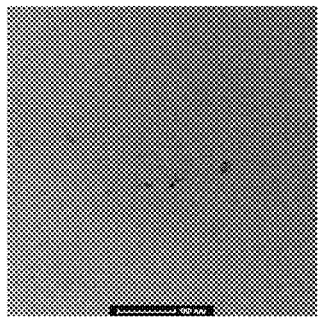
Figure 18C:
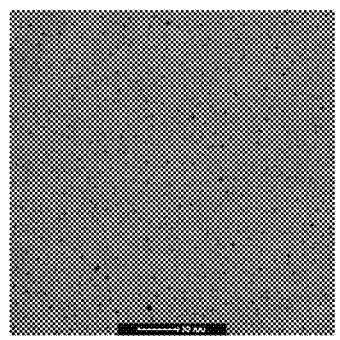
Figure 18D:
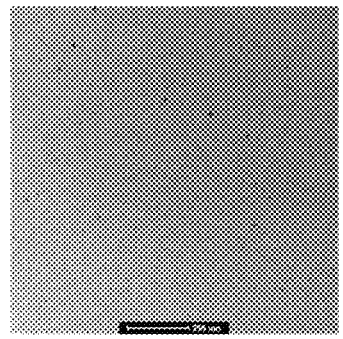
Figure 18E:
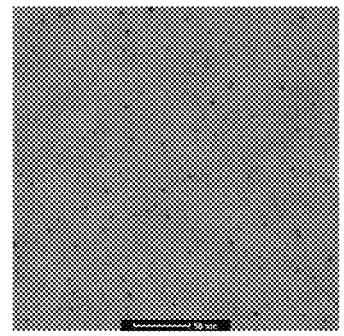
Figure 18F:
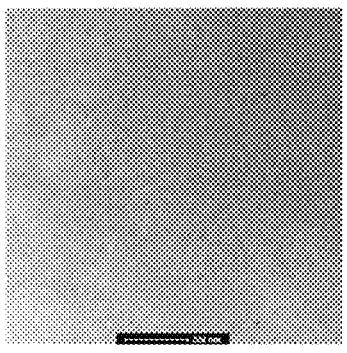
Figure 19A:
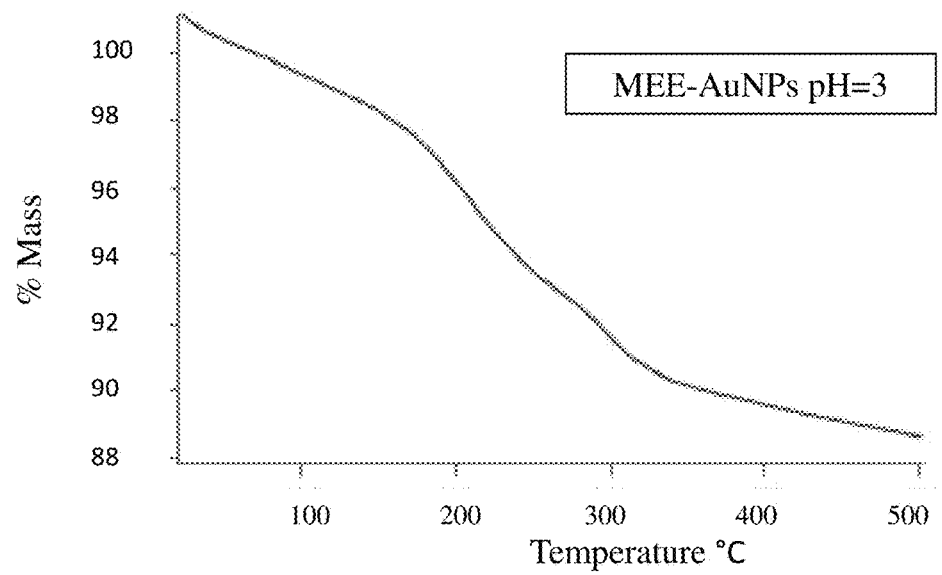
Figure 19B:
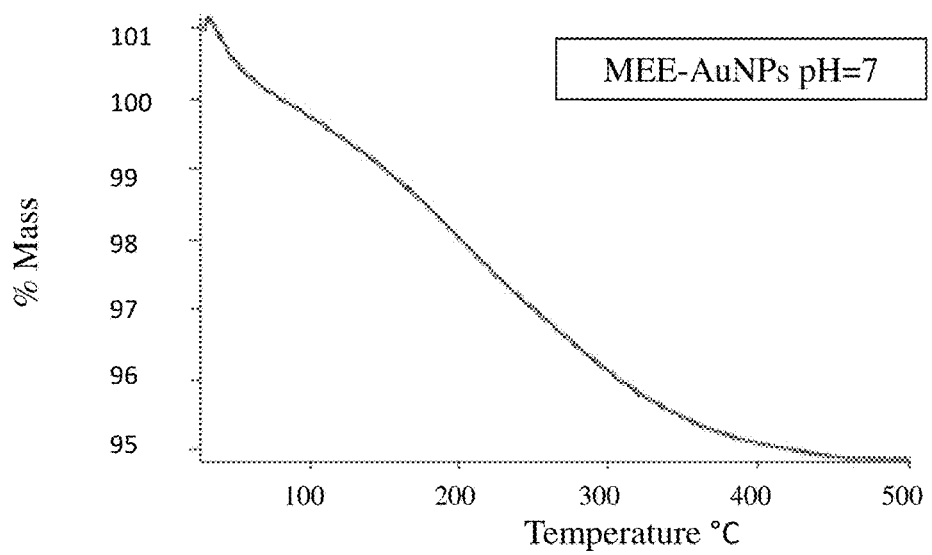
Figure 19C:
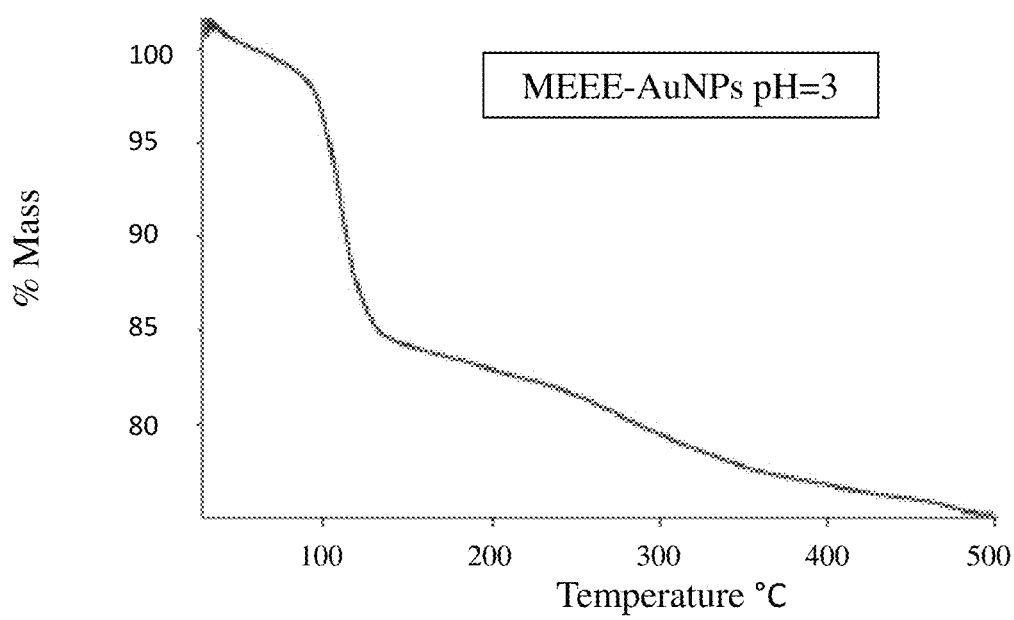
Figure 19D:
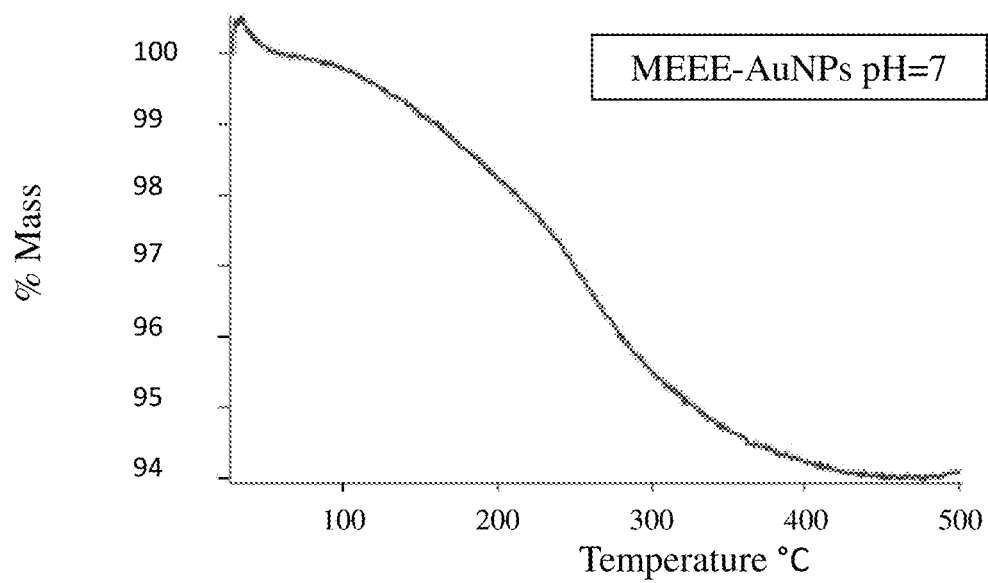
Figure 19E:
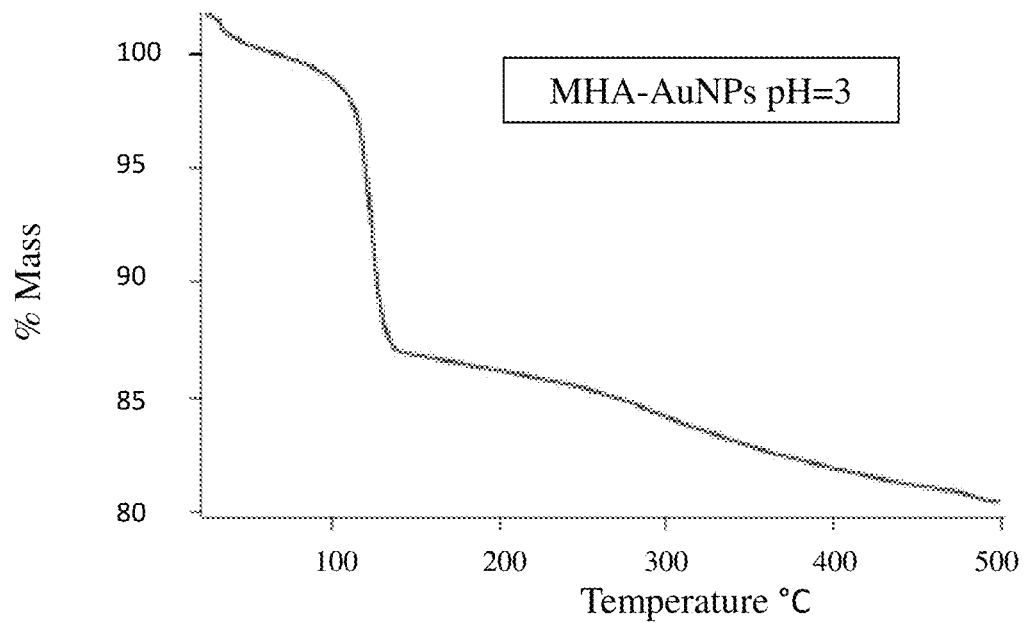
Figure 19F:
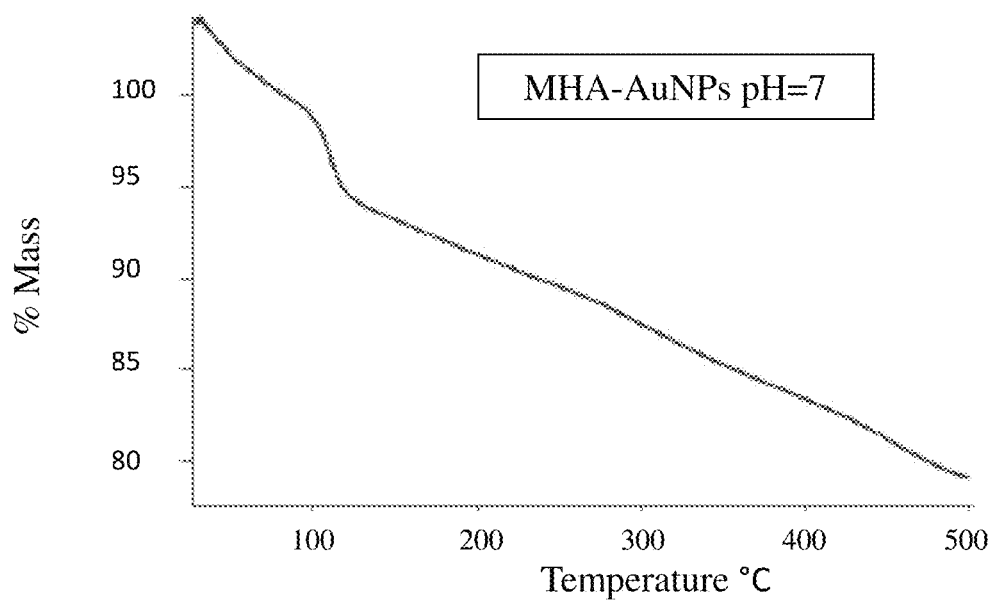

FIGS. 18A-18F are TEM micrographs of exemplary gold nanoparticle embodiments comprising different ligands at different pH levels; FIGS. 18A, 18C, and 18E are TEM micrographs of gold nanoparticle embodiments made at pH 3; and FIGS. 18B, 18D, and 18F are images of the gold nanoparticle embodiments made at pH 7 FIGS. 19A-19F are graphs of temperature (° C.) versus % mass obtained from thermogravimetric analysis of a gold nanoparticle embodiments made at pH 3 (FIGS. 19A, 19C, and 19E) and pH 7 (FIGS. 19B, 19D, and 19F).

Figure 20A:
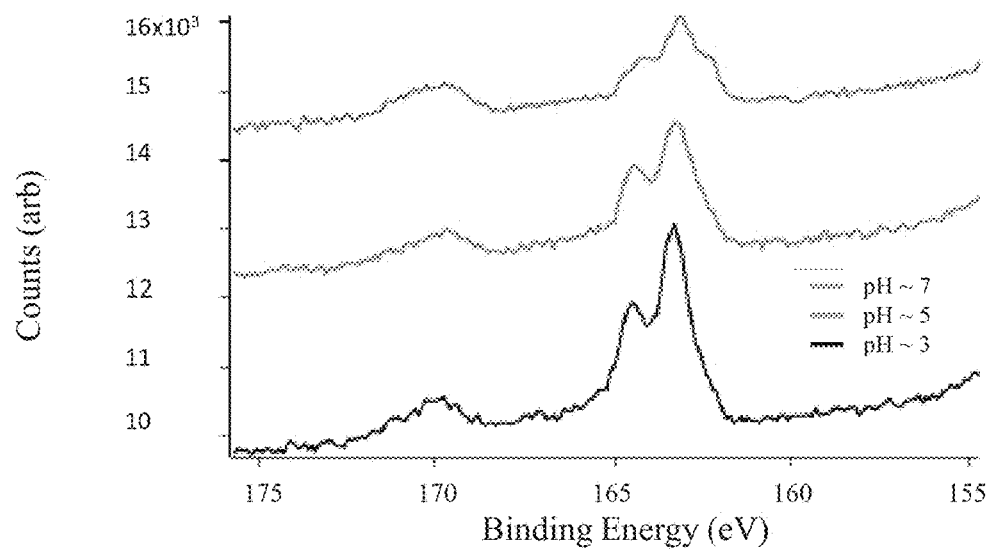
Figure 20B:
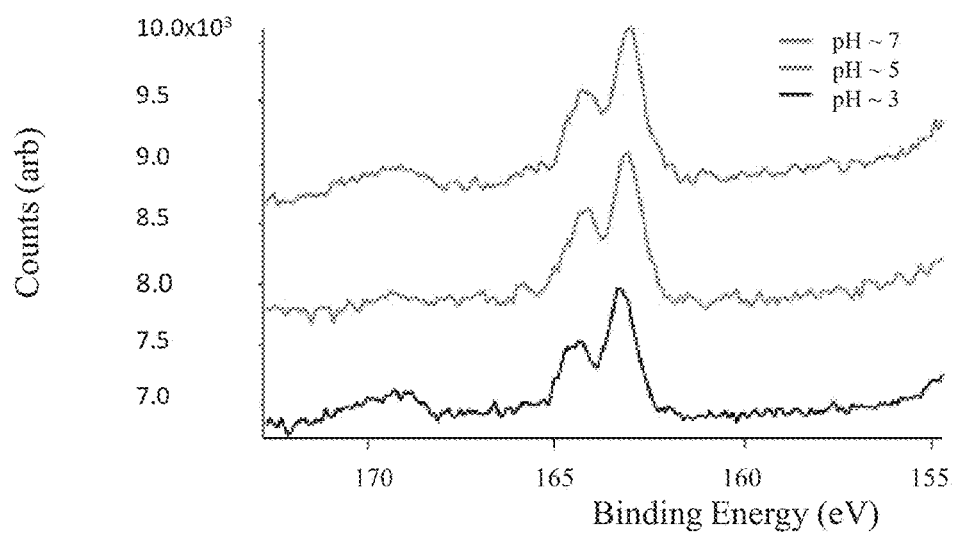
Figure 20C:
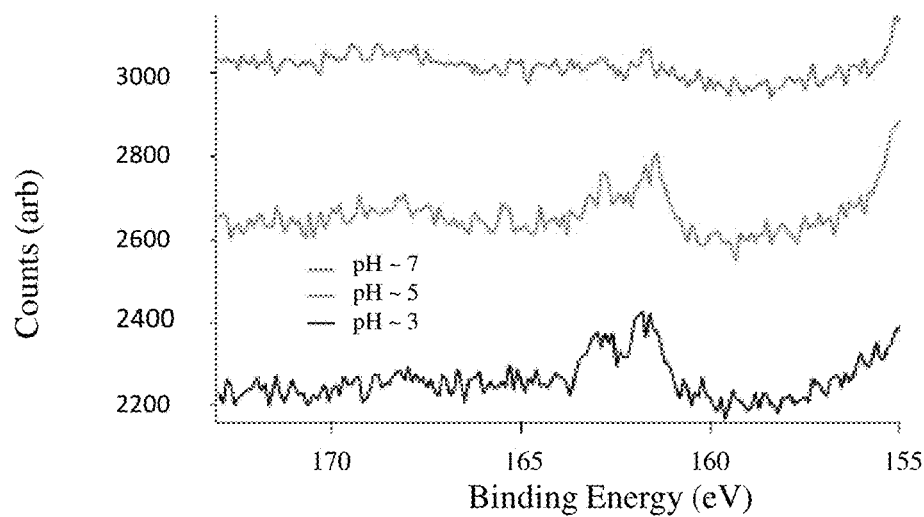

FIGS. 20A-20C are XPS spectra obtained from X-ray photoelectron spectroscopic analysis of three different exemplary gold nanoparticle embodiments having different ligands made at pH values of 3, 5, and 7.

Figure 21:
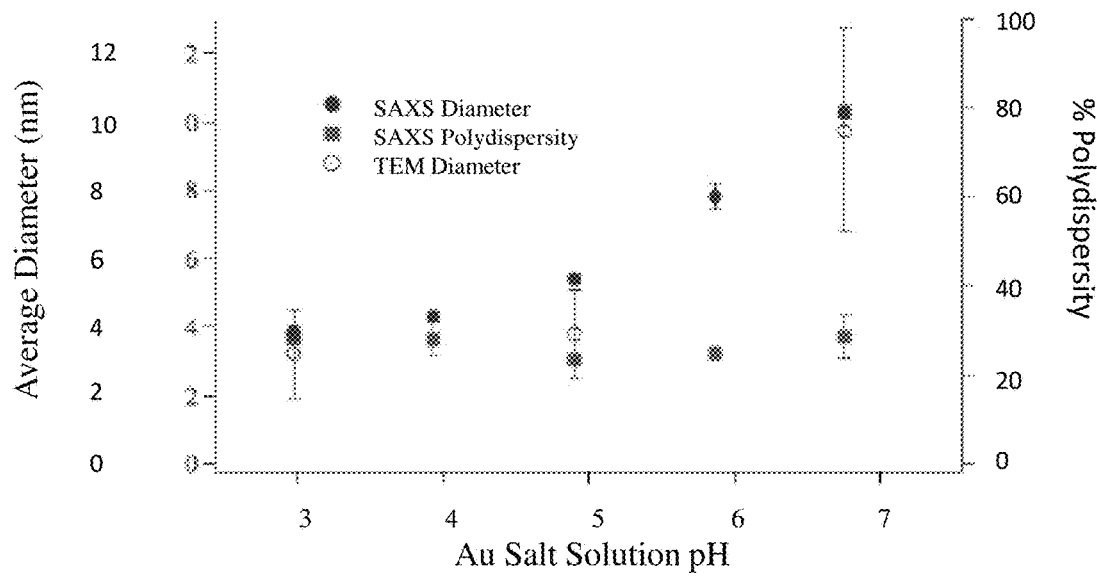

FIG. 21 is a graph illustrating combined SAXS data obtained from analysis of batch-wise production of exemplary gold nanoparticle embodiments.

Figure 22:
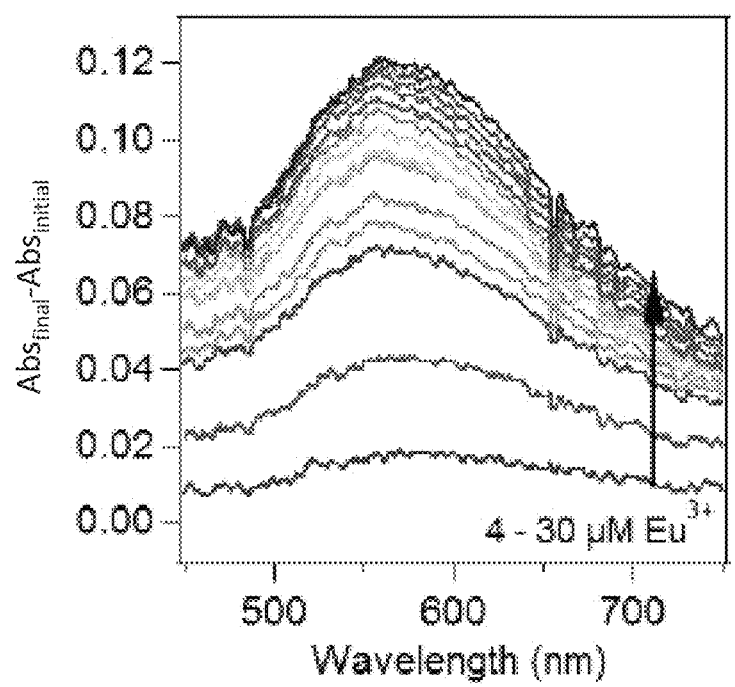

FIG. 22 is a graph of wavelength (nm) versus change in absorbance illustrating the upper sensing limit of $Eu^{3+}$ as determined for an exemplary gold nanoparticle embodiment using UV/vis spectral titration.

Figure 23:
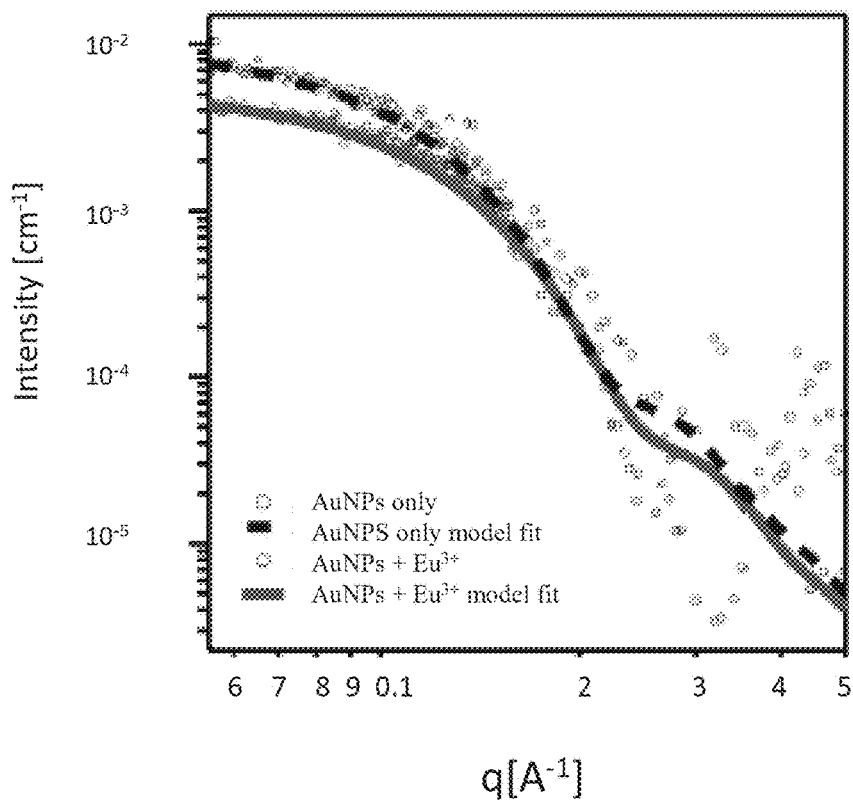

FIG. 23 is a graph illustrating the raw SAXS pattern of an exemplary gold nanoparticle embodiment before and after $Eu^{3+}$-induced cross-linking.

Figure 24A:
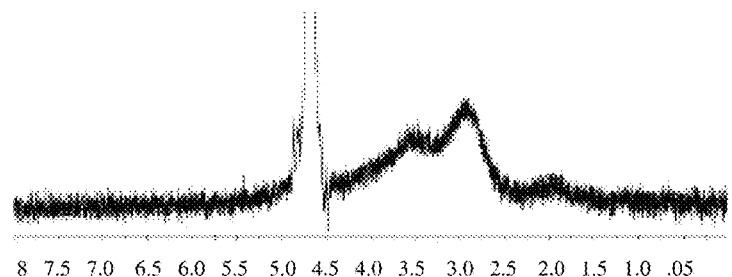
Figure 24B:
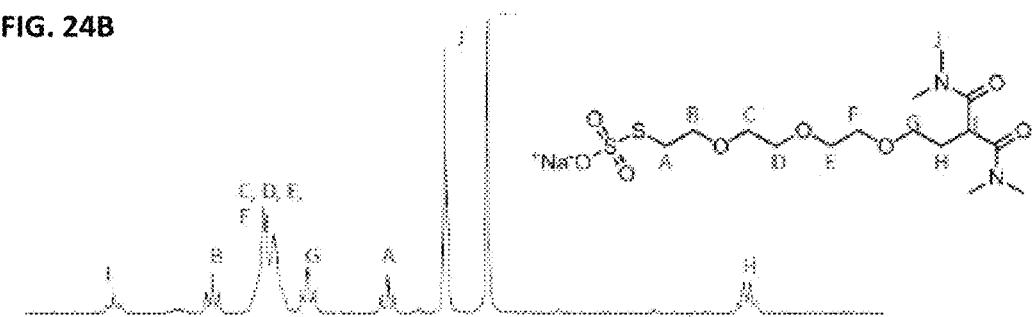
Figure 24C:
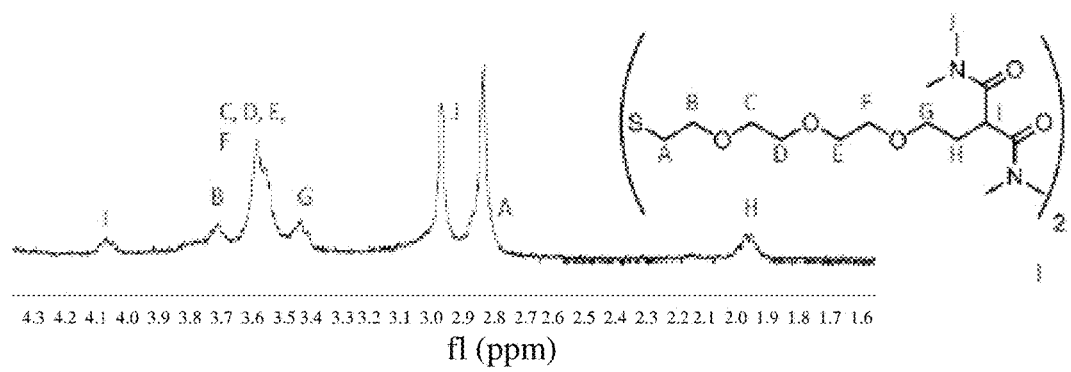

FIGS. 24A-24C are $^1$H-NMR spectra of a gold nanoparticle embodiment and an exemplary ligand before and after being coupled to the gold nanoparticle; FIG. 24A is an $^1$H-NMR spectrum of an exemplary gold nanoparticle embodiment; FIG. 24B is an $^1$H-NMR spectrum of an exemplary ligand before coupling to the gold nanoparticle; and FIG. 24C is an $^1$H-NMR spectrum of the ligand of FIG. 24B after coupling with the gold nanoparticle.

FIG. 25 is a combined $^1$H-NMR spectrum illustrating results from $I_2$ decomposition of an exemplary gold nanoparticle embodiment comprising varying ratios of an exemplary ligand.

FIGS. 26A and 26B are $^1$H-NMR spectra of an exemplary gold nanoparticle; FIG. 26A is a spectrum obtained before addition of $I_2$ to release surface bound ligands as disulfides in $D_2O$; and FIG. 26B is a spectrum obtained after addition of $I_2$.

Figure 27:
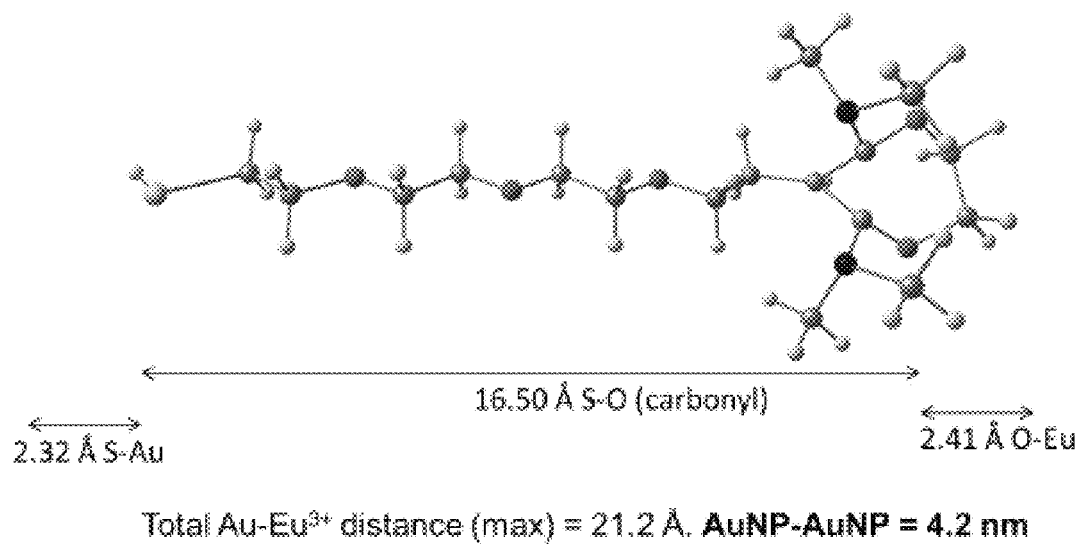

FIG. 27 is a diagram illustrating the total Au—$Eu^{3+}$ distance of an exemplary gold nanoparticle embodiment used to detect $Eu^{3+}$.

Figure 28:
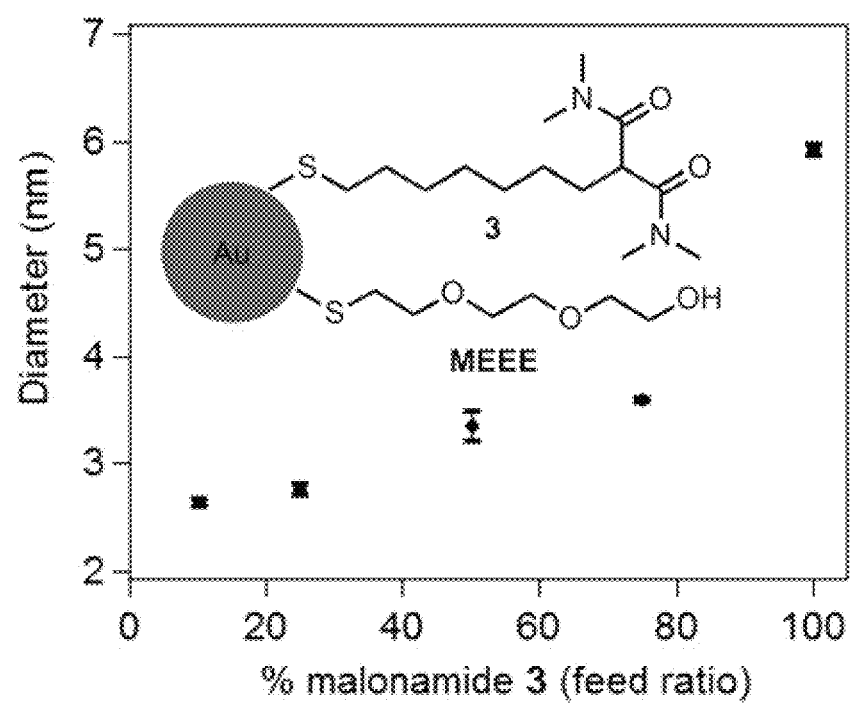

FIG. 28 is a graph illustrating the effect of ligand precursor feed ratio on gold nanoparticle diameter in an exemplary embodiment.

Figure 29A:
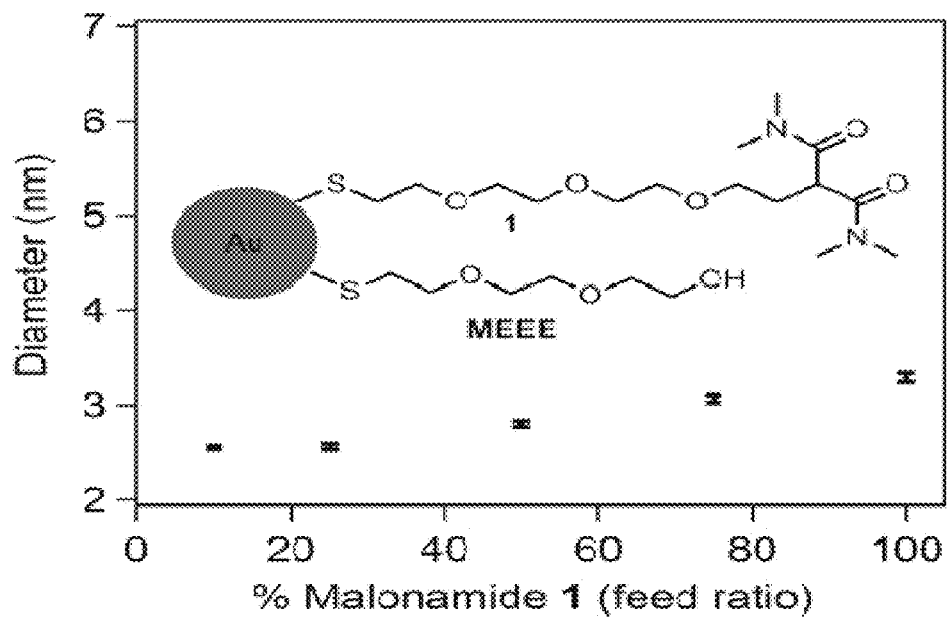
Figure 29B:
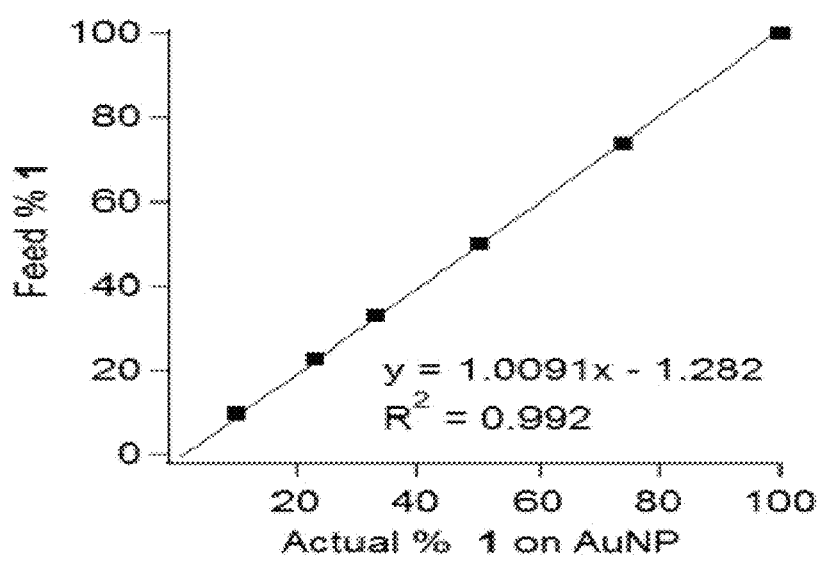

FIGS. 29A and 29B are graphs illustrating the effect of ligand precursor feed ratio on gold nanoparticle diameter and functionalization ratio of an exemplary gold nanoparticle embodiment; FIG. 29A illustrates the average core sizes as determined by SAXS; and FIG. 29B illustrates that the feed ratio of an exemplary ligand was directly related to the functionalization ratio of the gold nanoparticle product.

Figures 30A, 30B, 30C:
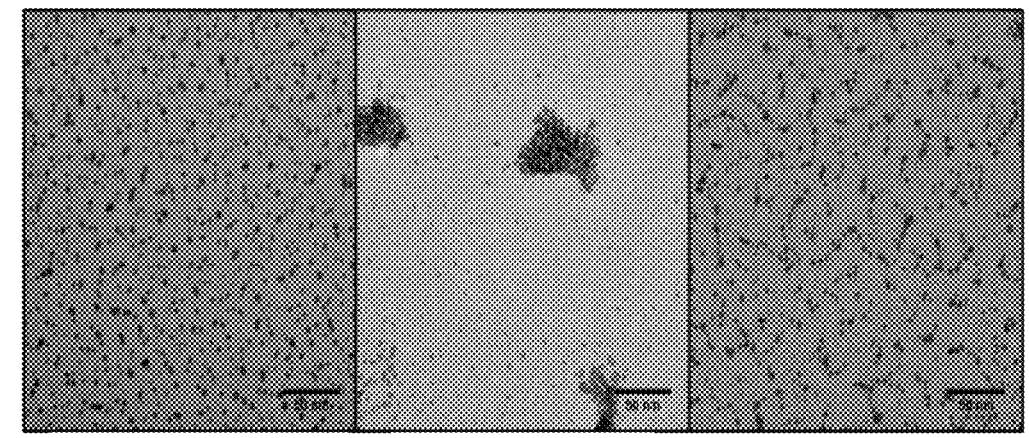

FIGS. 30A-30C are TEM images of various different gold nanoparticle embodiments; FIG. 30A is a TEM image of a dispersed gold nanoparticle embodiment; FIG. 30B is a TEM image of a cross-linked gold nanoparticle embodiment after addition of $Eu^{3+}$; and FIG. 30C is a TEM image of a re-dispersed gold nanoparticle embodiment after addition of EDTA.

Figure 31:
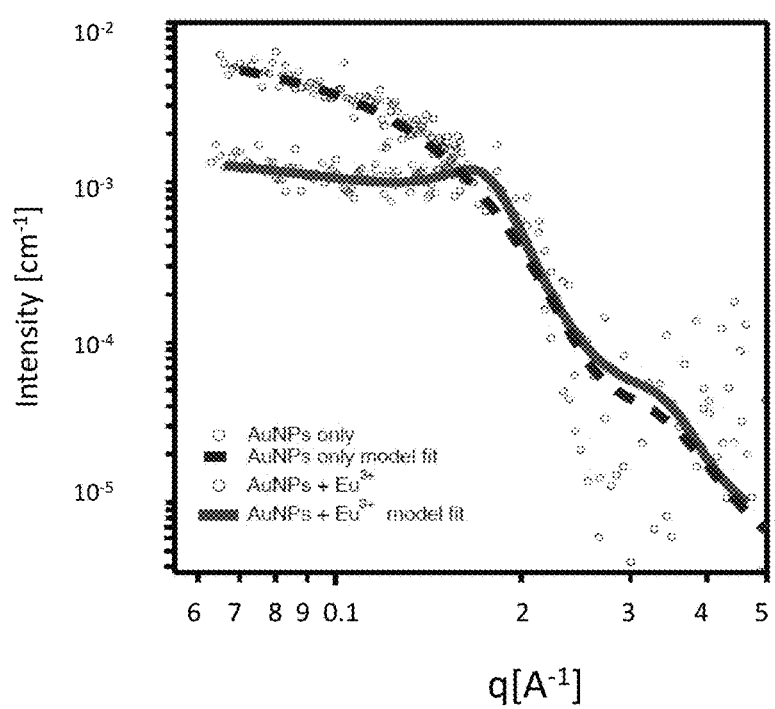

FIG. 31 is a graph illustrating SAXS results of dispersed gold nanoparticle embodiments and agglomerates obtained from the addition of $Eu^{3+}$.

FIG. 32 is a graph illustrating the effect of ligand precursor feed ratio on gold nanoparticle diameter in an exemplary embodiment.

Figure 33B:
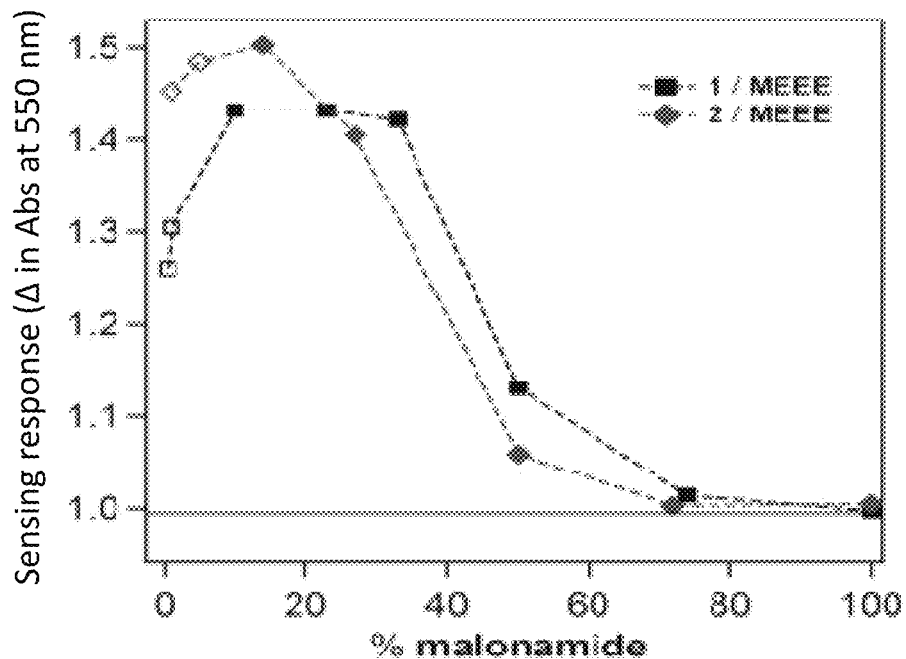
Figure 33C:
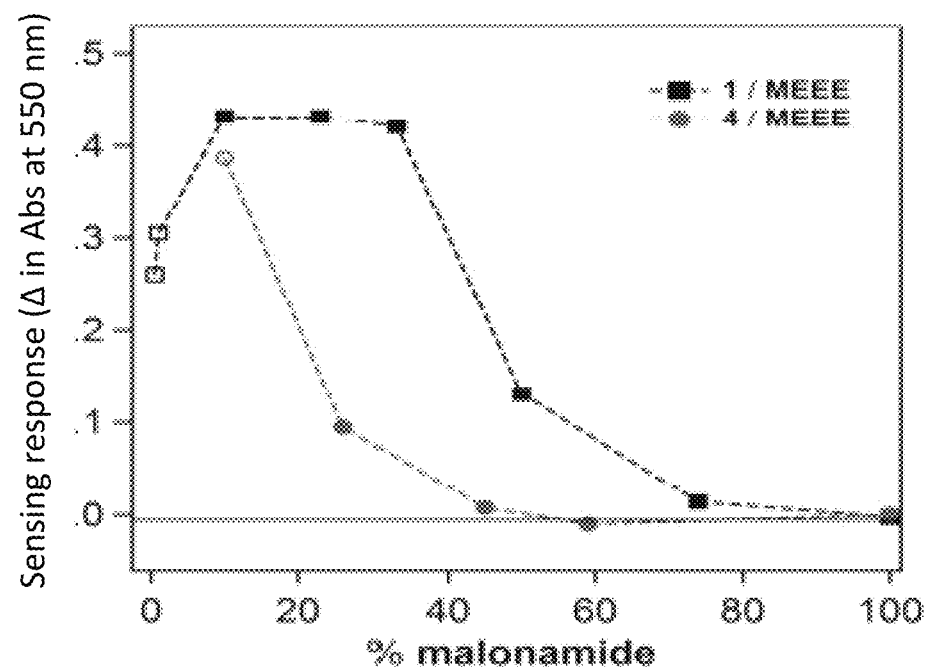

FIGS. 33A-33C illustrate sensing interactions of exemplary gold nanoparticle embodiments; FIG. 33A is a schematic of exemplary gold nanoparticles and the sensing interaction with $Eu^{3+}$ in a 2:1 ligand to metal fashion from neighboring particles; FIG. 33B is graph illustrating results obtained from an exemplary nanoparticle embodiment comprising a malonamide terminal functional group wherein the sensing response was monitored as a function of ligand tether length and % malonamide; and FIG. 33C illustrates results obtained from an exemplary nanoparticle embodiment comprising a malonamide terminal functional group wherein the sensing response was monitored as a function of amide substituent and % malonamide.

Figure 34:
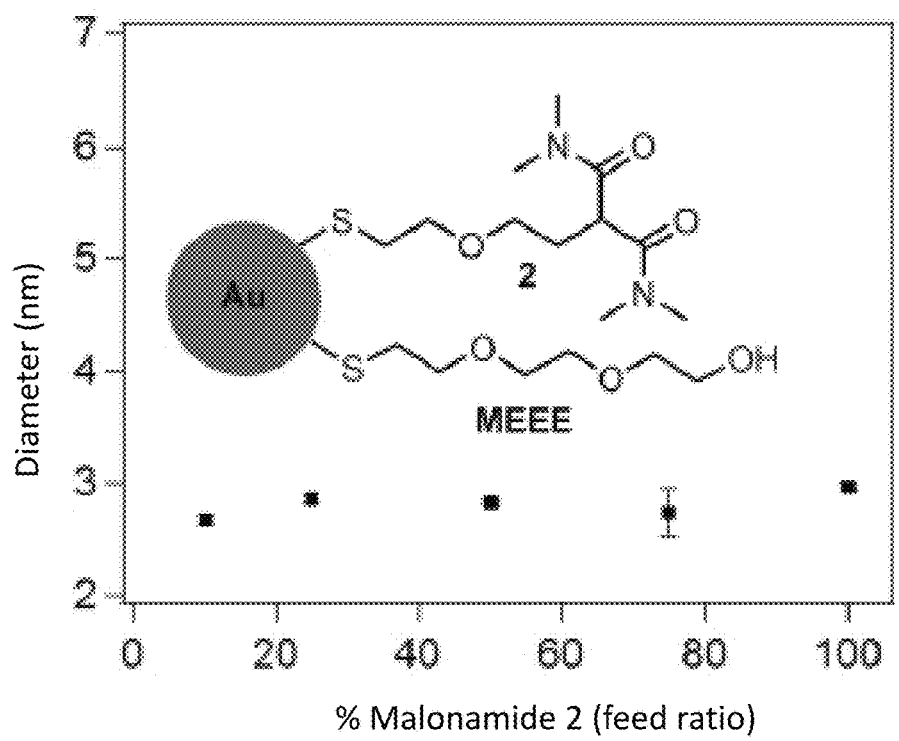

FIG. 34 is a graph illustrating the effect of ligand feed ratio on gold nanoparticle diameter in an exemplary embodiment.

Figure 35:
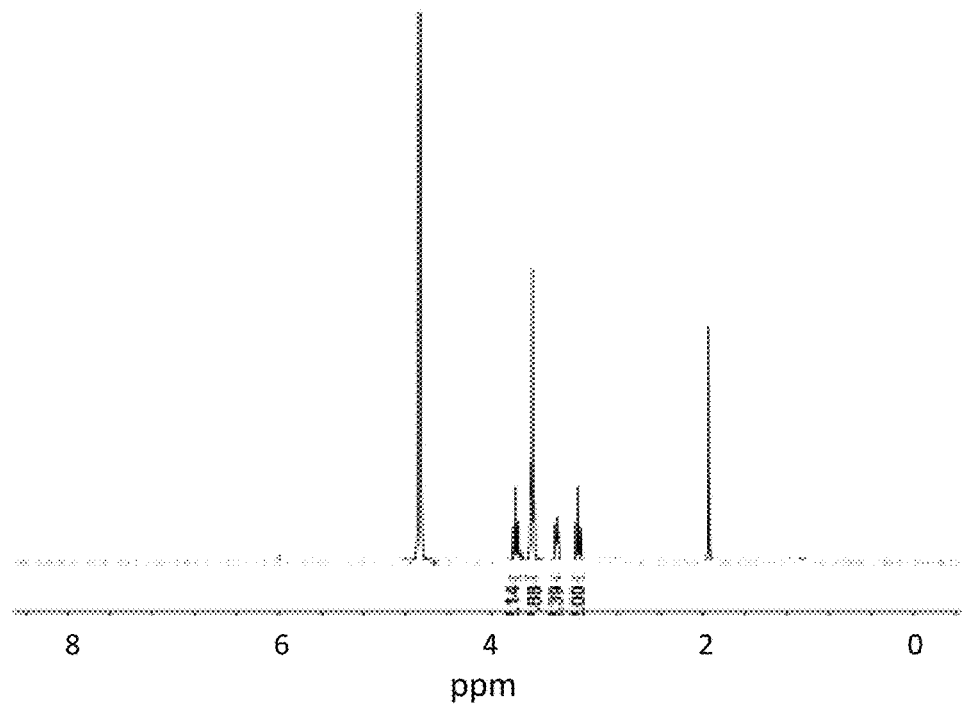

FIG. 35 is an exemplary $^1$H-NMR spectrum of a ligand embodiment disclosed herein.

Figure 36:
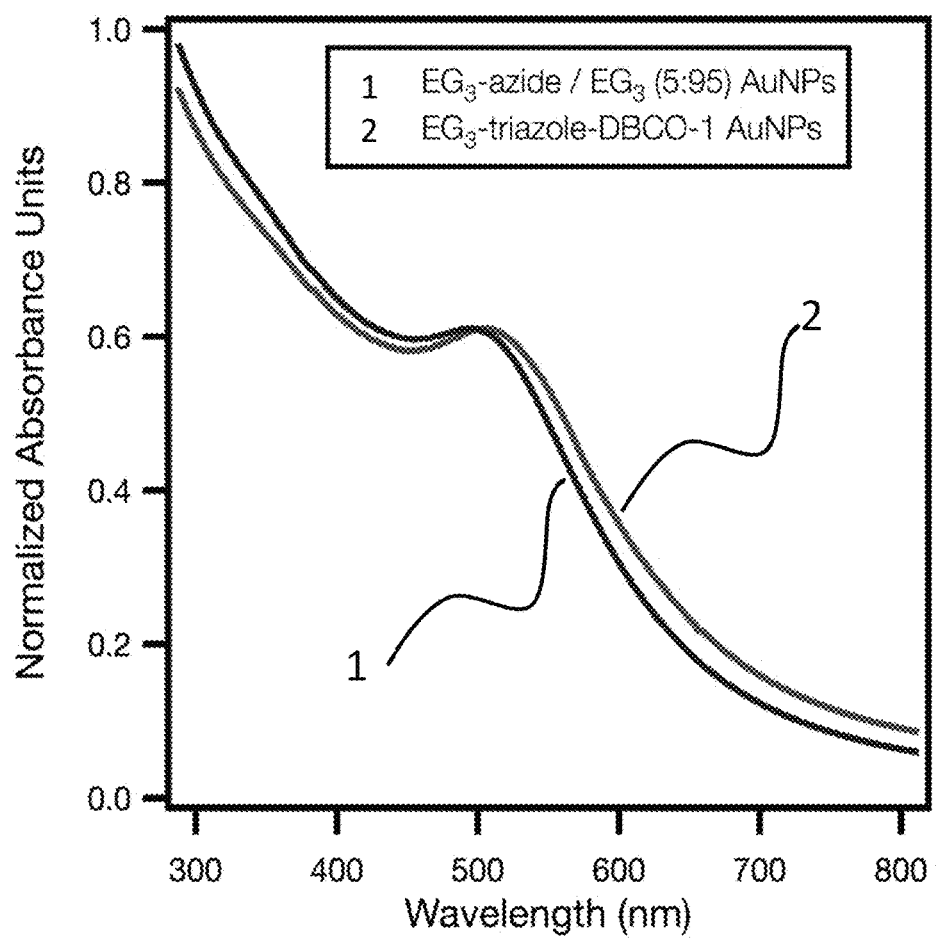

FIG. 36 is a UV/vis spectrum of an exemplary gold nanoparticle embodiment comprising a clickable functional group before (line 1) and after (line 2) reaction with a reactive compound capable of reacting with the clickable functional group.

Figure 37A:
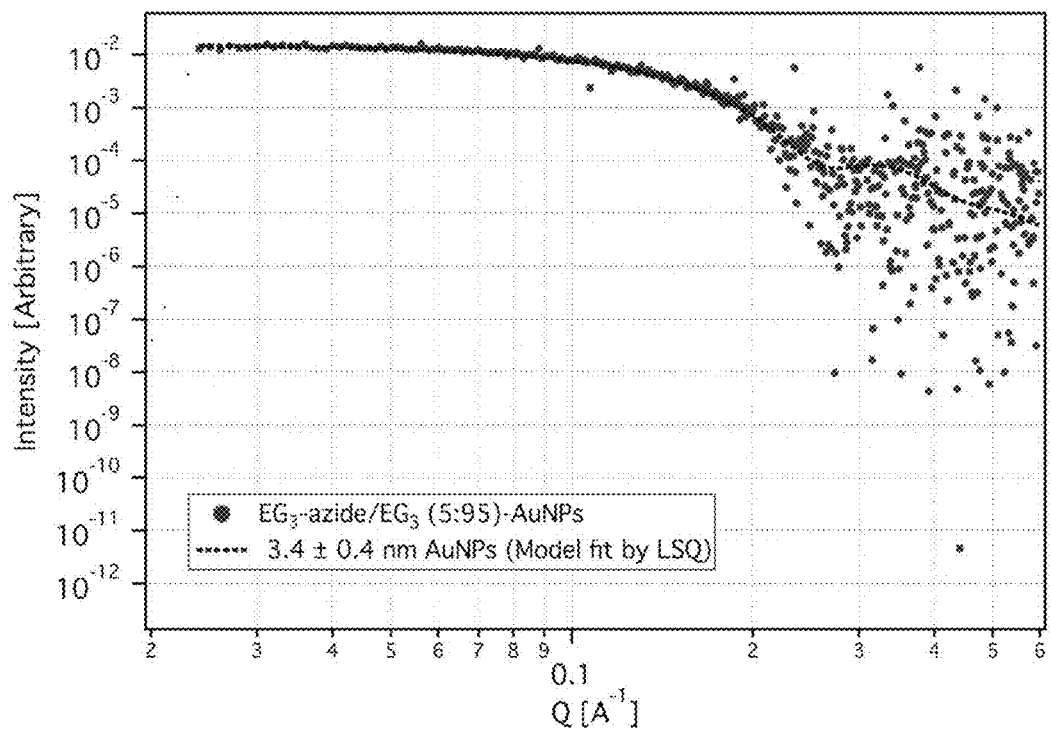
Figure 37B:
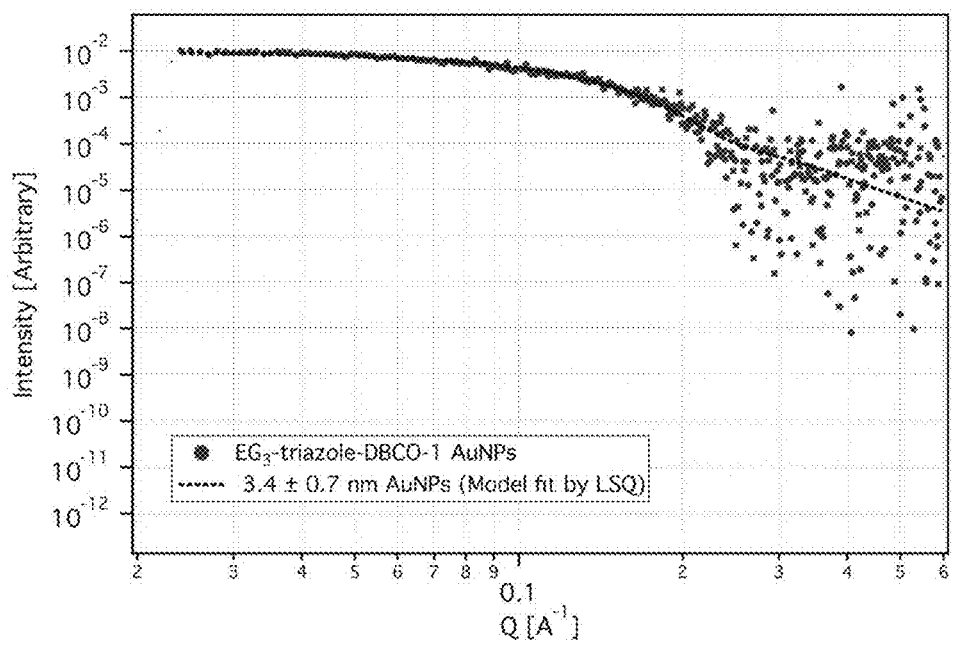

FIGS. 37A and 37B are graphs illustrating raw SAXS patterns and overlaid LSQ model fits for a gold nanoparticle embodiment comprising a clickable functional group before (FIG. 37A) and after (FIG. 37B) reaction with a reactive compound capable of reacting with the clickable functional group.

Figure 38:
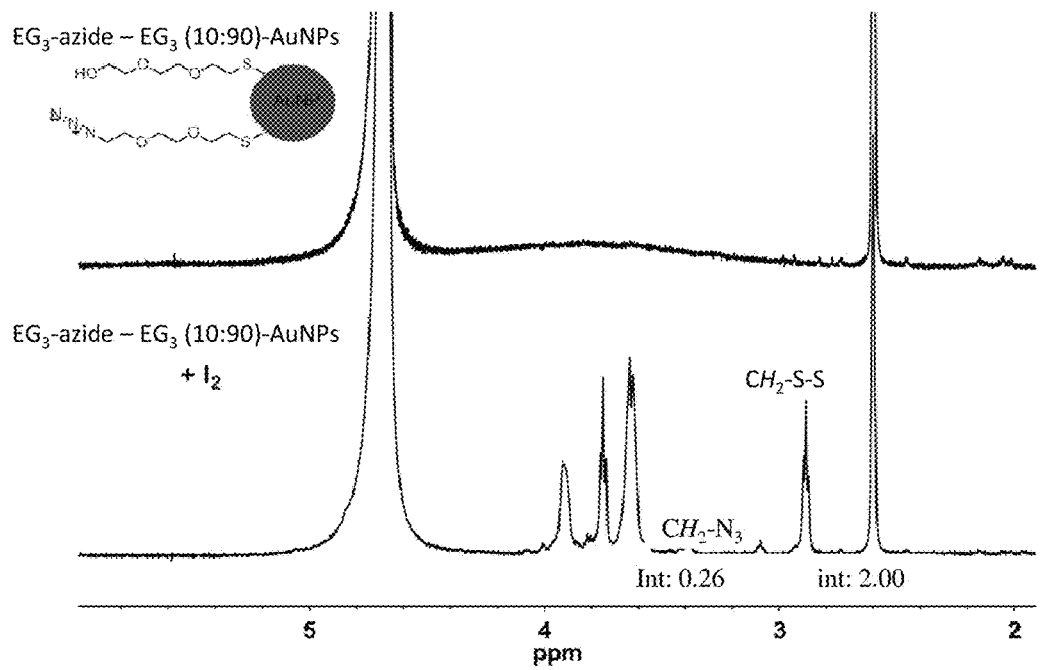

FIG. 38 is an $^1$H-NMR spectrum of an exemplary gold nanoparticle embodiment before (top) and after (bottom) $I_2$ decomposition.

Figure 39:
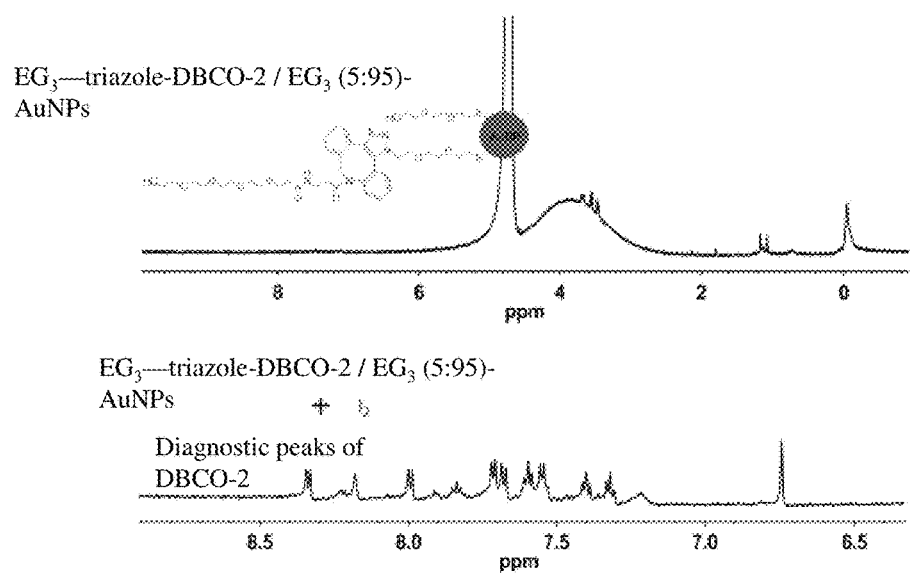

FIG. 39 is an $^1$H-NMR spectrum of an exemplary gold nanoparticle embodiment before (top) and after (bottom) $I_2$ decomposition.

Figure 40:
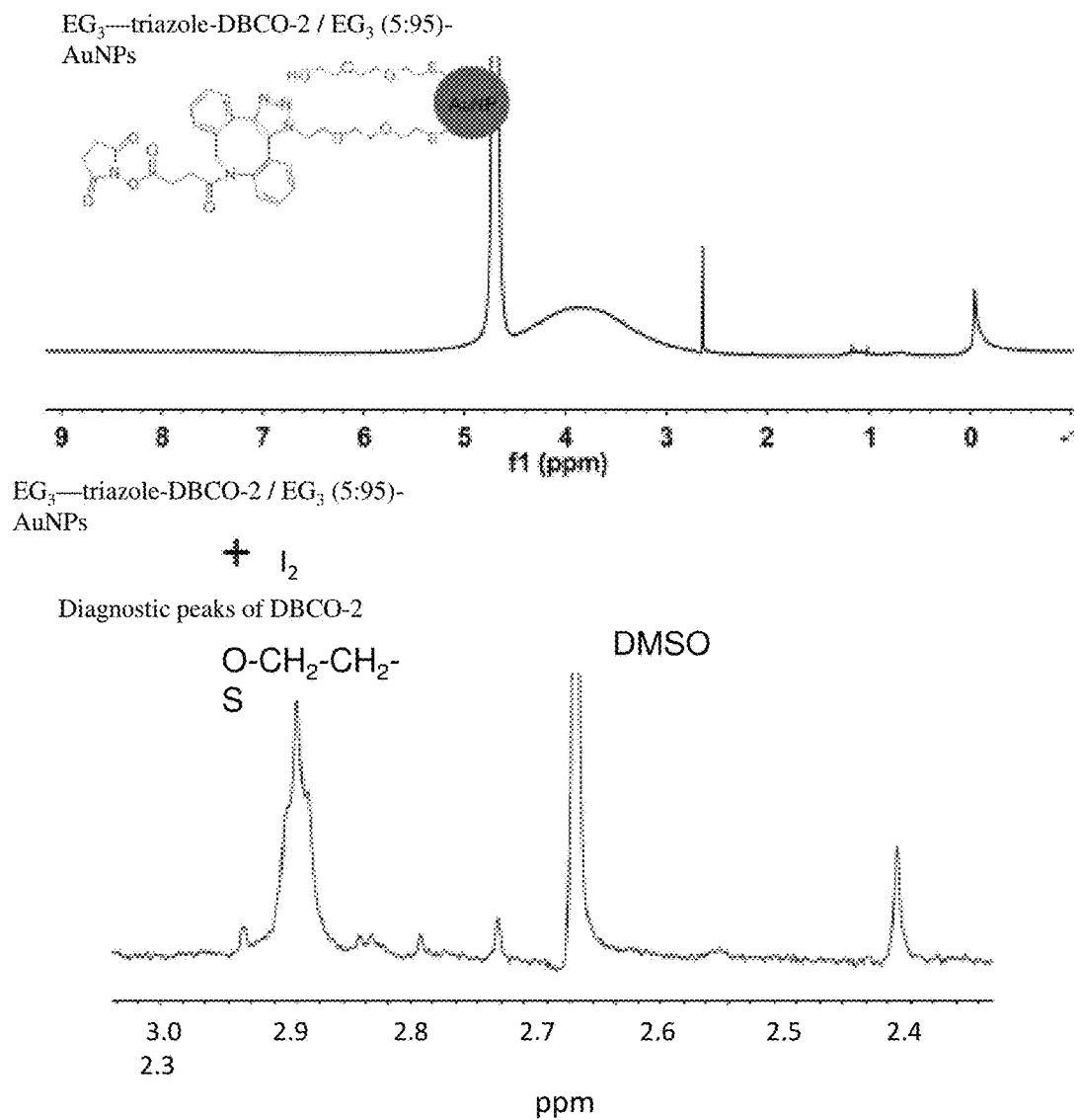

FIG. 40 is an $^1$H-NMR spectrum of an exemplary gold nanoparticle embodiment before (top) and after (bottom) $I_2$ decomposition.

Figure 41:
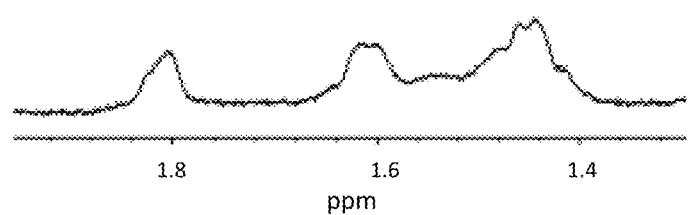

FIG. 41 is an $^1$H-NMR spectrum of an exemplary gold nanoparticle embodiment.

Figure 42:
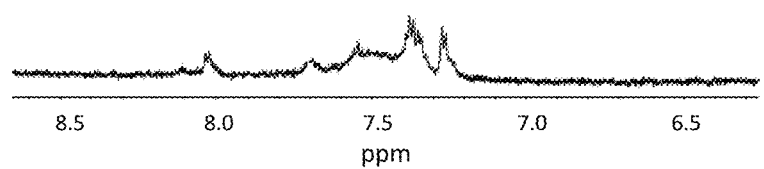

FIG. 42 is an $^1$H-NMR spectrum of an exemplary gold nanoparticle embodiment.

Figure 43:
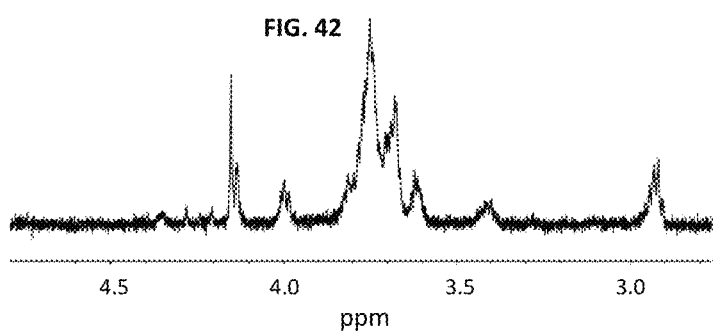

FIG. 43 is an $^1$H-NMR spectrum of an exemplary gold nanoparticle embodiment.

Figure 44:
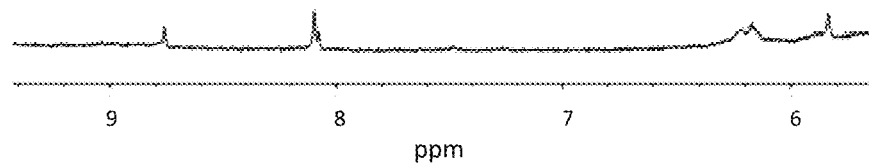

FIG. 44 is an $^1$H-NMR spectrum of an exemplary gold nanoparticle embodiment.

Figure 45:
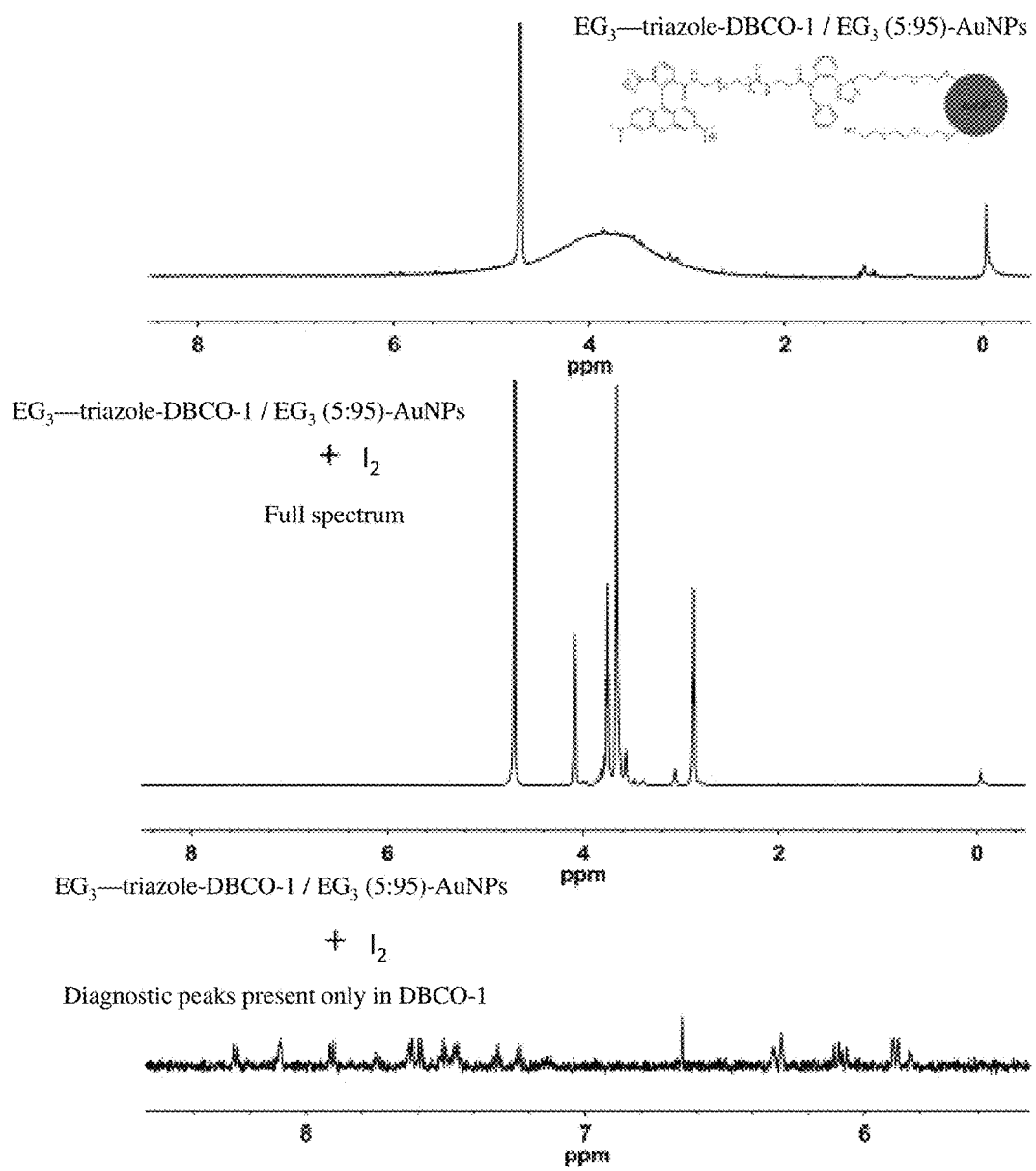

FIG. 45 is an $^1$H-NMR spectrum of an exemplary gold nanoparticle embodiment before (top) and after (middle) $I_2$ decomposition, with an expanded view of the spectrum provided (bottom).

Figure 46A:
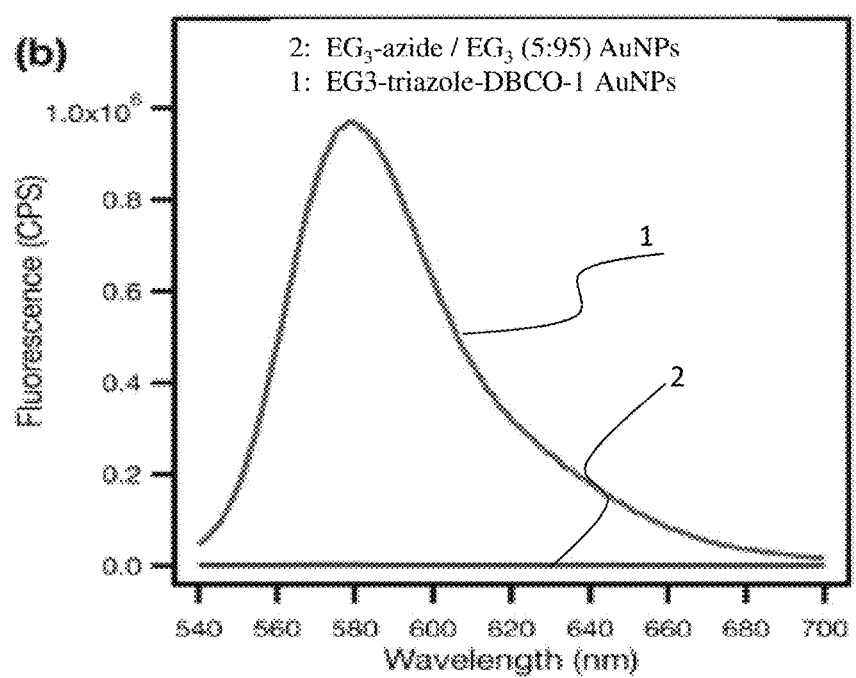
Figure 46B:
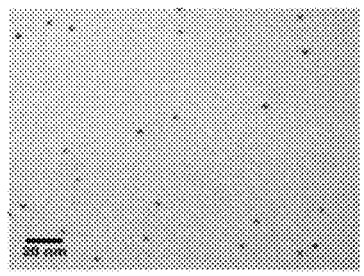
Figure 46C:
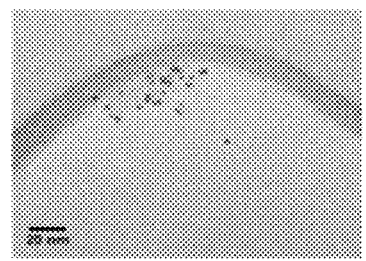

FIGS. 46A-46C illustrate results obtained from reacting a gold nanoparticle embodiment disclosed herein with another compound using click chemistry; FIG. 46A is a graph of wavelength (nm) versus fluorescence (CPS) obtained from comprising a clickable functional group (line 1) and the product obtained after reacting the gold nanoparticle embodiment with a reactive compound capable of reacting with the clickable functional group (line 2); and FIGS. 46A and 46B are TEM micrographs obtained from the gold nanoparticle embodiment of FIG. 46A prior to (FIG. 46B) and after (FIG. 46C) reaction with a reactive compound capable of reacting with the clickable functional group of the gold nanoparticle.

Figure 47A:
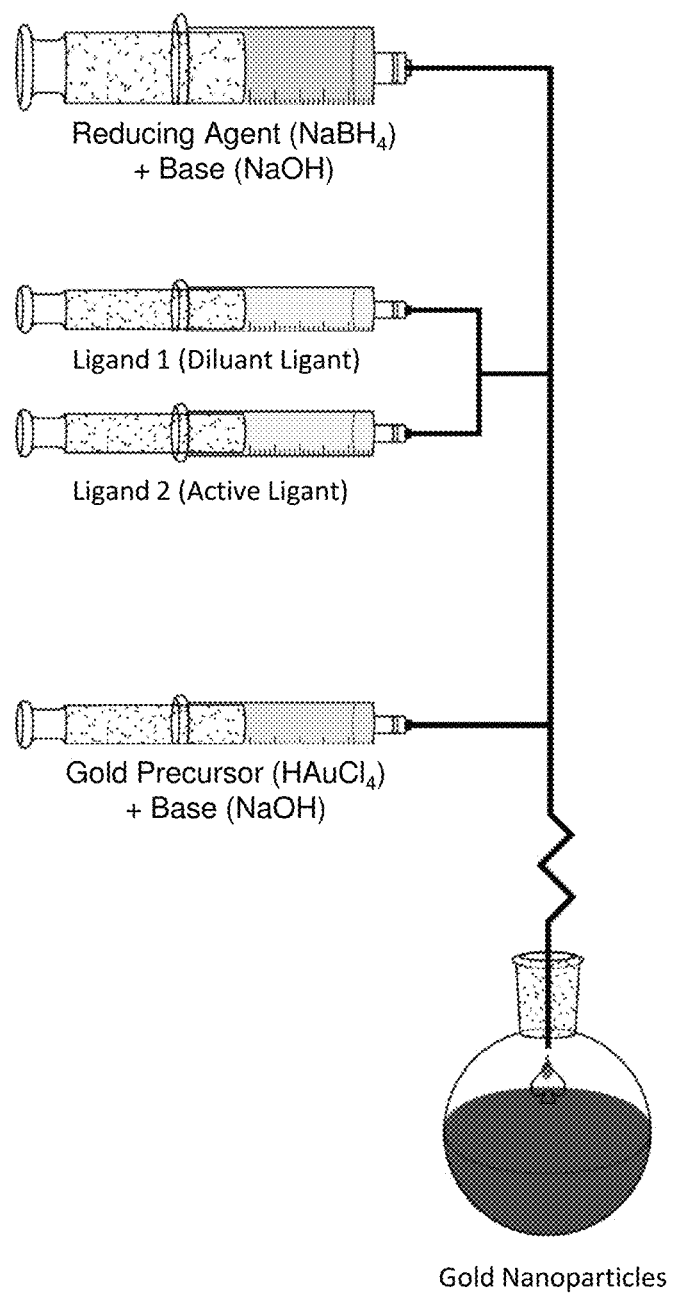
Figure 47B:
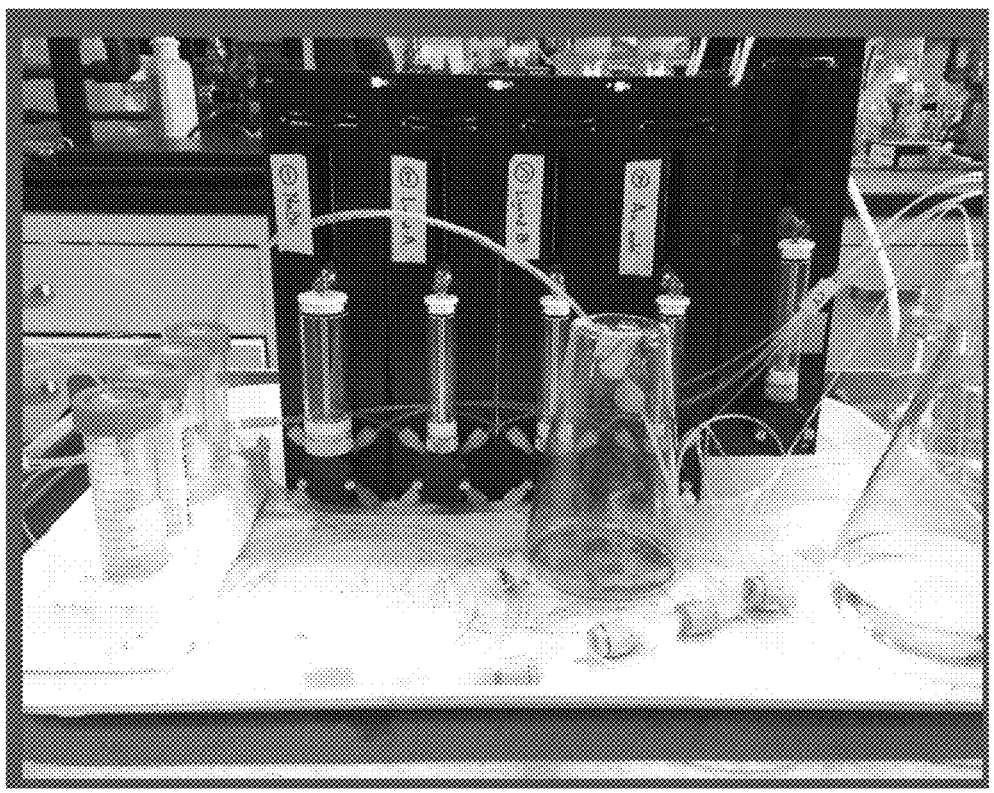

FIGS. 47A and 47B are images of exemplary flow reactors.

DETAILED DESCRIPTION

Modular methods for the construction of new nanomaterials are disclosed herein that provide simultaneous fine tunable control over size, functionality, and functional group density of gold nanoparticles. While individual properties may be broadly dictated (for example core diameter), simultaneous and precise control over all properties cannot be achieved in an economically efficient manner using traditional methods of gold nanoparticle synthesis. For nanomaterial applications there is a long-felt need in the art for a synthetic method that affords precise control of functionality, functional group density, and core diameter. Previous work in the field has demonstrated that thiol ligands used in varied ratios with core material does not afford the precise control over a narrow range of sizes during synthesis as compared to embodiment of the methods disclosed herein. Additional functionality obtained using traditional methods is only afforded when synthesis is followed by ligand exchange, which in turn introduces additional problems such as incomplete exchange of the ligand shell, inadequate and/or irreproducible control over ligand shell composition, and core size changes due to growth, etching, and/or instability. While the ratio of reagents may be used in certain instances to broadly determine final particle diameter, the low degree of precision is detrimental to the leveraging of functional physical properties. Further, the reduction of the density of functional groups on the nanoparticles surface often is required in view of steric considerations.

The method embodiments described herein have several features that contribute to their unexpected superiority over methods traditionally used in the art. In some embodiments, methods of making functional gold nanoparticles that are water-soluble and contain tailored reactive group densities for use as chemical reagents can involve leveraging the properties of ligand precursors tailored to allow precise control over final particle diameter. With such embodiments, changing the reduction potential of a gold nanoparticle precursor prior to making the gold nanoparticles can allow for precise control of final nanoparticle diameter in tandem with nanoparticle functionality. This particular parameter has no effect on size when traditional thiol ligands are used.

In yet additional embodiments, methods using flow synthesis, such as mesofluidic flow synthesis, allow for precise control over final particle diameter and polydispersity while simultaneously defining the ratio of ligands on the particle surface affording functional materials in a single step. In such embodiments, the mixing conditions within a flow reactor can be controlled such that precisely defined core diameters with low polydispersity are made. The gold nanoparticles made using the methods disclosed herein also exhibit superior polydispersity, solubility, reactivity, and other properties in comparison to gold nanoparticles made using traditional methods. In some embodiments, disclosed methods can be combined with particular characterization techniques to characterize the gold nanoparticles as they exist in the environments in which they are made, stored, or used (e.g., in solution or in situ).

Also disclosed herein are embodiments of nanoparticles that can be modified using "click" chemistry. In some embodiments, readily prepared modular reagents can be made, with such reagents having appropriate functionality compatible with a wide range of synthetic conditions. The method embodiments disclosed herein allow for the one-step functionalization of the gold core with various types of ligands that can lend solubility and stability to the gold nanoparticle, along with clickable functional groups that can be used in subsequent coupling reactions.

Also disclosed herein are embodiments of kits and combinations comprising, consisting essentially of, or consisting of the gold nanoparticles.

I. EXPLANATION OF TERMS AND ABBREVIATIONS

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

The devices and methods described herein should not be construed as limiting in any way. Instead, the present disclosure is directed toward all novel and non-obvious features and aspects of the various disclosed embodiments, alone and in various combinations and sub-combinations with one another. The disclosed devices and methods are not limited to any specific aspect or feature or combinations thereof, nor do the disclosed devices and methods require that any one or more specific advantages be present or problems be solved. Any theories of operation are to facilitate explanation, but the disclosed devices and methods are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed devices and methods can be used in conjunction with other devices and methods. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or devices are referred to as "lowest," "best," "minimum," or the like. It will be appreciated that such descriptions are intended to indicate that a selection among many used functional alternatives can be made, and such selections need not be better, smaller, or otherwise preferable to other selections.

Examples are described with reference to directions indicated as "above," "below," "upper," "lower," and the like. These terms are used for convenient description, but do not imply any particular spatial orientation.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided:

Alkyl: A saturated monovalent hydrocarbon having at least one carbon atom up to 50 carbon atoms, such as one to 25 carbon atoms, or one to ten carbon atoms, wherein the saturated monovalent hydrocarbon can be derived from removing one hydrogen atom from one carbon atom of a parent compound. An alkyl group can be branched, straight-chain, or cyclic.

Alkenyl: An unsaturated monovalent hydrocarbon having at least two carbon atoms up to 50 carbon atoms, such as two to 25 carbon atoms, or two to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic, cis, or trans (e.g., E or Z).

Alkynyl: An unsaturated monovalent hydrocarbon having at least two carbon atoms up to 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic.

Aryl: An aromatic carbocyclic group comprising at least five carbon atoms up to 15 carbon atoms, such as five to ten carbon atoms, having a single ring or multiple condensed rings, which condensed rings can be (but need not be) aromatic provided that the point of attachment is through an atom of the aromatic aryl group.

Click Chemistry: Chemical synthetic methods for making compounds using reagents that can be joined together using efficient reagent conditions and that can be performed in benign solvents or solvents that can be removed or extracted using facile methods, such as evaporation, extraction, or distillation. In an independent embodiment, click chemistry encompasses [3+2] cycloadditions, thiol-ene reactions, Diels-Alder reactions, inverse electron demand Diels-Alder reactions, [4+1] cycloadditions, nucleophilic substitution of small, strained rings (e.g., epoxide, aziridine, or the like), dihydroxylations, or combinations thereof.

Clickable Functional Group: A functional group that can be used in click chemistry to form a product. In an independent embodiment, a clickable functional group can be selected from, but not limited to, an azide or an alkyne.

Detectable Label: A functional group or other chemical moiety that is attached directly or indirectly to a nanoparticle disclosed herein to facilitate detection of that nanoparticle. Detection can include, but is not limited to, visual detection using the naked eye, analytical detection using instrumentation (e.g., fluorometer, mass spectrometry, chromatography, and the like), or any combination thereof.

Dispersity: A measure of the heterogeneity of particle sizes in a population of particles. The nanoparticles of the present disclosure are considered monodisperse if they have the same core diameter or a narrow core diameter distribution (e.g., a core diameter distribution ranging from 1% to less than 15%, such as 1% to 10%, or 1% to 5%). Some embodiments of the disclosed nanoparticles can be polydisperse if they have a core diameter size distribution greater than 15%, such as 16% to 50%, 16% to 30%, or 16% to 25%. The core diameter distribution percentage can be determined using the following formula: (one standard deviation of the core diameter distribution/average core diameter)*100.

Enzyme-reactive moiety: A moiety that is capable of being converted to a different chemical species upon exposure to an enzyme.

Feed Ratio: A ratio at which two or more ligands (or compositions thereof) are introduced into a flow reactor as disclosed herein. In an independent embodiment, the feed ratio is a measurement of the percentage of a first ligand species that is present in a ligand precursor composition in comparison to a percentage of a second, different ligand species (e.g., % first ligand to % second ligand).

Functionalization Ratio: The ratio at which two or more ligands are coupled to a gold nanoparticle. In an independent embodiment, the functionalization ratio is a measurement of the percentage of a first ligand species that is bound to the gold nanoparticle in comparison to the percentage of a second, different ligand species that is bound to the gold nanoparticle.

Flow Reactor: A chemical reactor capable of being used for flow chemistry wherein a chemical reaction is carried out by conducting fluid as a continuous or intermittent stream through at least one channel into which one or more reagents can be added. In some embodiments, a flow reactor may be a microfluidic reactor, a mesofluidic reactor, or a microfluidic or mesofluidic reactor in parallel and/or under continuous flow to produce large-scale amounts of the nanoparticles (e.g., up to a ton scale size).

Fluorophore: A functional group, or portion, of a molecule that causes the molecule to fluoresce when exposed to an excitation source. The term "fluorophore" also is used to refer to fluorescent compounds used as dyes.

Heteroalkyl/Heteroalkenyl/Heteroalkynyl: An alkyl, alkenyl, or alkynyl group comprising at least one heteroatom to six heteroatoms, such as one to four heteroatoms, which can be selected from, but not limited to oxygen, nitrogen, sulfur, selenium, phosphorous, and oxidized forms thereof within the group. These groups can be branched, straight-chained, or cyclic.

Heteroaryl: An aryl group comprising at least one heteroatom, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Heterocyclyl: A ring system comprising at least one saturated or unsaturated ring comprising at least one heteroatom to six heteroatoms, such as one heteroatom to four heteroatoms, selected from oxygen, nitrogen, sulfur, selenium, phosphorous, and 15 oxidized forms thereof, and comprising at least one carbon atom to 20 carbon atoms, such as one carbon atom to 15 carbon atoms, or one carbon atom to 10 carbon atoms. These groups encompass, for example, a saturated heterocyclyl fused with one or more aromatic hydrocarbons or heteroaryl groups.

Ligand: A molecule (or ion thereof) that binds to a nanoparticle to form a complex.

Nanoparticle: A nanoscale particle with a size that is measured in nanometers, for example, a nanoscopic particle that has at least one dimension of less than about 100 nm.

Precursor: A compound or composition thereof that participates in a chemical reaction to form another compound.

Reynolds number: A calculated quantity, which can be used to estimate, the state of a fluid flow. In some embodiments, the Reynolds number is the ratio of the momentum of the moving fluid to the viscous forces present in a system, which can be used to help predict similar flow patterns in different fluid flow situations. In some embodiments, this term refers to the ratio of inertial forces to viscous forces and quantifies the relative influence of these two types of forces on given flow conditions. In some embodiments, the Reynolds number can be calculated by using the mean flow velocity multiplied by the hydraulic diameter both divided by the kinematic viscosity of the fluid.

Soluble: Capable of becoming molecularly or ionically dispersed in a solvent to form a homogeneous solution.

Water-soluble moiety: A moiety, such as a functional group, that is sufficiently polar so as to be soluble, or impart solubility in water.

Abbreviations:
AuNPs: gold nanoparticles
XPS: x-ray photoelectron spectroscopy
TGA: thermogravimetric analysis
SAXS: small angle x-ray scattering
TEM: transmission electron microscopy
FEP: fluorinated ethylene propylene
MEEE: 2-[2-(2-mercaptoethyoxy)ethoxy]ethanol
MEE: 2-(2-mercaptoethoxyl)ethanol
MHA: 6-mercaptohexanoic acid

II. GOLD NANOPARTICLES

The gold nanoparticles disclosed herein exhibit surprising and unexpected properties that are not obtained using traditional nanoparticle synthesis methods known in the art. For example, the gold nanoparticles disclosed herein exhibit superior polydispersity, solubility, reactivity, and other properties in comparison to gold nanoparticles made using traditional methods.

Certain embodiments of the gold nanoparticles disclosed herein can comprise (a) one or more ligands attached to the gold nanoparticle through a sulfur atom generated from a thiosulfate moiety, (b) a polar linker group, and (c) a terminal reactive moiety selected from a polar functional group, a clickable functional group, a detectable label, a chelating group, or an enzyme-reactive moiety. In particular disclosed embodiments, the gold nanoparticles can comprise two or more groups of ligands, wherein a first group comprises a first polar linker group and a first terminal reactive moiety, either of which may differ from that of a second (or third, fourth, fifth, etc.) group of ligands.

Ligands precursors that can be used to make the disclosed gold nanoparticles can have a Formula 1.

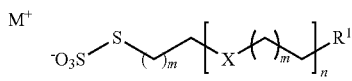

Formula 1

With respect to Formula 1, each X independently can be selected from O, S, or NR$^2$, wherein R$^2$ can be selected from hydrogen, alkyl, alkenyl, alkynyl, or aryl; R$^1$ can be selected from a polar functional group (such as, but not limited to —OH, —N(R$^2$)$_2$, wherein each R$^2$ can be the same or different, —CO$_2$R$^2$, —P(O)(OR$^2$)$_3$, —PO$_4^{-3}$—P(OR$^2$)$_3$, —SO$_4$, or —CH(C(O)N(R$^2$)$_2$)$_2$), a clickable functional group (such as, but not limited to, —N$_3$, or alkynyl), a detectable label (such as, but not limited to, a fluorophore, an enzyme, or a hapten), a chelating group (e.g., a —CH(C(O)N(R$^2$)$_2$)$_2$ group, NHS-esters, N-substituted maleimides, or amines), or an enzyme-reactive moiety (such as an ACE inhibitor selected from lisinopril (N$^2$-[(1S)-1-carboxy-3-phenylpropyl]-L-lysyl-L-proline), enalapril ((2S)-1-[(2S)-2-{[2S)-1-ethoxy-1-oxo-4-phenylbutan-2-yl]amino}propanoyl]pyrrolidine-2-carboxylic acid), captopril ((2S)-1-[(2S)-2-methyl-3-sulfanylpropanoyl]pyrrolidine-2-carboxylic acid), ramipril ((2S,3aS,6aS)-1-[(2S)-2-{[(2S)-1-ethoxy-1-oxo-4-phenylbutan-2-yl]amino}propanoyl]-octahydrocyclopenta[b]pyrrole-2-carboxylic acid), or losartan, (2-butyl-4-chloro-1-{[2'-(1H-tetrazol-5-yl)biphenyl-4-yl]methyl}-1H-imidazol-5-yl)methanol); each m independently can be 0 to 5 (such as 0, 1, 2, 3, 4, or 5); n can be 1 to 10 (such as 1, 2, 3, 4, 5, 6, 7, 8, 9, or 10); and M can be selected from a metal belonging to Group I of the periodic table of elements, such as Li, Na, K, Rb, or Cs. In an independent embodiment, each X can be —CH$_2$.

In some embodiments, the ligand precursor and resulting nanoparticle ligands can comprise a detectable label, such as a fluorophore, an enzyme, a hapten, or combinations thereof. Exemplary fluorophores include, but are not limited to, organic dyes (e.g., fluorescein, fluorescein isothiocyanate, rhodamine, tetramethyl rhodamine isothiocyanate, cyanine, indocarbocyanine, oxacarbocyanine, thiacarbocyanine, merocyanine, dansyl, coumarin, malachite green, or derivatives thereof), biological fluorophores (e.g., allophycocyanin, phycocyanin, phycoerythrin, phycoerythrocyanin, and derivatives thereof), or quantum dots. Exemplary enzymes include, but are not limited to, oxido-reductase enzymes (e.g., horseradish peroxidase), a hydrolase enzyme (e.g., a phosphatase, an esterase, a nuclease, a lipase, a phosphodiesterase, and the like), amplifying enzymes, such as horseradish peroxidase and alkaline phosphatase, and antibodies. Exemplary haptens include, but are not limited to, biotin, streptavidin, digoxigenin, and dinitrophenol.

In exemplary embodiment, the ligand precursor can have a Formula 2, illustrated below.

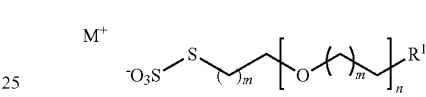

Formula 2

With reference to Formula 2, R$^1$ can be selected from —OH, —CH(C(O)N(R$^2$)$_2$)$_2$, —N(R$^2$)$_2$, —N$_3$, alkynyl, a fluorophore, an acid, an ester, or an ACE inhibitor (e.g., Captopril, Lisinopril, and esters thereof); M can be Na; each m can be 1; and n can be 2 to 4.

In exemplary embodiments, the ligand precursor can be selected from the ligands provided in Table 1.

TABLE 1

Exemplary Ligand Compounds

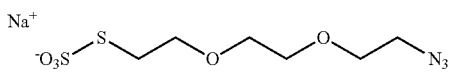

100 sodium S-(2-(2-(2-azidoethoxy)ethoxy)ethyl) sulfurothioate

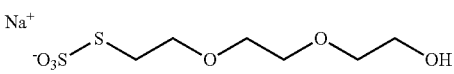

102 sodium S-(2-(2-(2-hydroxyethoxy)ethoxy)ethyl) sulfurothioate

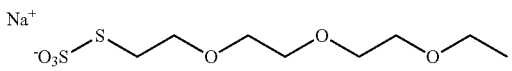

104 sodium S-(2-(2-(2-ethoxyethoxy)ethoxy)ethyl) sulfurothioate

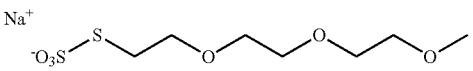

106 sodium S-(2-(2-(2-methoxyethoxy)ethoxy)ethyl) sulfurothioate

TABLE 1-continued

Exemplary Ligand Compounds

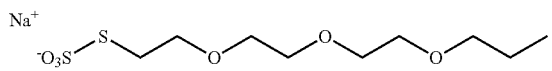

sodium S-(2-(2-(2-propoxyethoxy)ethoxy)ethyl) sulfurothioate

108

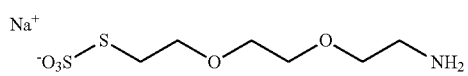

sodium S-(2-(2-(2-aminoethoxy)ethoxy)ethyl) sulfurothioate

110

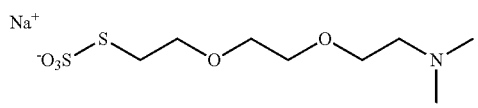

sodium S-(2-(2-(2-(dimethylamino)ethoxy)ethoxy)ethyl) sulfurothioate

112

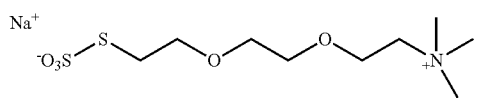

S-(2-(2-(2-(trimethylammonio)ethoxy)ethoxy)ethyl) sulfurothioate, sodium salt

114

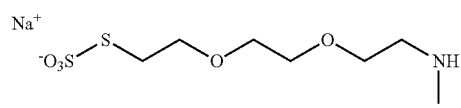

sodium S-(2-(2-(2-(methylamino)ethoxy)ethoxy)ethyl) sulfurothioate

116

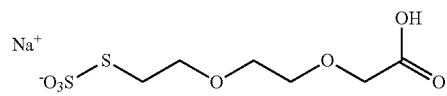

sodium S-(2-(2-(carboxymethoxy)ethoxy)ethyl) sulfurothioate

118

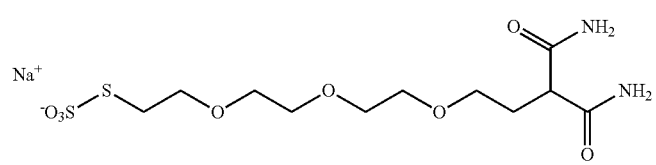

sodium S-(2-(2-(2-(4-amino-3-carbamoyl-4-oxobutyl)ethoxy)ethoxy)ethyl) sulfurothioate

120

TABLE 1-continued

Exemplary Ligand Compounds

122 sodium S-(4-(dimethylcarbamoyl)-2-methyl-3-oxo-7,10,13-trioxa-
2-azapentadecan-15-yl) sulfurothioate

124 sodium S-(12-(diethylcarbamoyl)-14-ethyl-13-oxo-3,6,9-trioxa-14-
azahexadecyl) sulfurothioate

126 sodium S-(12-carbamoyl-14-ethyl-13-oxo-3,6,9-trioxa-14-
azahexadecyl) sulfurothioate

128 sodium S-(12-(dimethylcarbamoyl)-14-ethyl-13-oxo-3,6,9-trioxa-14-
azahexadecyl) sulfurothioate

130 sodium S-(4-carbamoyl-2-methyl-3-oxo-7,10,13-trioxa-2-
azapentadecan-15-yl) sulfurothioate

132 sodium S-(2-(2-(2-amino-2-oxoethoxy)ethoxy)ethyl) sulfurothioate

TABLE 1-continued

Exemplary Ligand Compounds

134: sodium S-(2-(2-(2-(dimethylamino)-2-oxoethoxy)ethoxy)ethyl) sulfurothioate

136: sodium S-(2-(2-hydroxyethoxy)ethyl) sulfurothioate

138: monosodium mono(6-(sulfonatothio)hexanoate)

140: sodium S-(2-(4-(dimethylamino)-3-(dimethylcarbamoyl)-4-oxobutoxy)ethyl) sulfurothioate 142: sodium S-(5-carboxypentyl) sulfurothioate 144: sodium S-(9-(dimethylamino)-8-(dimethylcarbamoyl)-9-oxononyl) sulfurothioate 146: sodium S-((S)-3-((S)-2-carboxypyrrolidin-1-yl)-2-methyl-3-oxopropyl) sulfurothioate TABLE 1-continued Exemplary Ligand Compounds

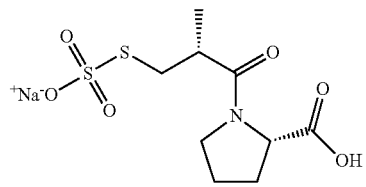

148 sodium S-((R)-3-((S)-2-carboxypyrrolidin-1-yl)-2-methyl-3-oxopropyl) sulfurothioate

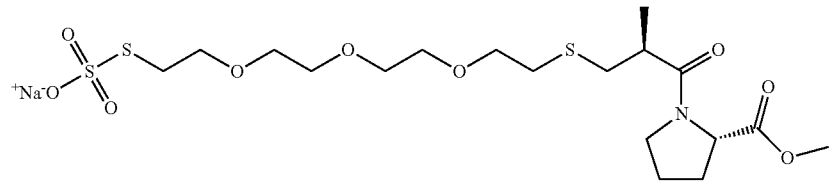

150 sodium S-((S)-15-((S)-2-(methoxycarbonyl)pyrrolidin-1-yl)-14-methyl-15-oxo-3,6,9-trioxa-12-thiapentadecyl) sulfurothioate

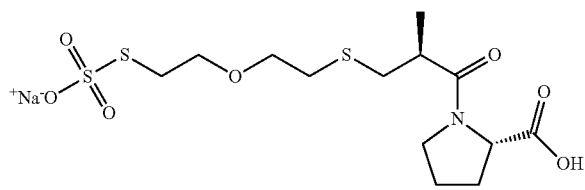

152 sodium S-(2-(2-(((S)-3-((S)-2-carboxypyrrolidin-1-yl)-2-methyl-3-oxopropyl)thio)ethoxy)ethyl) sulfurothioate

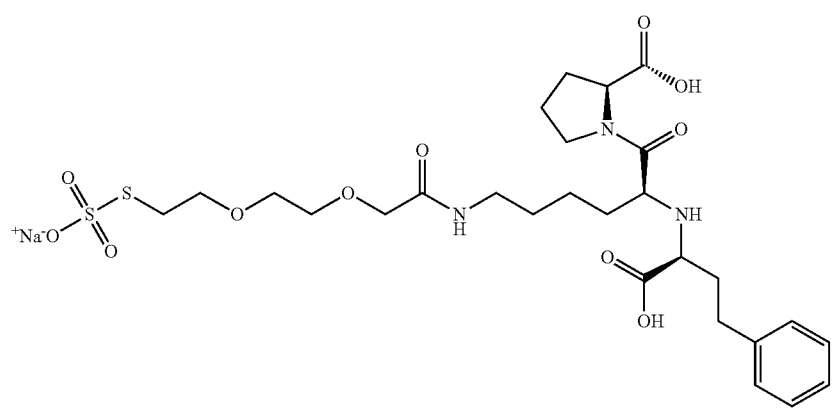

154 sodium S-((14S,16S)-16-carboxy-14-((S)-2-carboxypyrrolidine-1-carbonyl)-8-oxo-18-phenyl-3,6-dioxa-9,15-diazaoctadecyl) sulfurothioate TABLE 1-continued Exemplary Ligand Compounds

158 sodium S-(2-(2-(2-oxo-2-(perfluorophenoxy)ethoxy)ethoxy)ethyl) sulfurothioate

160 sodium S-(2-(2-(prop-2-yn-1-yloxy)ethoxy)ethyl) sulfurothioate

In some embodiments, the core diameter size of the gold nanoparticles disclosed herein can be controlled by selecting any one of the ligand precursors provided above, which comprise a thiosulfate moiety (rather than ligand precursors without these thiosulfate groups, such as thiol-containing ligand precursors and/or disulfide-containing ligand precursors). For example, in some embodiments, using the above-mentioned ligands provides the ability to obtain gold nanoparticles having a core diameter size that can be varied by modifying the pH of a gold nanoparticle precursor solution used to make the gold nanoparticles. The disclosed ligand precursors can weakly passivate the nanoparticle core during nanoparticle growth and still provide strong ligand-nanoparticle couplings (e.g., covalent linkages). In some embodiments, strong passivation can result in inhibition of further growth of the nanoparticle core. Examples of strong passivants include, but are not limited to, thiols, isocyanates, and phosphines. Contrary to such strong passivants, the disclosed ligand precursors can be used to passivate the nanoparticle so that nanoparticle core growth can continue and is not inhibited. In contrast, strong passivants strongly passivate the surface of the gold nanoparticle and are unable to generate nanoparticles with core sizes that vary as a result of pH and instead prevent continued growth of the nanoparticle core. In some embodiments, weak versus strong passivation can be determined by evaluating the nanoparticle core size over a range of pH values; strong passivants will not exhibit changes in core size over a pH range, whereas the weakly passivating ligand precursors disclosed herein will result nanoparticles having varying core sizes over a similar pH range See, for example, FIGS. 1-5, which illustrate results obtained from embodiments wherein thiol- and disulfide-containing ligand precursors were used to make gold nanoparticles. As can be seen from FIGS. 1-5, no size selectivity was observed across a pH range of 3 to 7 for these embodiments. In contrast, FIGS. 6, 7A-7C, 8, 9A-9C, 10, and 11A-11C illustrate results obtained from various gold nanoparticle embodiments disclosed herein wherein ligand precursor compounds meeting Formulas 1 and 2 were used to obtain varying gold nanoparticle core sizes.

Certain embodiments of the gold nanoparticles disclosed herein can have a nanoparticle core diameter ranging from 1.5 nm to 10 nm, such as 2 nm to 10 nm, or 2.5 nm to 8.5 nm, or 2.5 nm to 7 nm, or 3 nm to 7 nm. In exemplary embodiments, the gold nanoparticles can have a core diameter of 2.7 nm, 3 nm, 3.1 nm to 3.9 nm (such as 3.1 nm, 3.2 nm, 3.3 nm, 3.4 nm, 3.5 nm, 3.6 nm, 3.7 nm, 3.8 nm, or 3.9 nm), 4.9 nm, 5.5 nm, and 6.9 nm.

The gold nanoparticles disclosed herein also can have a low polydispersity as compared to gold nanoparticles made using traditional methods known in the art. In some embodiments, the polydispersity of the gold nanoparticles disclosed herein can be greater than 0% to less than 15%, such as greater than 0% to 13%, or greater than 0% to 11%, or greater than 0% to 9%. In some embodiments, the polydispersity can range from 11% to 27%, such as 11% to 19%, or 11% to 15%. In exemplary embodiments, a polydispersity of 11%, 18%, or 27% was obtained. FIGS. 11A-11C illustrate graphs of average diameter and polydispersity obtained by varying the pH of the gold nanoparticle precursor composition disclosed herein during synthesis of the gold nanoparticles.

In some embodiments, the gold nanoparticles comprise at least one ligand selected from the ligands disclosed above. The embodiments disclosed herein are not limited to only one ligand species, as multiple ligand species can be used to provide nanoparticles functionalized with two different ligand species, three different ligand species, four different ligand species, and so on. A multiple number of ligands of each species also is contemplated. In particular disclosed embodiments, the gold nanoparticle can have a mixed ligand system, such as that illustrated by Formula 5.

Formula 5

With respect to Formula 5, each of Ligand 1 and Ligand 2 independently can be obtained from reacting a gold nanoparticle precursor with a ligand precursor meeting Formula 1 or Formula 2. In exemplary embodiments, the gold nanoparticles can include ligands made from any one of the ligand precursor illustrated in Table 1. Variables r and s represent the number of each ligand type present on the nanoparticle and can be numerical values that provide a ratio ranging from 80:20 to 99:1 (r:s). Solely by way of example, if a gold nanoparticle embodiment comprises 100 ligands, then 80 to 99 of the ligands can be Ligand 2 and one to twenty of the ligands can be Ligand 1.

Embodiments of gold nanoparticles comprising a mixed ligand system can comprise a Ligand 1 and a Ligand 2 having similar structural features and/or sizes. For example, gold nanoparticles comprising a mixed ligand system can have a first ligand species that has a polar linker group having particular functional groups and a particular length, and a second ligand species having a polar linker group that is the same, or substantially the same as that of the first ligand species. In exemplary embodiments, the gold nanoparticle can comprise a mixture of ligand species wherein one of the ligand species (e.g., Ligand 2) is an alkylene oxide connected to the nanoparticle through a sulfur atom and the other ligand species (e.g., Ligand 1) is a functionalized alkylene oxide connected to the nanoparticle through a sulfur atom. In some embodiments, the alkylene oxide can be functionalized with a —CH(C(O)N($R^2$)$_2$)$_2$ group, an azide, a carboxyl group, or an alkyne group.

In an independent embodiment, the gold nanoparticle is other than, or is not, any one or more of the following:

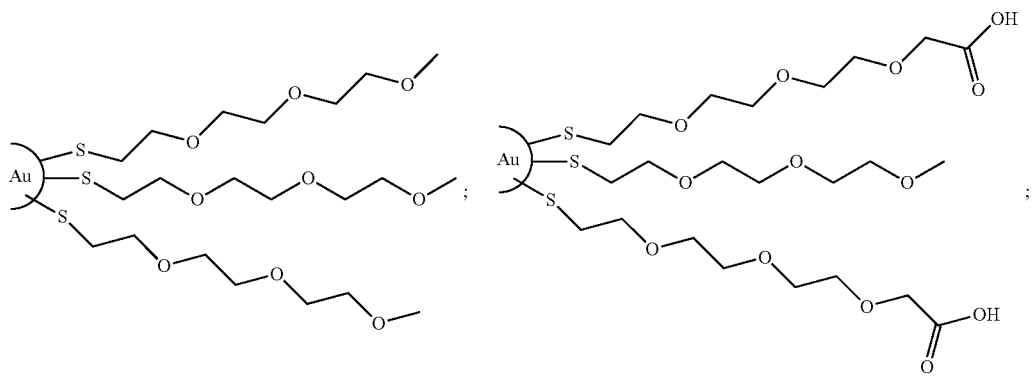

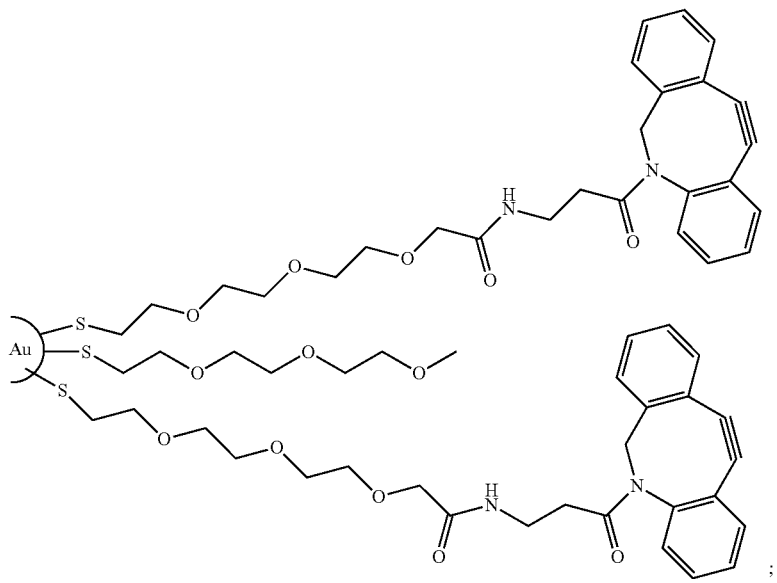

-continued

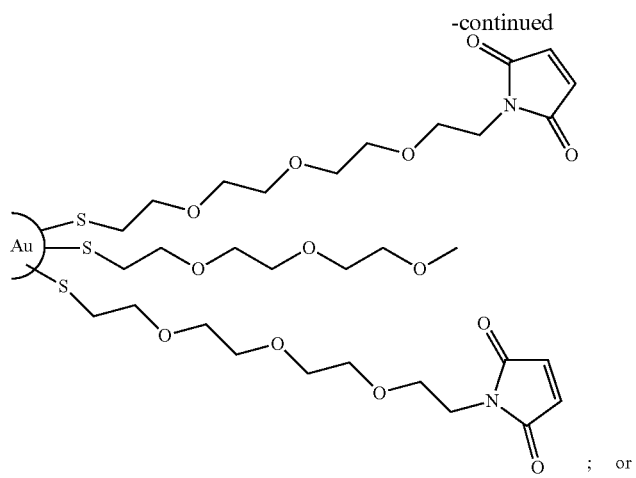

; or

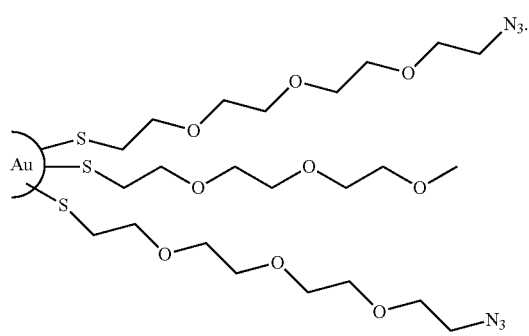

In some embodiments, the gold nanoparticles can have a Formula 6, illustrated below.

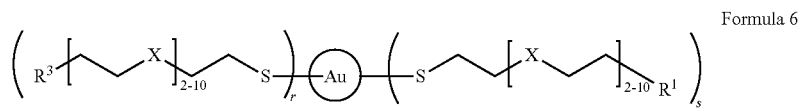

Formula 6

With respect to Formula 6, each X independently can be selected from O, S, or $NR^2$, wherein $R^2$ can be selected from hydrogen, alkyl, alkenyl, alkynyl, or aryl; each of $R^1$ and $R^3$ independently can be selected from a polar functional group (such as, but not limited to $-N(R^2)_2$, $-CO_2R^2$, $-P(O)(OR^2)_3$, $-PO_4^{-3}-P(OR^2)_3$, $-SO_4$, $-CH(C(O)N(R^2)_2)_2$, and the like), a clickable functional group (such as, but not limited to, $-N_3$, alkynyl, and the like), a detectable label (such as, but not limited to, a fluorophore, an enzyme, a hapten, and the like), a chelating group (e.g., $-CH(C(O)N(R^2)_2)_2$), or an enzyme-reactive moiety (such as an ACE inhibitor selected from Lisinopril, Enalapril, Captopril, Ramipril, or Losartan) and typically $R^1$ and $R^3$ are not the same. Variables r and s can be numerical values present in a ratio ranging from 80:20 to 99:1 (r:s). In an independent embodiment, if one of $R^1$ or $R^3$ is an azide, then the other of $R^1$ or $R^3$ is other than, or is not, methoxy.

Exemplary gold nanoparticles are illustrated below.

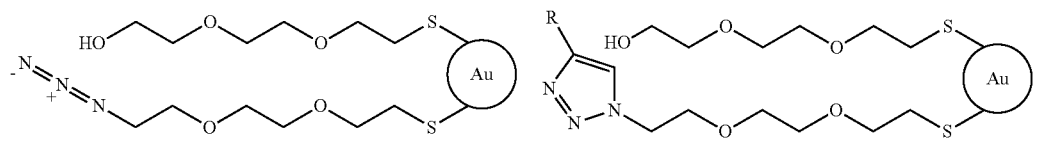

-continued
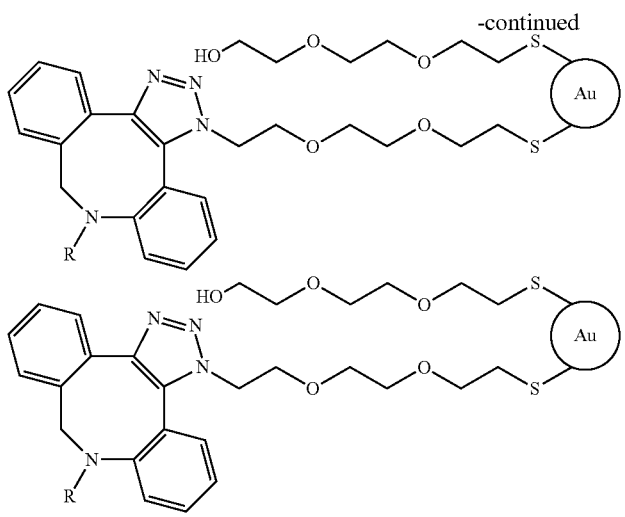
wherein R =
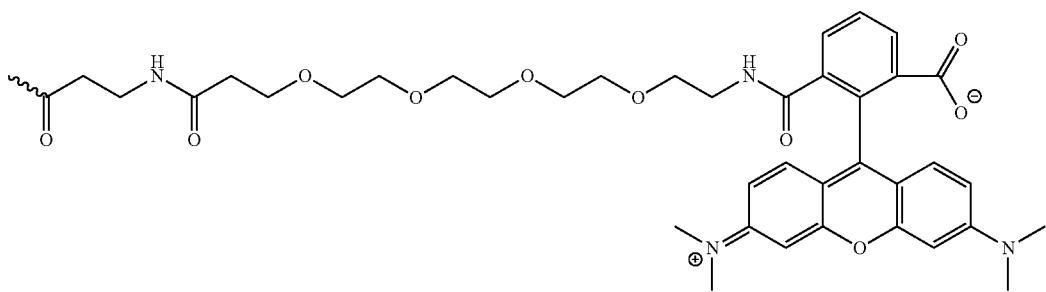
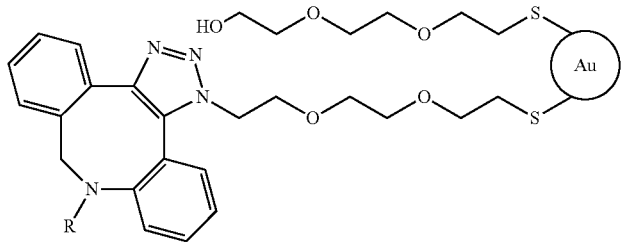
wherein R =
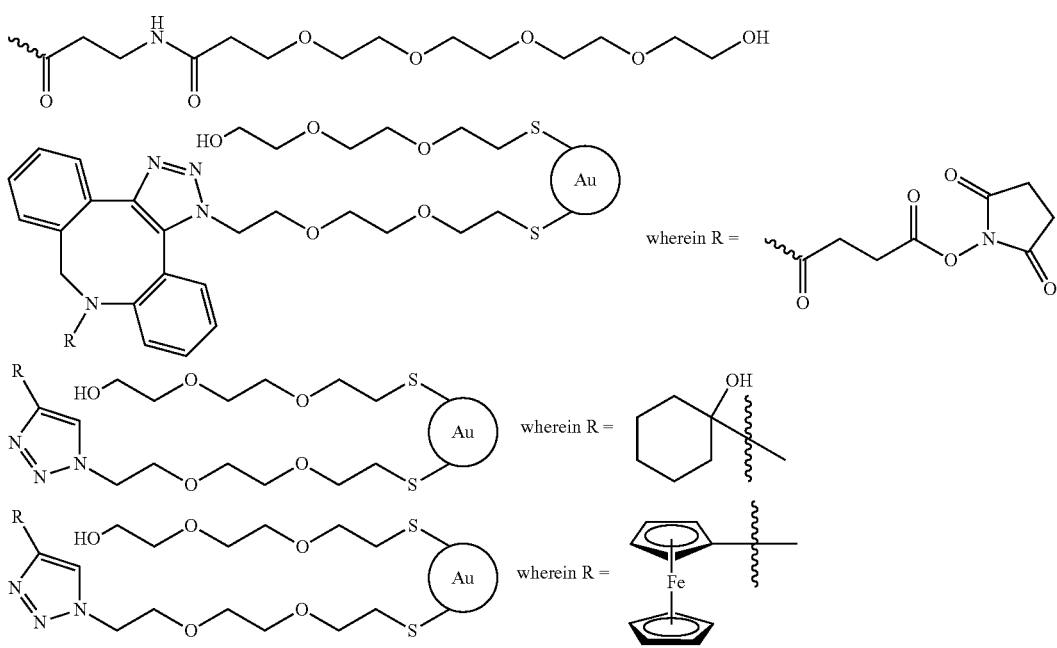

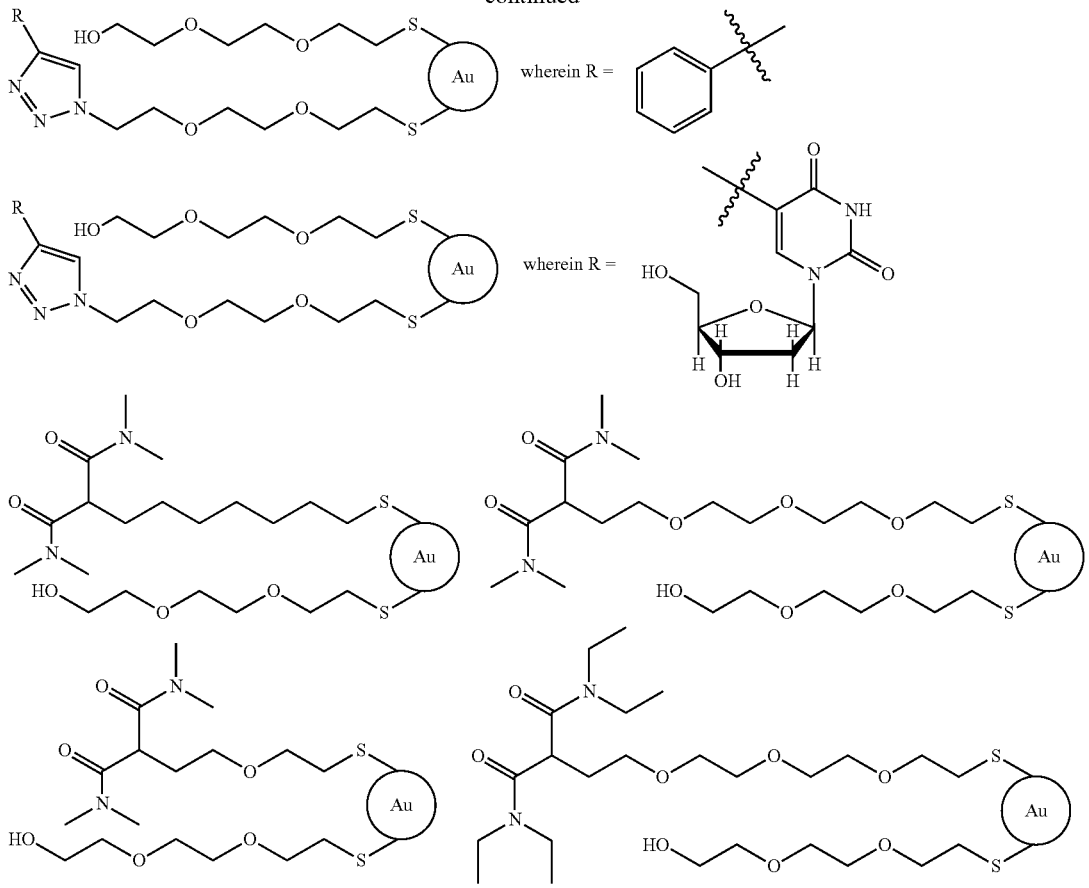

III. METHODS OF MAKING GOLD NANOPARTICLES

Disclosed herein are embodiments of methods of making gold nanoparticles. Embodiments of the methods disclosed herein can be used to make water-soluble gold nanoparticles stabilized with ligands and having core diameters that are difficult to obtain using traditional methods in the art. In some embodiments, the disclosed methods do not require ligand exchange reactions, phase transfer catalysts, or other reagents often required for making water-soluble gold nanoparticles of a desired size and therefore provide an advancement over traditional methods used to make nanoparticles. The methods disclosed herein can be used to make libraries of related gold nanoparticles, thus enabling rapid investigation of structure-function relationships and/or facile synthesis of multifunction gold nanoparticles suitable for use in analytical and/or biomedical applications, as well as other fields.

Method embodiments disclosed herein can be used to make gold nanoparticles having core diameters that can be controlled using a variety of ligand species. Some embodiments of the disclosed methods do not require ligand exchange reactions to provide functionalized, water soluble nanoparticles. Such embodiments can obviate the need for complex reagents, multiple synthetic steps, and also prevent undesired variations in nanoparticle core size, as typically occurs in traditional ligand exchange syntheses. In some embodiments, a working curve can be plotted for ligand precursors used in the disclosed methods of making the nanoparticles. Certain working curve embodiments can be used to identify suitable conditions for making nanoparticles having a specific, targeted core diameter for a variety of ligand precursors. In some embodiments, a working curve can be used to determine synthetic conditions for making a gold nanoparticle having a specific core size for a particular ligand precursor species. An exemplary working curve is illustrated in FIG. 12.

In some embodiments, the methods comprise, consist essentially of, or consist of combining a gold nanoparticle precursor composition, a ligand precursor composition, and a reducing composition. For example, in an independent embodiment, the methods can consist essentially of combining a gold nanoparticle precursor composition, a ligand precursor composition, and a reducing composition and other compositions or components that do not affect the ability to control the core size of the nanoparticle product. For example, such compositions or components could be ligand exchange reaction components (e.g., thiol or thiolate ligands) or exchangeable ligands, such as citrate, phosphine, or amine ligands.

In certain embodiments, the gold nanoparticle precursor composition, the ligand precursor composition, and the reducing composition can be combined in a flow reactor. In some embodiments, the flow reactor can be a batch-wise flow reactor or it can be a continuous flow reactor. In some embodiments, the flow reactor can be a microfluidic flow reactor, a mesofluidic flow reactor, or a microfluidic or mesofluidic reactor in parallel and/or under continuous flow to produce large-scale amounts of the nanoparticles (e.g., up to a ton scale size).

An exemplary method of making the disclosed gold nanoparticles is provided below in Scheme 1. In the embodiments illustrated in Scheme 1, malonamide-containing ligand precursors (or derivatives thereof) can be used to make gold nanoparticles functionalized with such ligands, or mixtures thereof.

Scheme 1

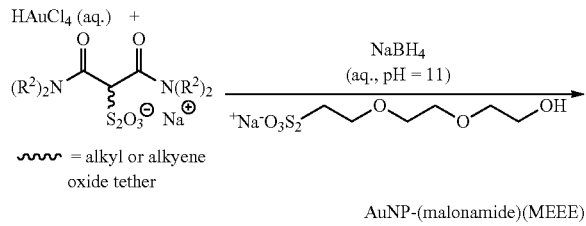

∿∿∿ = alkyl or alkyene oxide tether

AuNP-(malonamide)(MEEE)

In some embodiments, the method can comprise, consist essentially of, or consist of (a) adding a reducing composition comprising a reducing agent into a flow reactor, (b) adding a pre-determined amount of a ligand precursor composition comprising at least one ligand having a thiosulfate terminal functional group, a polar linker, and a reactive moiety into the flow reactor, (c) adding a gold nanoparticle precursor composition having a pH ranging from 2 to 9 and comprising a gold nanoparticle precursor into the flow reactor, and (d) isolating a functionalized gold nanoparticle coupled to at least one ligand of the ligand precursor composition, or a solution thereof. An exemplary schematic illustration of such method embodiments is illustrated in FIG. 13. According to the embodiment illustrated in FIG. 13, a reducing composition 100 is first added to a main flow channel 102 through a side flow channel 104. A ligand precursor composition 106 is then added to the main flow channel 102, through which the reducing composition 100 flows, via a separate side flow channel 108. Once these components have mixed for a sufficient time by flowing through the main flow channel 102, a gold nanoparticle composition 110 is added to the main flow channel 102 through a third side flow channel 112. The reducing composition 100, the ligand precursor composition 106, and the gold nanoparticle composition 110 are then mixed in a container (not illustrated), from which ligand-functionalized gold nanoparticles can be isolated. The compositions used in the disclosed methods, and methods of combining these components, are described in more detail below.

The gold nanoparticle precursor composition can comprise, consist essentially of, or consist of a gold nanoparticle precursor and a base. In embodiments consisting essentially of the gold nanoparticle precursor and the base, the composition can comprise other compositional components that do not reduce the reactivity of the gold nanoparticle precursor, such as a solvent. In some embodiments, gold nanoparticle precursors can have a formula $HAuCl_{4-x}(OH)_x$, wherein X can be 0, 1, 2, 3, or 4. In exemplary embodiments, the gold nanoparticle precursor is $HAuCl_4$. An amount of the gold nanoparticle precursor should be an amount suitable for use in a microfluidic flow reactor, a mesofluidic flow reactor, or a microfluidic or mesofluidic reactor in parallel and/or under continuous flow to produce large-scale amounts of the nanoparticles (e.g., up to a ton scale size). The amount of gold nanoparticle precursor used in some embodiments can be selected so as to control the scale of production and nanoparticle core size as well as to control plating and/or deleterious reactions from occurring during synthesis. In some embodiments, the amount of gold nanoparticle precursor used should be at a concentration that does not decrease the scale of production and/or the size changes observed for the gold nanoparticle core. In some embodiments, the amount of gold nanoparticle precursor used should be at a concentration that is not too high so as to cause plating of gold and/or side reactions between the reagents. In particular disclosed embodiments, the amount of gold nanoparticle precursor used can range from 0.5 mM to 50 mM, such as 1 mM to 25 mM, or 1 mM to 10 mM. In certain embodiments, the gold nanoparticle precursor can be dissolved or suspended in a suitable solvent, such as an aqueous solvent, an organic solvent, or a combination thereof. In exemplary embodiments, the gold nanoparticle precursor can be dissolved or suspended in water.

Without being limited to a particular theory, it is currently believed that modifying the pH of the nanoparticle precursor solution can result in changing (e.g., increasing or decreasing) nanoparticle core diameters, which can correlate with changing speciations of the Au(III) salt from $HAuCl_4$ to $HAuCl_{4-x}(OH)_x$ and finally to $HAu(OH)_4$ as pH increases. In some embodiments, multiple gold species can be present in the composition at different pH values. In certain embodiments, the reduction potential of the Au species can be most positive for the tetrachloro-substituted species and can decrease as each chloride atom of the gold nanoparticle precursor is substituted by a hydroxy ligand. In particular disclosed embodiments, the hydroxy ligands can be replaced with one or more of the ligand precursor compounds disclosed herein. As more chloride atoms are displaced by hydroxyl groups, the rate of reduction can be decreased and thereby increase the final gold nanoparticle core size as ligands precursor compounds are coupled to the nanoparticle.

In some embodiments, a base can be included in the gold nanoparticle precursor composition to modify the pH of the composition and thereby control the gold speciation of the gold nanoparticle formed using the methods, as disclosed above. In some embodiments, the base can be added to change the gold speciation from $HAuCl_4$ to $HAuCl_{4-x}(OH)_x$ wherein X can be 1, 2, 3, or 4. In some embodiments, the core size of the gold nanoparticles made using the disclosed methods can increase in diameter as the pH of the Au(III) solution is modified to be between 2 to 9, such as 3 to 7, or 3 to 5, or 5 to 7, by using a base. The amount of base used in some embodiments can be selected based on the concentration of gold nanoparticle precursor used and can therefore be used to control the speciation of the gold. Suitable amounts of aqueous solutions of known/determined base concentration (e.g., 0.5 M to 1.5 M, such as 0.75 M to 1.25 M, or 1M) can be added to achieve a particular pH. The base can be selected from a base that contains or produces hydroxide (e.g., a base capable of deprotonating water), with some embodiments being inorganic bases or organic bases. In exemplary embodiments, the base can be a metal hydroxide, such as NaOH, LiOH, and KOH. In exemplary embodiments, the gold nanoparticle precursor composition can comprise, consist essentially of, or consist of $HAuCl_4$, NaOH, and water.

In some embodiments, an increase in nanoparticle diameter correlating with a change in pH can be achieved using disclosed method embodiments. In exemplary embodiments, a base can been added to the gold nanoparticle precursor composition to increase an initial pH of 3 to a pH of 5, thereby producing gold nanoparticles having a core size diameter that increases from an initial diameter of 2 nm to a final diameter of 4 nm, such as 2.5 nm to 3.5 nm, or 2.8 nm to 3.5 nm. In other exemplary embodiments, a base can be added to the gold nanoparticle precursor composition to increase an initial pH of 3 or 5 to a pH of 7, thereby producing gold nanoparticles having a core size diameter that increases from an initial diameter of 3 nm to a final diameter of 8 nm, such as 3.5 nm to 7 nm, or 3.5 nm to 6.5 nm. The effect of the gold nanoparticle precursor composition's pH on the size of the resulting gold nanoparticles is illustrated in FIGS. 14A-14G. FIG. 14A illustrates that as the nanoparticle precursor composition pH increases, the average diameter of the gold nanoparticles increase even using various different ligand precursor embodiments. FIGS. 14B-14D are TEM micrographs and FIGS. 14E-14G are corresponding size distribution graphs of an exemplary gold nanoparticle obtained using different pH values for the gold nanoparticle precursor composition.

In some embodiments, ligand precursor compositions can comprise, consist essentially of, or consist of at least one ligand precursor species meeting Formula 1 or Formula 2, provided above. The ligand precursor compositions can further comprise, consist essentially of, or consist of a solvent in which the ligand precursor species may be dissolved or suspended. Suitable solvents include, but are not limited to, aqueous solvents, organic solvents, or combinations thereof. In exemplary embodiments, the solvent can be water. In some embodiments, a single ligand precursor composition can comprise, consist essentially of, or consist of two or more different ligand precursor species, each of which can have a structure meeting Formula 1 or Formula 2.

In some embodiments, multiple ligand precursor compositions can be used wherein each ligand precursor composition comprises, consists essentially of, or consists of a single ligand species meeting any one of Formulas 1 or 2. In other embodiments, a single ligand precursor composition can be used that comprises, consist essentially of, or consists of two or more different ligand species, each of which can meet any one of Formulas 1 or 2. In exemplary embodiments, the ligand precursor composition can comprise, consist essentially of, or consist of two or more ligand precursors as provide in Table 1 and water.

In some embodiments, the ligand precursors used in the ligand precursor compositions can be made using the generic method illustrated below in Scheme 2. According to Scheme 2, a ligand 200 comprising a leaving group, such as a halogen (e.g., chlorine, as illustrated) can be converted to an azide-containing ligand 202 using sodium azide. The other terminus of the ligand can then be converted to a thiosulfate moiety to produce ligand 206 using the method illustrated in Scheme 2.

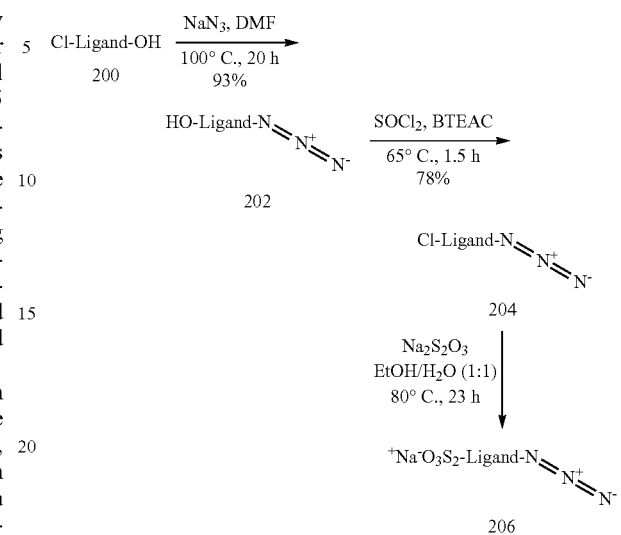

Exemplary embodiments of making the ligand precursors disclosed herein are illustrated below in Schemes 3-5.

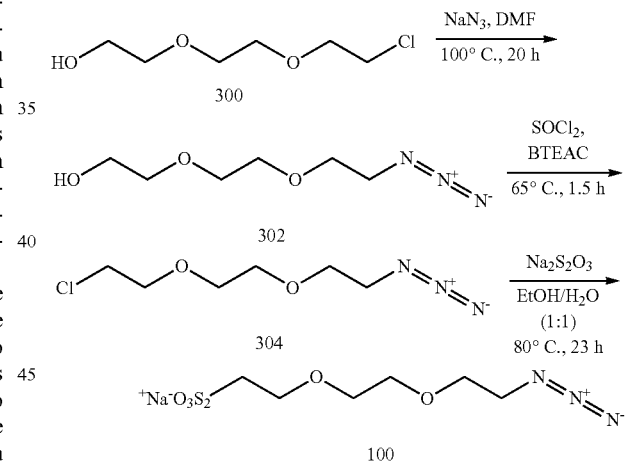

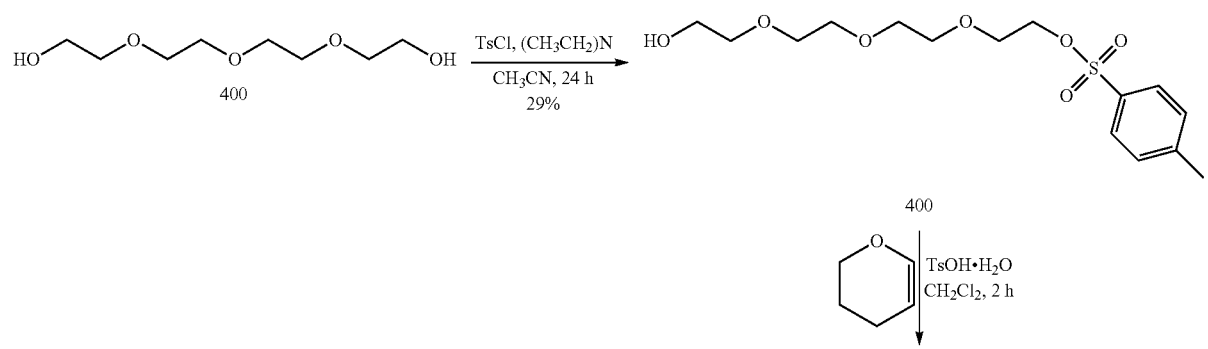

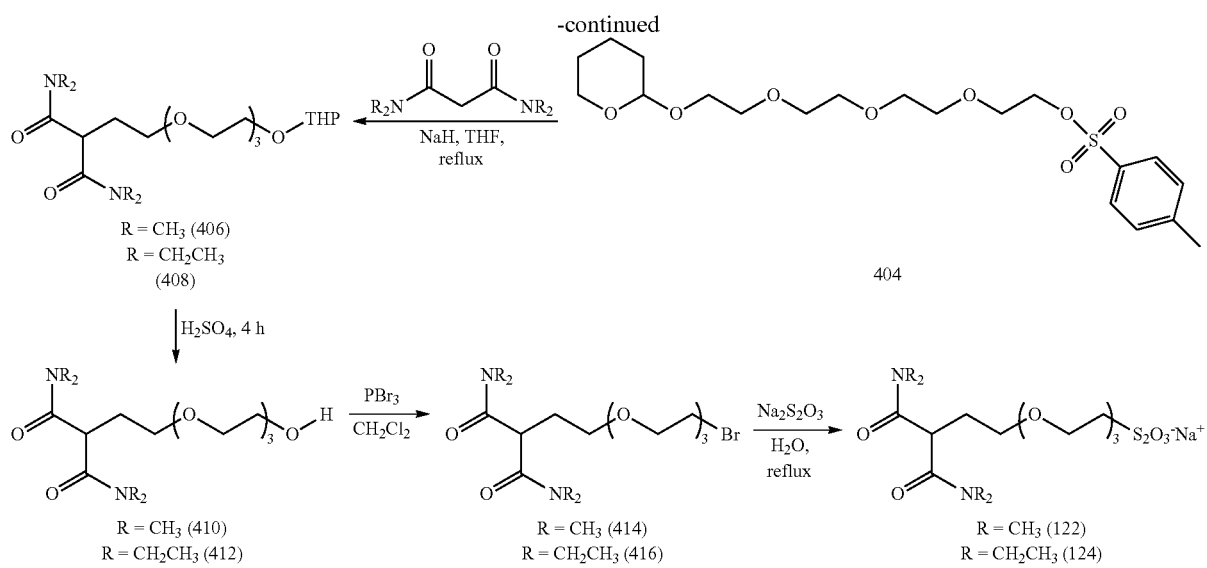

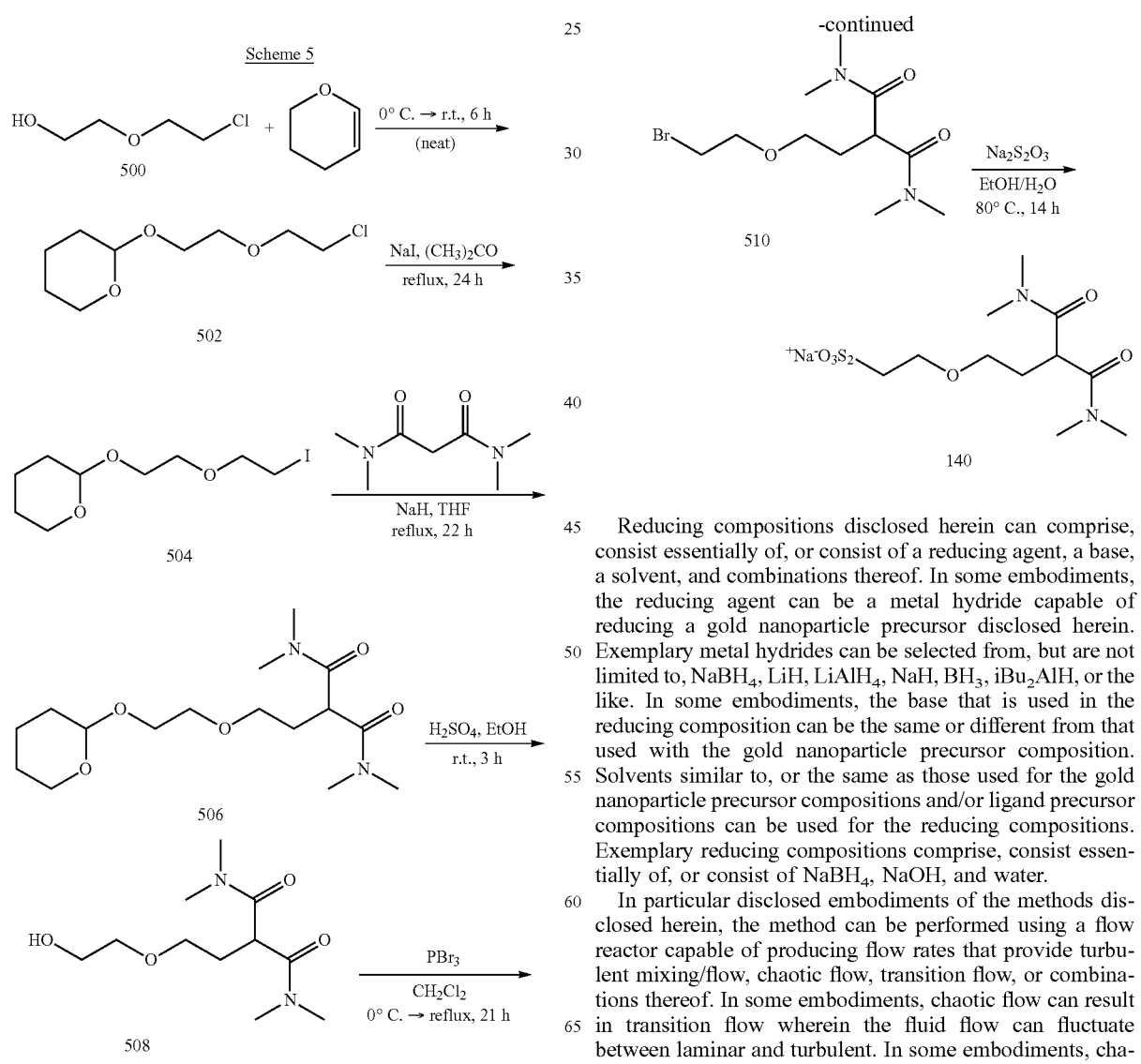

Reducing compositions disclosed herein can comprise, consist essentially of, or consist of a reducing agent, a base, a solvent, and combinations thereof. In some embodiments, the reducing agent can be a metal hydride capable of reducing a gold nanoparticle precursor disclosed herein. Exemplary metal hydrides can be selected from, but are not limited to, $NaBH_4$, $LiH$, $LiAlH_4$, $NaH$, $BH_3$, $iBu_2AlH$, or the like. In some embodiments, the base that is used in the reducing composition can be the same or different from that used with the gold nanoparticle precursor composition. Solvents similar to, or the same as those used for the gold nanoparticle precursor compositions and/or ligand precursor compositions can be used for the reducing compositions. Exemplary reducing compositions comprise, consist essentially of, or consist of $NaBH_4$, $NaOH$, and water.

In particular disclosed embodiments of the methods disclosed herein, the method can be performed using a flow reactor capable of producing flow rates that provide turbulent mixing/flow, chaotic flow, transition flow, or combinations thereof. In some embodiments, chaotic flow can result in transition flow wherein the fluid flow can fluctuate between laminar and turbulent. In some embodiments, chaotic flow, transition flow (or a combination thereof, referred to as transitional chaotic flow) as used herein, can correspond to a Reynolds number that ranges from 40 to 2500, such as 60 to 2000, or 100 to 1500, or 500 to 1000. In particular disclosed embodiments, the Reynolds number ranges from 400 to 2500, with exemplary numbers achieved according to the methods disclosed herein being at least 400, at least 1000, or at least 2300. In some embodiments, mixing times can range $10^{-4}$ seconds to $10^{-2}$ seconds. Rapid mixing can be produced using a high Reynolds number resulting in vortex formation and turbulent flow. In exemplary reactor embodiments described herein a flow rate is used producing Reynolds numbers in excess of 1000 to induce transitional chaotic flow in the flow reactor (e.g., in a container in which all compositions are mixed) and mixing times below $10^{-2}$ seconds.

In some embodiments, the flow reactor can be used to provide a total flow rate of 40 mL/min to 80 mL/min, such as 40 mL/min to 70 mL/min, such as 40 mL/min to 60 mL/min. In exemplary embodiments, the total flow rate through the main channel can be 60 mL/min. Each composition disclosed above can be delivered to a main flow channel through one or more side flow channels that feed the compositions into the main flow channel. In some embodiments, the compositions can be delivered from a container having a suitable dispensing mechanism for allowing the composition to enter the side flow channel and thereby the main flow channel at a particular flow rate. In exemplary embodiments, the reducing composition, the ligand precursor composition, and the gold nanoparticle precursor composition can be added to the flow reactor using syringe pumps or other suitable dispensing mechanism. Suitable flow rates at which the various compositions disclosed herein can be added to the flow reactor can range from 10 mL/min to 40 mL/min, such as 15 mL/min to 35 mL/min, or 15 mL/min to 35 mL/min. In exemplary embodiments, the reducing composition can be dispensed into a side flow channel at a rate of 30 mL/min. In such embodiments, the ligand precursor composition, and the gold nanoparticle precursor composition can be introduced into side flow channels at a rate of 15 mL/min.

In some embodiments, the length of the main flow channel can be modified to provide a particularly desired reaction time during which the compositions can flow through and mix within the main flow channel. For example, the main flow channel length can be increased to provide longer mixing times for compositions flowing there through, or the length can be decreased to reduce the mixing time for compositions. Similarly, the diameter of the main flow channel can be increased to facilitate mixing of increased volumes of the compositions flowing there through, or the diameter can be decreased to reduce the volume of the composition that flows through the main flow channel. Such modifications also can be made to the side flow channels.

In certain disclosed embodiments, the ligand precursor composition(s) can be added to the main flow channel at a particular feed ratio of a first ligand precursor to a second ligand precursor to provide a gold nanoparticle having a functionalization ratio that matches, or substantially matches, the particular feed ratio. For example, a desired functionalization ratio can be incorporated on the surface of the gold nanoparticle by premixing the ligand precursors at a feed ratio that is identical to, or is substantially identical to, the desired functionalization ratio on the nanoparticle surface. In some embodiments, the feed ratio can be that which provides functionalized nanoparticles having solubility properties that lend to their use in analytical and/or in vivo contexts and therefore the feed ratio of a first ligand precursor to a second ligand precursor should be selected to prevent making functionalized gold nanoparticles that are insoluble in such contexts. In some embodiments, the feed ratio should be controlled so that a suitable number of active ligands capable of undergoing further functionalization are present on the gold nanoparticle. Solely by way of example, a feed ratio providing a sufficient number of active ligands comprising a clickable functional group for further functionalization as well as a sufficient number of ligands comprising polar terminal functional groups to promote solubility can be used. In some embodiments, feed ratios ranging from 0:100 (first ligand precursor to second ligand precursor) to 100:0 (first ligand precursor to second ligand precursor) can be used to obtain gold nanoparticles having functionalization ratios ranging from 0:100 to 100:0. In exemplary embodiments, feed ratios ranging from 60:40 to 99:1 (first ligand precursor to second ligand precursor), or 70:30 to 99:1 (first ligand precursor to second ligand precursor), or 80:20 to 99:1 (first ligand precursor to second ligand precursor) can be used.

In some embodiments, the reducing agent and/or the ligand precursor composition can be added to the main flow channel prior to the gold nanoparticle solution to facilitate flow through the main channel. In some embodiments, the reducing agent, the ligand precursor composition, and the gold nanoparticle precursor composition can be added to the main flow channel sequentially, simultaneously, or substantially simultaneously. For example, the reducing agent can be added to the main flow channel, followed by sequential or simultaneous addition of the ligand precursor composition (or a combination of ligand precursor compositions) and the gold nanoparticle precursor composition. In an independent embodiment, the gold nanoparticle precursor composition and the reducing composition are allowed to mix only in the presence of a ligand precursor composition; that is, the gold nanoparticle precursor composition and the reducing composition are not directly mixed in the absence of a ligand precursor composition.

In some embodiments, the method can further comprise characterizing an isolated gold nanoparticle to quantify the isolated gold nanoparticle's core diameter, determine how the gold nanoparticle's core diameter is influenced by reaction conditions (such as the pH of the gold nanoparticle precursor composition) or to determine the shape of the gold nanoparticle. Techniques for characterizing the gold nanoparticle can include, but are not limited to, transmission electron microscopy (TEM), thermogravimetric analysis (TGA), $I_2$-facilitated ligand decomposition and corresponding NMR analysis, and small-angle x-ray scattering (SAXS). In some embodiments, TEM analysis can be performed to determine the shape of the gold nanoparticles, the size of the gold nanoparticle's core diameter, or combinations thereof. In particular disclosed embodiments, SAXS characterization can be used to rapidly analyze the gold nanoparticle's core diameter. Rapid analysis can be obtained within 5 minutes to 5 hours, such as 5 minutes to 3 hours, or 5 minutes to 1 hour. Such rapid analysis can be conducted on a solution of gold nanoparticles and/or an isolated gold nanoparticle and can provide the ability to analyze and characterize nanoparticle core size immediately, or substantially immediately, after the gold nanoparticles are made. In some embodiments, SAXS analysis also can be used to determine polydispersity of the gold nanoparticles. For example, as illustrated in FIG. 14A, a smooth, non-linear trend in gold nanoparticle core size can be observed as the pH of the gold nanoparticle precursor composition is increased from 3 to 7, with a gradual increase in core size from pH 3 to 5 and a more rapid rise in the slope of this trend occurring as the pH is increased above 5.

In some embodiments, the methods can be used to make gold nanoparticles comprising one or more ligands having terminal clickable functional groups that can be used to further functionalize the gold nanoparticle, thereby providing a direct and rapid route to functionalized nanoparticles that otherwise would require ligand exchange reactions to obtain. In some embodiments, the methods disclosed herein can further comprise reacting a gold nanoparticle having a ligand that includes a terminal clickable functional group with a compound comprising a clickable functional group capable of reacting with the clickable functional group of the gold nanoparticle. In exemplary embodiments, the method can comprise reacting a gold nanoparticle comprising a ligand having a terminal azide with a compound comprising a corresponding alkyne functional group capable of undergoing an alkyne-azide cycloaddition with the azide moiety. In other exemplary embodiments, the method can comprise reacting a gold nanoparticle comprising a ligand having an alkyne moiety with a compound comprising a corresponding azide moiety capable of undergoing an alkyne-azide cycloaddition with the alkyne moiety. Suitable alkyne-containing compounds capable of reacting with the gold nanoparticles include, but are not limited to, alkyne-functionalized organometallic compounds, alkyne-functionalized nucleobases (e.g., an alkyne-modified thymidine), alkyne-functionalized fluorophores, alkyne-functionalized phenyl groups, alkyne-functionalized heterocyclic or alicyclic compounds. In other embodiments, the alkyne moiety of these compounds can be replaced with an azide moiety to provide a compound capable of reacting with a gold nanoparticle having alkyne-containing ligands.

IV. METHODS OF USING GOLD NANOPARTICLES

The gold nanoparticles disclosed herein can be used in a variety of applications. In some embodiments, the gold nanoparticles can be used in various biological and/or analytical applications. For example, the gold nanoparticles can be used in colorimetric detection methods as sensors that produce a color change when a particular compound or ion is present. In other embodiments the disclosed gold nanoparticles can be used as drug delivery agents, tissue stains, contrast agents, diagnostic test components, and the like. Exemplary embodiments of using the disclosed gold nanoparticles are provided below.

In some embodiments, the gold nanoparticles can be used as sensors for ion detection. For example, gold nanoparticles comprising one or more chelating groups that can interact with one or more ionic species present in a sample, such as a biological sample or an environmental sample. In exemplary embodiments, gold nanoparticles comprising one or more ligands having a terminal chelating group and one or more ligands comprising a polar functional group can be used to detect the presence of an ionic species, such as a trivalent ionic species. For example, certain gold nanoparticle embodiments comprising a —$CH(C(O)N(R^2)_2)_2$ functional group can be combined with an ionic species, such as $Ln^{3+}$, $Eu^{3+}$, or the like, to form gold nanoparticle chelates capable of producing a color change. In some embodiments, a color change can result from changes in absorption characteristics of aggregated gold nanoparticles relative to single gold nanoparticles. Such changes in absorption can be monitored using UV-visible absorption spectroscopy to analyze compositions of the gold nanoparticles and an ionic species precursor (e.g., $Ln(NO_3)_3$, $Eu(NO_3)_3$, or the like). In some embodiments, a color change occurs when two or more gold nanoparticles chelate the ionic species formed from the ionic species precursor thereby forming gold nanoparticle agglomerates. The agglomerated nanoparticles absorb light at a wavelength different from that of single gold nanoparticles that do not chelate the ionic species. Such absorption changes also can be measured using surface plasmon resonance. In some embodiments, the agglomerated gold nanoparticles absorb light at a wavelength higher than that of single, non-chelated gold nanoparticles. An exemplary detected color change is illustrated in FIG. 15, which illustrates a shift in the wavelength obtained from gold nanoparticles to which an ionic species precursor is added relative to the wavelength from gold nanoparticles not exposed to the ionic species precursor. Chelation of the gold nanoparticles to the ionic species also can be measured using FT-IR spectral analysis to determine the effects of chelation on various functional groups of the chelating group of the gold nanoparticle. An exemplary embodiment is illustrated in FIGS. 16A and 16B, which illustrate shifts in a C=O stretch of diamide groups of an exemplary gold nanoparticle embodiment upon chelation of the ionic species.

In some embodiments, the density of ligands comprising a chelating moiety can be modified to provide gold nanoparticles that strongly sense ionic species and minimize steric crowding of the gold nanoparticle/ionic species chelates, thereby allowing reversible chelation. FIG. 15 illustrates the reversible nature of the gold nanoparticle/ionic species chelation as the addition of a competing chelating species (e.g., EDTA) facilitates transfer of the ionic species from the chelating group of the gold nanoparticle to the competing chelating species.

Embodiments disclosed herein can be used to detect ionic species at concentration levels of 20 nM to 50 μM, such as 30 nM to 40 μM, or 50 nM to 30 μM. In exemplary embodiments, the detection limits ranged from 50 nM to 30 μM In yet other embodiments, the gold nanoparticles can be used for biological applications, such as drug delivery agents, tissue stains, contrast agents, diagnostic test components, and the like. The gold nanoparticles disclosed herein can be used as drug delivery agents to facilitate delivery of a drug to a patient in need of the drug. For example, the gold nanoparticles disclosed herein comprise gold cores that are chemically inert and non-toxic to patients. Additionally, the gold nanoparticles comprise ligands having functional groups that can be coupled to small molecule drugs that can be delivered to a targeted region by injecting the gold nanoparticles at a specific area on the patient, or that can administered systemically by general administration (e.g., oral administration). In some embodiments, ligands present on the gold nanoparticle can be modified to include functional groups that promote the ability of the gold nanoparticle to penetrate cell membranes. The gold nanoparticles also can be used for controlled release of drugs.

In some embodiments, the gold nanoparticles can be coupled with one or more dyes (e.g., colorimetric dyes or fluorescent dyes) via the ligand functional groups disclosed herein. The gold nanoparticles can then be used in a biological assay to facilitate dying of particular samples (e.g., tissues, cells, and the like). Particular regions of the sample can then be visualized and isolated for further testing. The gold nanoparticles also can be used as contrast agents. In some embodiments, the gold nanoparticles can be visualized in a subject in vivo following administration (e.g., oral, intravenous, or subcutaneous administration) using a suitable medical imaging technique (e.g., MRI or ultrasound). In some embodiments, the accumulation of gold nanoparticles in tumors can be effectively imaged using such techniques and can be used to detect tumors or other genetic aberrations.

In some embodiments, the gold nanoparticles can be coupled with one or more of the additional compounds described above using click chemistry for an efficient and economical synthetic conversion. For example, a clickable functional group of a gold nanoparticle can be reacted with a separate compound that has be functional group capable of reacting with the clickable functional group. Exemplary compounds that can be coupled to the gold nanoparticles are illustrated below.

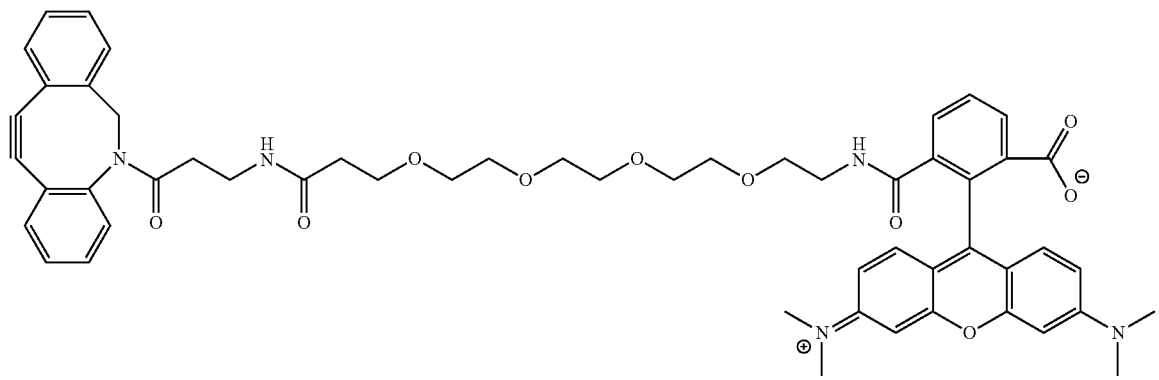

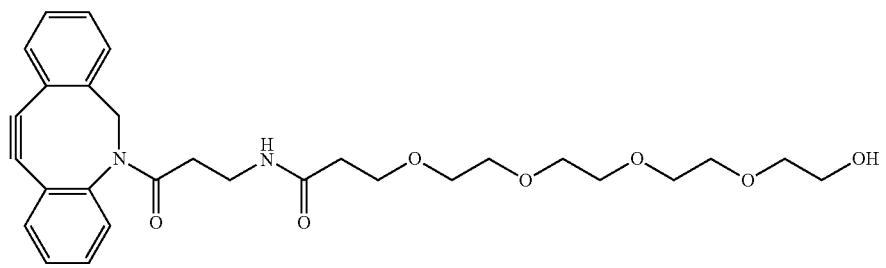

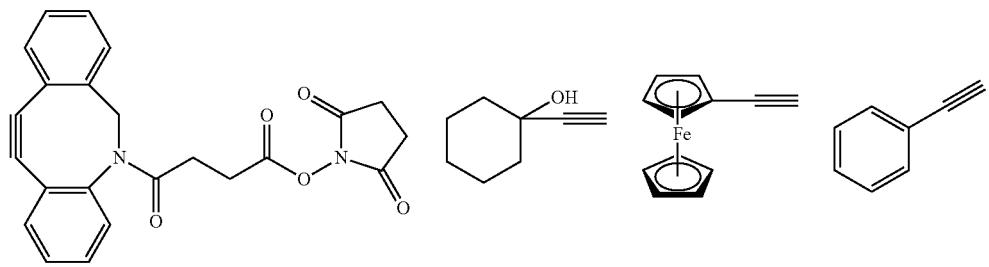

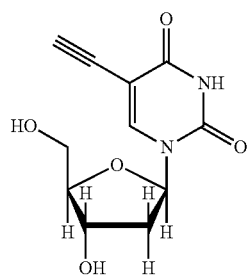

A particular disclosed embodiment of a method of converting a gold nanoparticle embodiment to a functionalized gold nanoparticle using click chemistry is illustrated in Scheme 6.

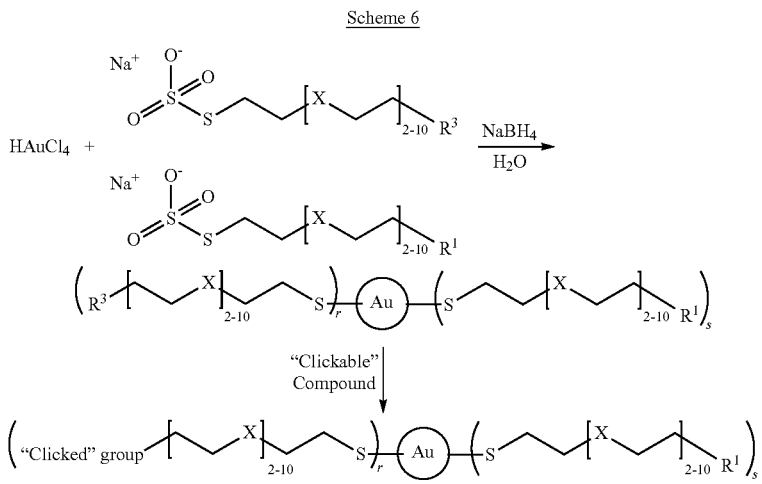

Scheme 6

In an exemplary embodiment, such as that illustrated below in Scheme 7, the gold nanoparticle 700 comprises a clickable azide functional group (obtained from ligand precursor 100) that can react with an alkyne-containing moiety, such as the illustrated cyclic alkyne 702 or a non-cyclic alkyne 704 illustrated in Scheme 7. The two components can react under conditions that promote a cycloaddition between the two components, thereby providing a further functionalized gold nanoparticle. Additional embodiments are illustrated in Schemes 8 and 9.

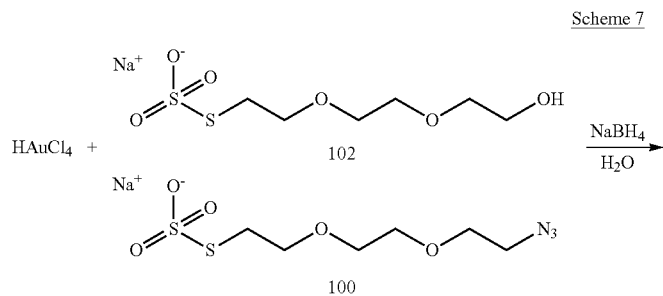

Scheme 7

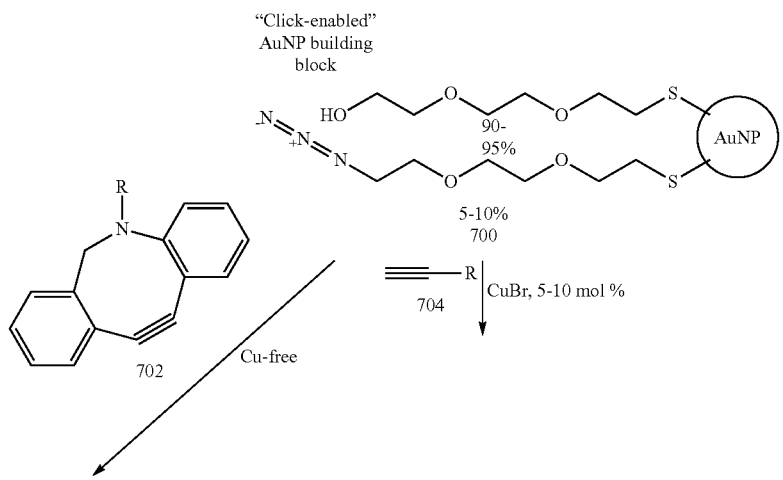

-continued
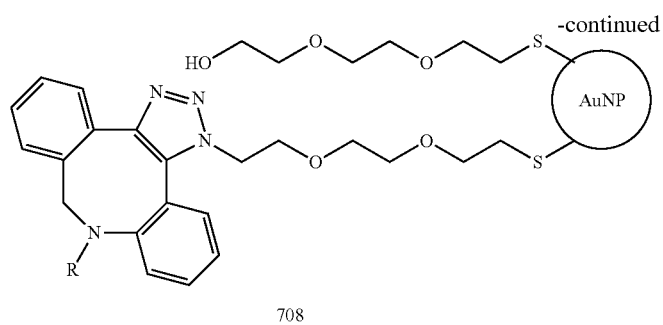
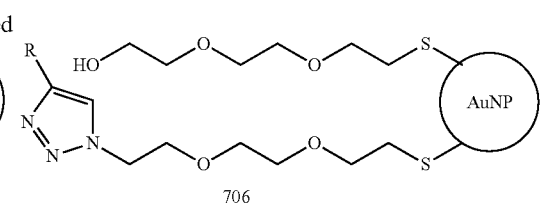
Scheme 8
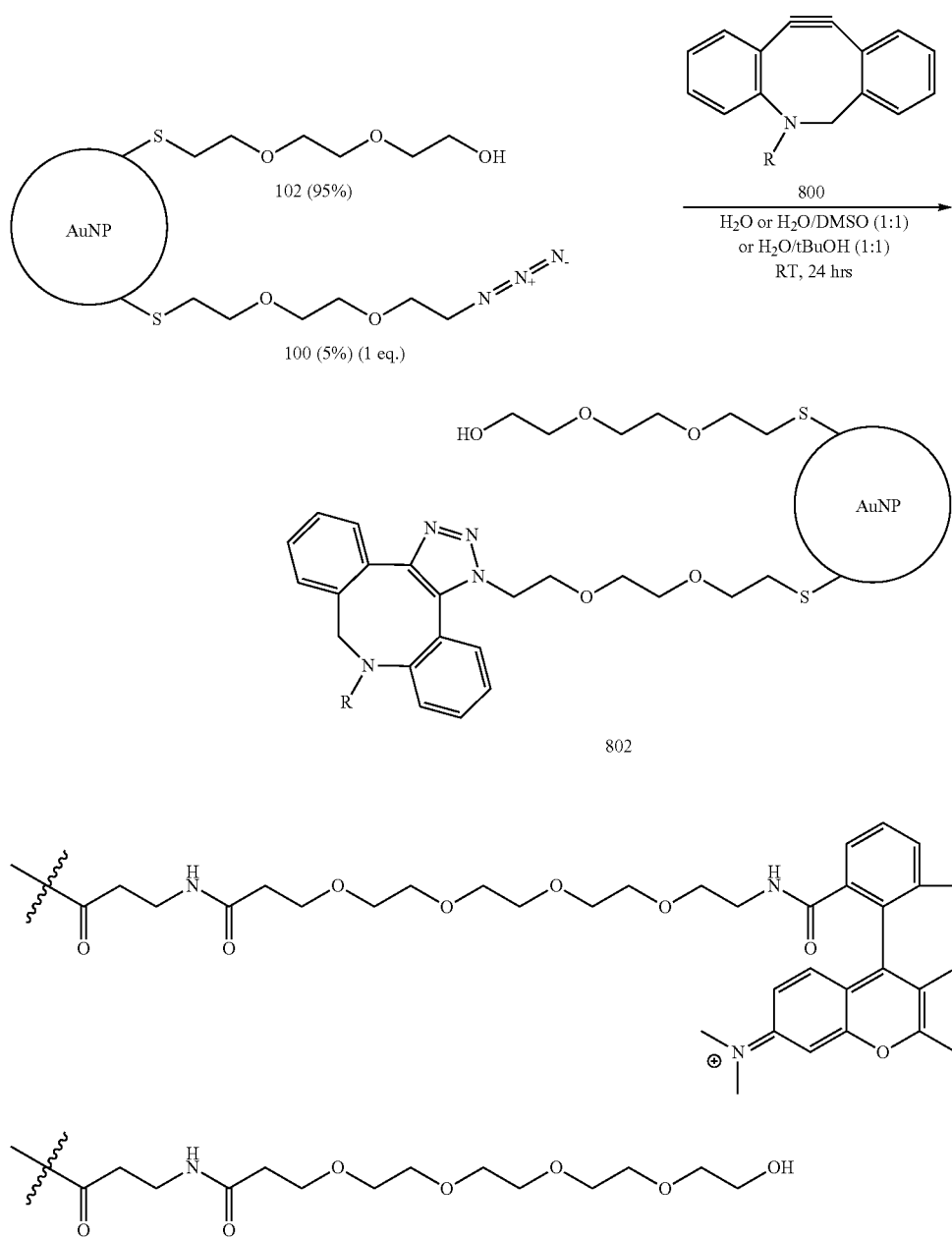

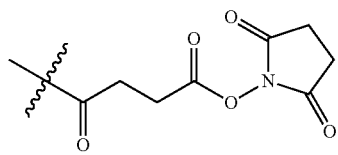

808

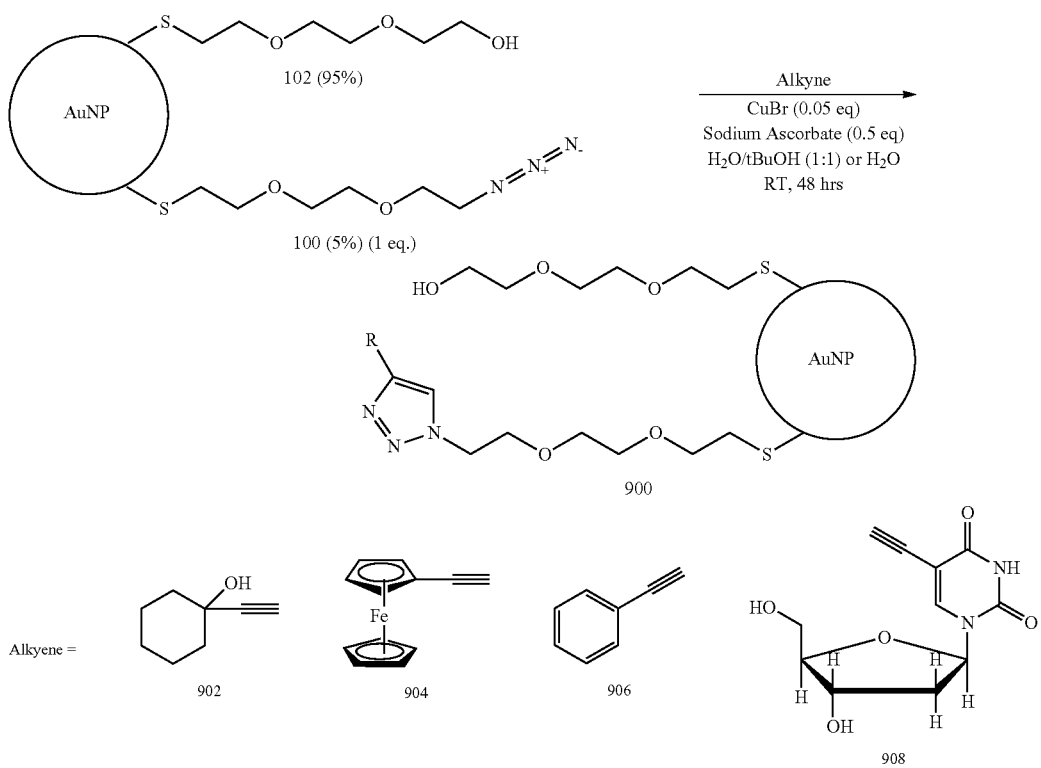

Additional exemplary compounds that can be coupled to the gold nanoparticles using click chemistry are illustrated below.

V. KITS AND COMBINATIONS

Also disclosed herein are kits comprising, consisting essentially of, or consisting of gold nanoparticle embodiments disclosed herein. In embodiments where the kit consists essentially of the gold nanoparticle embodiment, the kit can comprise other components that do not prevent or reduce the reactivity of the gold nanoparticle, such as solvents, synthetic (e.g., not naturally occurring) containers, and additives (e.g., non-naturally occurring and/or naturally occurring preservatives) that help maintain the reactivity of the gold nanoparticle. In some embodiments, the kits can further comprise a container in which one or more gold nanoparticle species can be contained. Gold nanoparticles can be provided in the disclosed kits neat, or they can be provided as a composition, such as with a solvent. Kit embodiments also can comprise, consist essentially of, or consist of a plurality of different gold nanoparticle species, buffers, activating agents, crosslinkers, or combinations thereof. In some embodiments, kits can comprise one or more functionalized gold nanoparticle species wherein one or more ligands of the gold nanoparticle has been reacted with one or more additional compounds as described herein. In some embodiments, kits can comprise one or more gold nanoparticle species, one or more additional compounds capable of reacting with a functional group present on ligands attached to the gold nanoparticle, and optionally one or more reagents capable of facilitating a coupling reaction between the gold nanoparticle and the additional compound(s). Solely by way of example, a kit embodiment can comprise a container housing a gold nanoparticle species comprising one or more ligands having clickable functional groups and one or more additional containers housing compounds (which can be the same or different) comprising functional groups capable of reacting with the clickable functional groups of the gold nanoparticles. An optional container comprising one or more reagents capable of facilitating a coupling reaction between the gold nanoparticle and the additional compounds also can be included in the kit.

Also disclosed herein are combinations comprising or consisting of (a) a gold nanoparticle precursor composition having a pH of 2 to 9 and comprising a gold nanoparticle precursor, (b) a first ligand precursor composition comprising a first ligand having a thiosulfate terminal functional group, a polyethylene linker, and clickable functional group, (c) and a second ligand precursor composition comprising a second ligand having a thiosulfate terminal functional group, a polyethylene linker, and a polar functional group. In some embodiments, the gold nanoparticle precursor composition of the combination can comprise, consist essentially of, or consist of a gold nanoparticle precursor, such as $HAuCl_{4-x}(OH)_x$. In some embodiments, the first ligand precursor composition can comprise, consist essentially of, or consist of the first ligand and a solvent. In some embodiments, the second ligand precursor composition can comprise, consist essentially of, or consist of a second ligand and a solvent. In yet other embodiments, the combination can comprise one ligand precursor composition comprising two different ligand precursors, rather than two different ligand precursor compositions.

VI. EXAMPLES

Materials:

$HAuCl_4 \cdot H_2O$ (99.9%) (Strem); 2-[2-(2-chloroethoxy)-ethoxy]ethanol (99%), sodium borohydride (98%, caplets), Copper(I) bromide (99.999%), 1-ethynyl-1-cyclohexanol (99%), (Aldrich); sodium hydroxide, sodium thiosulfate (anhydrous), (Mallickandrot); sodium L-ascorbate (powder, Bioreagent), dibenzocyclooctyne-PEG4-Flour 545 (DBCO-PEG4-Alexafluor-545), phenylacetylene (98%), ethynylferrocene (97%), (Sigma-Aldrich); thionyl chloride (99.5%) (Acros), sodium azide (95%) (LT. Baker); benzyltriethylammonium chloride (BTEAC, 99%) (TCI America); DBCO-PEG4-OH, DBCO-NHS ester (Click Chemistry Tools); 3,4-dihydro-2H-pyran (97%), p-toluenesulfonic acid monohydrate (98.5%), phosphorus tribromide (99%), sodium thiosulfate pentahydrate (99.5%), sodium borohydride (98%, caplets), sodium hydride (95%, dry), 4-toluenesulfonyl chloride: purified and recrystallized (Aldrich); sodium hydroxide, sodium iodide (Mallickandrot).

$N^1,N^1,N^3,N^3$-tetramethylmalonamide (97%) and $N^1,N^1,N^3,N^3$-tetraethylmalonamide (97%) were obtained from TCI America. 2-(2-(2-(2-hydroxyethoxy)ethoxy)ethoxy)ethyl 4-methylbenzenesulfonate was synthesized according to the method disclosed by Bartz et al., *J. Mater. Chem.*, 1999, 9, 1121-1125, the relevant portion of which is incorporated herein by reference. The Bunte salt analog of 2-(7-mercaptoheptyl)-$N^1,N^1,N^3,N^3$-tetramethylmalonamide (144) was synthesized as follows: Tetramethylmalonamide (TMMA) was first alkylated with n-bromoheptylalcohol to yield the alcohol product, which was brominated using phosphorus tribromide and subsequently converted to the Bunte salt by reaction with thiosulfate. This three-step sequence provided the Bunte salt ligand precursor in an overall 72% yield. The methyl groups on the malonamide enhance water solubility, and the acidic proton at the methylene carbon bridging the two carbonyls in TMMA facilitates synthetic modification by alkylation.

The Bunte salt analog of 2-[2-(2-mercaptoethoxy)-ethoxy]ethanol (102) was synthesized by reacting a starting material with a suitable leaving group (e.g., a chloride) with thiosulfate. See Schemes 2 and 3 for exemplary methods of making this Bunte salt.

Column chromatography was performed using 40-63 μM silia-P flash silica gel (Silicycle). Deionized water (18.2 MΩ·cm) was obtained using a Barnstead Nanopure Diamond system. Flow nanoparticle syntheses were driven using Kloehn syringe pumps (P/N 54022) and Kloehn 10 and 25 mL syringes. The flow system was created using IDEX Teflon tubing (0.75 mm ID, WO#0554152) and Teflon T-mixers. Lengths of tubing were used in assembling the reactor, to keep residence and mixing constant for all flow rates. $^1$H-NMR spectra of the Bunte salts are provided by FIGS. 17A-17C. An exemplary reactor set-up is illustrated schematically in FIG. 47A and photographically in FIG. 47B.

The particular set-up illustrated in FIG. 47 can be modified according to the type of scale at which the gold nanoparticles are produced. Solely by way of example, rather than using the syringes illustrated in FIG. 47, the apparatus could be modified to include a container suitable for housing the needed amount of reducing composition, ligand-precursor composition(s), and gold precursor compositions. Side tubing or other lumens and/or channels can be fluidly associated with the appropriate container and further fluidly coupled to a main flow tube, lumen, and/or channel One or more suitable connectors and/or valves can be used to fluidly coupled the side tubing, lumens, and/or channels to the main flow tube, lumen, and/or channel. The containers comprising the compositions also can include one or more valves and/or connectors that control the flow of each composition into the side tubing, lumens, and/or channels. Valves can be controlled electronically and/or manually. Accordingly, some embodiments of flow reactor can further comprise an electronic circuit and/or computer that can be used to control flow rates and composition introduction timing. The flow path can terminate at a final container that is of sufficient size so as to contain a final volume of the compositions.

Example 1

Methods of making and characterizing gold nanoparticle embodiments are disclosed in this example. The nanoparticle sizes in solution were determined by SAXS. Briefly, AuNP samples were analyzed as synthesized and exposed to monochromated X-rays from a Long Fine Focal spot (LFF) sealed X-ray tube (Cu 1.54 Å) powered by a generator at 2 kW focused by multilayer optics, measured with a Roper CCD in a Kratky camera. The Anton Paar SAXSess, in line collimation mode, was set to average 50 scans of 20 sec for all samples. The corresponding dark current and background scans were subtracted from the data before desmearing was performed using the beam profile in Anton Paar SAXSQuant software. The desmeared data were imported to IGOR Pro (v. 6.22A) software for modeling with 3rd party macros. The size distribution of the sample was determined by using the Modeling II macros in the IRENA package (v. 2.49). The SAXS patterns were fitted using least-squares fitting (LSQF), a size distribution model, a spheroidal form factor (Aspect Ratio=1), a Gaussian distribution, and a dilute system (Structure Factor=1). For each sample, reported polydispersity and average core size values were determined through optimization of volume, mean size, and distribution width values to produce the lowest $\chi 2$ value for the model fit to the data.

Transmission electron microscopy (TEM) was performed on an FEI Tecnai Spirit instrument, operating at 120 kV accelerating voltage. Amine-functionalized $SiO_2$ SMART Grids (Dune Sciences) were used for all TEM analysis. TEM grids were prepared by floating the grid on top of a small droplet of the as-synthesized gold nanoparticle sample for ~30 seconds. After removal from the droplet excess liquid was wicked away using a Kimwipe. TEM images were processed using Fiji software. Gold nanoparticle samples were analyzed by UV/visible spectroscopy (Ocean Optics) for determination of particle concentration and qualitative determination of particle stability. Ligand precursors and final Bunte Salt products were analyzed by $^1$H NMR (300 MHz, Varian). For XPS and TGA analysis, excess ligand and salts were removed from solution by diafiltration using a 75 kDa membrane (Pall). XPS spectra were taken at 20 eV pass energy on a ThermoFisher ESCALab 250 with a monochromated Al K-alpha, using a 400 μm spot size. Spectra were corrected to Au 4f at 84.95 eV. Peak fitting was performed using ThermoFisher Avantage software. TGA measurements were conducted on a TA Instruments Q500 TGA under nitrogen atmosphere. Samples were run from 25° C. to 500° C. at a ramp rate of 10° C./min. Gold nanoparticle samples were prepared by placing ~0.5-2 mg of lyophilized nanoparticles into a tared pan. The sample was then immediately analyzed.

Microreactor Synthesis:

Three syringe pumps each equipped with 3-way distribution valves were purchased from Kloehn (Versa 6, 48k model with rotary valve). All other microreactor components were purchased from IDEX Health and Science. FEP tubing (1/16" outer diameter, 0.030" inner diameter), T-mixers (1/16", 1/4-28, 0.020" Thru, ETFE), 15 psig check valves, and appropriate fittings (1/4-28) and ferrules were assembled with the syringe pumps as shown to enable mesofluidic generation of gold nanoparticles. Tubing and T-mixers were swapped out if material deposition occurred. Solutions were pumped at a total flow rate of 60 mL/min, with tubing lengths selected to allow for sufficient mixing time in the mesofluidic system.

Aqueous solutions were prepared to enable three successive mesofluidic syntheses at each reaction condition. Thus, 30 mL of 5.0 mM HAuCl$_4$, 30 mL of 1.0 mM Bunte Salt ligand, and 60 mL of 1.0 mM NaBH$_4$ were prepared. A total of 0.825 mL of 1.0 M NaOH was added to these solutions, split between the HAuCl$_4$ and NaBH$_4$ solutions. The desired amount of NaOH (ranging from 0.127 mL-0.510 mL) was first added to the HAuCl$_4$ solution, determining the initial Au(III) speciation and effectively controlling the final gold nanoparticle dimensions. Corresponding Au(III) pH values and added volumes of NaOH are summarized in Table 2. The remaining amount of total NaOH (ranging from 0.698 mL-0.315 mL) was added to the NaBH$_4$ solution to maintain final pH of the system. It is advantageous to prepare the HAuCl$_4$ solution first, as it can take up to 20 min to reach equilibrium at high pH. Note that 0.012 mL of additional 1.0 M NaOH was added to the 30 mL of 1.0 mM MHA ligand solution to ensure the acid group was deprotonated at all conditions (a total of 0.837 mL base were added for these syntheses).

Once the appropriate amount of base was added to the respective solutions, each of the three solutions was aspirated by the three syringe pumps as shown in FIG. 13. The 20 mL of NaBH$_4$ solution was dispensed at 30 mL/min, mixed with a stream of 10 mL of ligand solution flowing at 15 mL/min, mixed along a 1.64 m length of tubing (1 second of residence time), before introducing the third stream of 10 mL of Au(III) solution flowing at 15 mL/min. Two simple T-mixers were used to mix the reagents. 15 psig check valves were utilized at each of the 10 mL syringes to avoid backflow. At a total flow rate of 60 mL/min, the final mixed solution is allowed to flow through the reactor for ~2 seconds (~5 m of tubing) before being collected. Small fractions at the beginning and end of each reaction were discarded. The microreactor system was rinsed with nanopure water three times (full aspirate/dispense cycles of the syringe pumps) after each synthesis. Each synthesis was repeated another two times, using the remainder of the prepared solutions, to determine reproducibility. After each set of three syntheses, the downstream T-mixer that introduces the Au(III) solution was replaced with a clean mixer. The used mixers are later cleaned with aqua regia and water to remove any plated Au material left behind. If any plated material was evident in the reactor tubing, it was discarded and replaced with fresh tubing.

TEM Analysis of Gold Nanoparticles:

TEM analysis was performed across the size range for each working curve shown to determine particle morphology. Gold nanoparticles synthesized at all pH values were observed to be spherical. FIGS. 18A-18F provide representative images for each gold nanoparticle working curve, illustrating gold nanoparticles with (a) ligands generated from ligand precursor 142 synthesized at a pH of 3 (FIG. 18A) and pH 7 (FIG. 18B); (b) ligands generated from ligand precursor 136 synthesized at a pH of 3 (FIG. 18C) and pH 7 (FIG. 18D); and (c) ligands generated from ligand precursor 102 synthesized at a pH of 3 (FIG. 18E) and pH 7 (FIG. 18F).

Thermogravimetric Analysis of Gold Nanoparticles:

TGA data were collected to determine the relative coverage of ligand on gold nanoparticles at the extremes of the observed pH range. Beginning and end of ligand mass loss was determined by identifying when the derivative of mass loss vs. temperature had a slope of zero before and after the first major mass loss peak. All values match well to expected values. Graphs of the thermogravimetric data are provided by FIGS. 19A-19F, illustrating results obtained for gold nanoparticles with (a) ligands generated from ligand precursor 136 synthesized at a pH of 3 (FIG. 19A) and pH 7 (FIG. 19B); (b) ligands generated from ligand precursor 102 synthesized at a pH of 3 (FIG. 19C) and pH 7 (FIG. 19D); and (c) ligands generated from ligand precursor 142 synthesized at a pH of 3 (FIG. 19E) and pH 7 (FIG. 19F). Data is also summarized below in Table 3.

TABLE 2

Summary of NaOH volumes added to precursor solutions to tune Au(III) pH and achieve gold nanoparticle size selectivity.

| Au(III) pH | Au(III) pH Abbreviation | 1M NaOH added to HAuCl$_4$ solution (mL) | 1M NaOH added to NaBH$_4$ solution (mL) |
|---|---|---|---|
| 2.97 | ~3 | 0.127 | 0.698 |
| 3.93 | ~4 | 0.225 | 0.6 |
| 4.9 | ~5 | 0.325 | 0.502 |
| 5.87 | ~6 | 0.42 | 0.405 |
| 6.76 | ~7 | 0.51 | 0.315 |

TABLE 3

Comparison of calculated expected mass loss as observed mass loss for thiolate-passivated gold nanoparticles.

| Sample | Expected Mass Loss[a] | Observed Mass Loss |
|---|---|---|
| 136—AuNPs pH ~3 | 10.5% | 11.4% |
| 136—AuNPs pH ~7 | 4.2% | 5.1% |
| 102—AuNPs pH ~3 | 11.9% | 15.8% |
| 102—AuNPs pH ~7 | 6.1% | 6% |

TABLE 3-continued

Comparison of calculated expected mass loss as observed mass loss for thiolate-passivated gold nanoparticles.

| Sample | Expected Mass Loss[a] | Observed Mass Loss |
|---|---|---|
| 142—AuNPs pH ~3 | 13.1% | 13.1% |
| 142—AuNPs pH ~7 | 4.4% | 6.1% |

[a]Expected mass loss calculated for complete thiolate monolayer on AuNP surface X-Ray Photoelectron Spectroscopy:

XPS spectra were collected to ensure that thiolate linkages had been formed on the AuNP surface for AuNPs from each of the working curves. Representative XPS spectra are provided in FIGS. 20A-20C, with FIG. 20A illustrating results for gold nanoparticles having ligands obtained from ligand precursor 136, FIG. 20B illustrating results for gold nanoparticles having ligands obtained from ligand precursor 102, and FIG. 20C illustrating results for gold nanoparticles having ligands obtained from ligand precursor 142. Peaks at ~163 eV correspond to thiolate linkages to the AuNP surface. Peaks observed at ~169 eV correspond to small amounts of oxidized sulfur, either from atmospheric oxidation or residual thiosulfate trapped in the ligand shell. These oxidized peaks comprise less than 10% of the sulfur in all cases.

Determining Au(III) pH Dependence

UV/Visible Spectroscopy.

UV/vis was performed to corroborate other analyses and ensure that particles were stable in solution without flocculation. A plasmon lambda-max shift to higher wavelengths (~500 nm to ~520 nm across the range) as Au(III) solution pH increases was observed in all sample sets, as illustrated by FIGS. 7A-7C. This shift to higher lambda-max corresponds to observed increases in particle diameter by SAXS. Raw SAXS Data. All working curves were based off of modeled SAXS data. Below are representative SAXS patterns for each pH point on the three working curves shown in this embodiment. Data points in these graphs represent raw data while solid traces represent models from which size distributions were determined (FIGS. 9A-9C). Traces are offset for clarity. Nanoparticle core sizes were determined by SAXS for each sample produced for a given ligand across the range of pH from 3 to 7. Smooth working curves through these data were produced using a 3-variable polynomial function. For the following, Equation (1) corresponds to the working curve for ligand precursor 142, while Equations (2) and (3) correspond to the working curves for ligand precursors 136 and 102, respectively:

$$D=0.486(x2)-3.09e-2(x)+7.12 \quad \text{Equation 1}$$

$$D=0.366(x2)-2.26e-2(x)+5.94 \quad \text{Equation 2}$$

$$D=0.0716(x3)-0.722(x2)+2.60(x)-0.410 \quad \text{Equation 3}$$

D represents average AuNP core diameter as determined by SAXS. The value x represents the Au(III) solution pH. Interested readers should note that size trends using other ligands might fit functional forms other than the polynomial fits utilized here. Fitted curves, however, should be smooth with no local minima or maxima between data points. To determine the appropriate amount of NaOH to add to a 30 mL solution of 5.0 mM $HAuCl_4$, a titration using 1.0 M NaOH was performed. Corresponding Au(III) solution pH values for NaOH additions are listed below in Table 4. Working curves were based on AuNP diameter vs. Au(III) solution pH. This titration was used to determine appropriate volumes of NaOH to add to adjust Au(III) solution pH to desired values.

TABLE 4

Titration of 1.0M NaOH into 30 mL of 5.0 mM HAuCl4.

| Volume 1M NaOH (uL) | Au(III) pH |
|---|---|
| 0 | 2.47 |
| 10 | 2.47 |
| 20 | 2.5 |
| 30 | 2.53 |
| 40 | 2.57 |
| 50 | 2.6 |
| 60 | 2.64 |
| 70 | 2.68 |
| 80 | 2.72 |
| 90 | 2.77 |
| 100 | 2.82 |
| 110 | 2.88 |
| 120 | 2.94 |
| 130 | 3 |
| 140 | 3.09 |
| 150 | 3.16 |
| 160 | 3.24 |
| 170 | 3.33 |
| 180 | 3.43 |
| 190 | 3.54 |
| 200 | 3.68 |
| 210 | 3.76 |
| 220 | 3.87 |
| 230 | 3.98 |
| 240 | 4.09 |
| 250 | 4.2 |
| 260 | 4.31 |
| 270 | 4.42 |
| 280 | 4.53 |
| 290 | 4.64 |
| 300 | 4.78 |
| 310 | 4.87 |
| 320 | 4.98 |
| 330 | 5.04 |
| 340 | 5.17 |
| 350 | 5.26 |
| 400 | 5.75 |
| 450 | 6.17 |
| 500 | 6.59 |
| 550 | 7.02 |

Individual Working Curves with Polydispersities.

Here each working curve is shown individually to demonstrate predictive ability and observed polydispersities across the pH range. Working curve data points are solid and predictive data points are open. For each data point, 3 syntheses were performed where corresponding SAXS size analyses were averaged to determine average diameters and standard deviations.

Attempts to Vary Core Size in the Presence of Thiols and Disulfides:

AuNPs were synthesized in flow using a thiol-containing version of ligand precursor 102 across the Au(III) pH range of interest (pH~3-7) to determine if particle core size varied. AuNPs made in the presence of disulfide were only synthesized at extremes of this pH range. The thiol-containing version of ligand precursor 102 was synthesized as follows: 2 molar equivalents of thiourea were added to 1 equivalent of 2-(2-chloroethoxyl)ethanol in 40 mL nanopure water with Ar(g) bubbling through solution. The solution was refluxed for 20 hours, then 20 mL of 5 M KOH was added and the solution was allowed to reflux for another 3 hours. The solution was then brought to pH~1 with HCl. The acidified solution was extracted with chloroform, then the organic layer was extracted with brine solution. Chloroform was removed in vacuo. A 1 mM solution of the thiol-containing version of ligand precursor 102 in sparged nanopure water was used as ligand solution in the described mesofluidic synthesis (See Experimental Details above). This solution was then left open to air at pH=10 for 48 hours to generate a 0.5 mM solution of a disulfide-containing version of ligand precursor 102. A second, 1 mM disulfide solution was also made in this fashion.

Comparison of Batch and Mesofluidic Syntheses

UV/Visible Spectra for AuNPs Across Au(III) pH Range.

UV/vis spectra were collected for each batch of AuNPs produced to determine stability and qualitative size distributions.

SAXS Working Curve for AuNPs Made in Batch.

SAXS data were collected for AuNPs synthesized in 80 mL batches. For each data point, 3 syntheses were performed where corresponding SAXS size analyses were averaged to determine average diameters and standard deviations. Results are illustrated in FIG. 21.

Comparison of Variability in AuNP Core Size for Batch and Flow Syntheses

AuNPs were synthesized in (1) batch reactions performed by a single researcher, (2) batch reactions performed by 3 different researchers, and (3) mesofluidic reactions by multiple researchers. AuNP size distributions were determined by SAXS. Variability in core size is low when a single researcher performs batch syntheses in rapid succession, but rises dramatically when multiple researchers perform these batch syntheses. When syntheses are performed in a microreactor and the same stock solutions are utilized, researcher-dependent variables are eliminated and variability is much lower than for reactions performed in batch. Mesofluidic reactions performed by single or multiple researchers yield consistent results between syntheses.

Corroboration of AuNP Size Distributions by TEM and SAXS

AuNPs functionalized with ligands derived from ligand precursor 102 made using the mesofluidic reactor at Au(III) solution pH of 3, 5 and 7 were analyzed by SAXS and TEM. SAXS provides a volume weighted size distribution while TEM provides a number weighted size distribution. The calculated mean diameter was determined by using the mean and polydispersity as determined by SAXS. The number weighted mean particle diameter was then determined by image analysis of multiple TEM micrographs with 2605, 2251, and 1201 particles analyzed for samples synthesized at pH 3, 5 and 7 respectively. Results are also summarized below in Table 5.

TABLE 5

Gold Nanoparticle Size Distributions

| Au(III) pH | AuNP Diameter (nm) by SAXS | PolyDispersity by SAXS | Diameter (nm) Converted to Number Distribution (Calculated) | AuNP Diameter (nm) by TEM |
|---|---|---|---|---|
| 3 | 2.8 | 18% | 2.6 | 2.7 |
| 5 | 3.5 | 11% | 3.3 | 3.3 |
| 7 | 6.3 | 27% | 4.6 | 5.5 |

Specifically functionalized AuNPs with core sizes ranging from 2 to 10 nm can be easily prepared using the embodiments disclosed in this example. AuNPs were synthesized with three different Bunte salt ligands in batch conditions. A Bunte salt, $HAuCl_4$ and $NaBH_4$ were combined (in a 1:5:2 ratio) in a round bottom flask stirred at moderate speed. In particular embodiments, $NaBH_4$ was added to the flask first, followed by Bunte salt solution, and finally $HAuCl_4$. Prior to addition, NaOH was added to both the $HAuCl_4$ and $NaBH_4$ solutions. The base added to the $HAuCl_4$ solution can control the Au(III) speciation and thus can influence AuNP size. Base was added to the $NaBH_4$ solution to maintain the same final pH between batches.

Increasing the pH of the Au(III) solution produced larger particles as indicated by a shift in the plasmon λ-max in the UV/visible spectra (FIGS. 7A-7C). There appeared to be differences in the AuNP size dependence on pH when using different Bunte salt ligands, but the qualitative nature of optical spectroscopy and batch-to-batch variation precluded drawing definitive conclusions.

When different researchers performed these syntheses, the variation in core size was as high as 18% (Table 6). Without being limited to a single theory of operation, it is currently believed that this variation occurs because the rate nanoparticle formation is similar to that of mixing and is, thus, significantly influenced by variations in mixing rate. In some embodiments, this variation was reduced by implementing flow based syntheses to reduce polydispersity and improve reproducibility between batches. To achieve more effective mixing and a reasonable throughput for synthesis, T-mixers with inner diameters of 500 microns were used. In some embodiments, a microfluidic reactor can be used. In this example, however, the high flow rates, and thus Reynolds numbers, utilized suggest the reactor is operating under mesofluidic conditions. The use of the mesofluidic reactor described herein to control reagent addition and mixing rates significantly reduced variation between batches, to less than 2%, even when performed by different researchers.

TABLE 6

Determination of Gold Nanoparticle Core Size

| Synthetic Method | SAXS AuNP Diamter (nm) | Diameter Standard Deviation |
|---|---|---|
| Single Researcher Batch Syntheses | A) 7.77 B) 7.45 C) 8.22 | 5% |
| Multiple Researcher Batch Syntheses | A) 7.87 B) 5.71 C) 8.17 | 18% |
| Mesofluidic Syntheses | A) 5.73 B) 5.88 C) 5.92 | 2% |

Syntheses were performed in the mesofluidic reactor at a flow rate of 60 mL/min using identical reagent ratios as the batch syntheses described above. The solutions were delivered by syringe pumps and mixed in Tefzel T-mixers connected by FEP tubing. To minimize loss of material to plating within the reactor, the flows of borohydride and ligand solutions were initiated prior to introducing the gold salt solution. In particular working embodiments, 8 mL of 5.0 mM $HAuCl_4$, 10 mL of 1.0 mM Bunte Salt ligand, and 20 mL of 1.0 mM $NaBH_4$ were used for a total reaction volume of 38 mL. To control the Au(III) speciation, NaOH was added to achieve a given salt solution pH. An appropriate amount of base was also added to $NaBH_4$ solutions so that the final pH of each reaction was the same.

To quantify how the size depends upon pH, TEM and small-angle x-ray scattering (SAXS) measurements were performed. TEM analysis confirmed that the particles were spherical but proved to be too time-consuming for size determination of the many experimental replicates. In addition, aggregation of gold nanoparticles during TEM sample preparation skews the measured size to larger core sizes, especially for larger core sizes where gold nanoparticle assembly occurs readily upon sample drying. To avoid the possibility of deposition effects and poor statistical significance due to the small number of particles sampled by TEM, SAXS was used for determination of the AuNPs size distribution. A previous comparison of size determination by SAXS and TEM has illustrated that SAXS model fitting is a viable approach to overcome these challenges. The SAXS data were corroborated by TEM size analysis of AuNPs functionalized with ligands obtained from ligand precursor 102 that were synthesized with an Au(III) solution pH of 3, 5, and 7 (FIGS. 14A-14G and Table 5). While analysis of TEM data provides a number-based size distribution, SAXS describes a volume-based distribution. To compare the TEM and SAXS data, the mean diameter determined by SAXS was converted to a number size distribution (Table 5). Diameters measured by SAXS agree well with those from TEM (within 0.1 nm at pH 3 and 5). At pH 7, the somewhat larger polydispersity combined with the presence of aggregates due to TEM sample preparation result in a mean diameter determined by TEM that is slightly larger than the calculated mean from SAXS (Table 5). SAXS analysis made it possible to rapidly (within minutes) analyze the nanoparticles in solution and allowed us to quantify the batch-to-batch variation in AuNP core size. Combining the improvements from mesofluidic reactor and automated SAXS analysis, AuNPs with uniform, reproducible core sizes were rapidly generated (FIGS. 14A-14G).

The method of making the gold nanoparticles described in this embodiment, as well as the other methods disclosed herein, affords the ability to incorporate specific functionality on the AuNP surface while simultaneously maintaining control over core size. The gold nanoparticle size and surface chemistry were characterized using a complementary suite of analytical techniques. Briefly, XPS of the S2p region indicates the ligands are bound as thiolate, while TGA mass loss is consistent with a fully formed monolayer on the gold surface. Collectively these data indicate that the particles are thiolate-stabilized AuNPs. The particles exhibited long term stability in solution as well as stability during diafiltration, lyophilization and resuspension. In some embodiments, the gold nanoparticles were stable for three months or longer. In some working embodiments, 6.25 mg of purified lyophilized nanoparticles were obtained, representing a 73% yield of gold used per batch. In addition, yields can be improved by reclaiming nanoparticles lost through nonspecific adsorption to the diafiltration membrane by flushing the membrane with 0.1 M NaOH.

There is a different dependence of size on the pH for each of the three ligands examined in this embodiment. At the highest pH, under the same reaction conditions, the identity of the ligand produces a change of over 2 nm in the core size. These findings are consistent with previous observations that ligands influence core growth during synthesis. In addition, at the extremes of pH, the dependence of size upon ligand type is reversed. At low pH, ligand precursor 102 produced the largest nanoparticles, whereas at high pH, ligand precursor 142 produced the largest cores. The combination of the ligand and pH effects upon core size makes it impossible to predict a priori what conditions are needed to produce a functionalized AuNP with a defined core size.

Given the smooth trend of particle sizes as a function of pH, it was determined whether a continuous curve drawn through these points (a working curve) could be used to generate AuNPs with targeted core sizes. These are particularly useful when describing complex trends or when mechanistic understanding is limited. Here the curves could be used to predict the pH needed to produce a particle with a specific core size for a selected ligand.

Given the interest in producing functionalized particles with defined core sizes, the utility of the working curve shown for MHA in FIG. 12 was tested by attempting to synthesize 3.0, 5.0, and 7.0 nm functionalized AuNPs. From the working curve, it was determined the appropriate Au(III) solution pH for the targeted core sizes and then synthesized AuNPs at each of these conditions through addition of NaOH to the Au(III) solution (Table 4). Size distributions determined by SAXS show that these syntheses produced AuNPs with diameters of 3.0, 4.9 and 6.9 nm respectively, with <1% average variation in size between three runs. Each synthesis produced core diameters within 3% of targeted value. It was possible to target specific nanoparticle sizes for each of the ligands used. These results suggest that the working curves are descriptive of the trend in AuNP size vs. Au(III) solution pH, and facilitate targeted synthesis of AuNPs across a continuous size range.

The direct synthetic methods disclosed herein utilizes systematic control of Au(III) speciation using a variety of Bunte salt ligands targeting AuNP core sizes while independently tailoring functionality. The present disclosure provides novel methods for making gold nanoparticles that can use Au(III) speciation as a method for controlling the size of covalently-passivated AuNPs. The use of a flow reactor can be used to facilitate rapid, more reproducible syntheses compared to batch reactions while an autosampler-equipped SAXS instrument can be used for rapid analysis of AuNP core size as-synthesized.

Example 2

Synthesis of Mixed Malonamide/Ethylene Glycol Gold Nanoparticles

Mixed monolayer gold nanoparticles were synthesized directly by reduction of $HAuCl_4$ (aq.) in the presence of mixed Bunte salt ligand precursors in a microfluidic reactor using set-ups and reactant conditions as disclosed herein. Aqueous solutions were prepared to enable three successive flow syntheses at each reaction condition. In some working embodiments, 30 mL of 5 mM $HAuCl_4$, 30 mL of 1 mM Bunte salt mixed ligands, and 60 mL of 1 mM $NaBH_4$ were prepared for use in a microfluidic reactor. 1.2 mL of 1 M NaOH was added to the $NaBH_4$ solution. For subsequent characterization and cross-linking experiments, free ligands and unreacted starting materials were removed from nanoparticles produced using diafiltration. Mixed ligand AuNP products with functional ligands obtained from ligand precursors 122, 124, and 144 were diafiltered with 60 volume equivalents of nanopure $H_2O$ (typically 1.8 L) using a 70 KDa membrane (Pall Corporation), whereas AuNPs with ligands obtained from ligand precursor 140 were diafiltered similarly using a 10 KDa membrane.

NMR Spectroscopy of Purified Nanoparticle Samples for Analysis of Purity and of Decomposed Nanoparticles for Quantifying Mixed Ligand Precursor Compositions.

Approximately 50% of the purified nanoparticle solution was lyophilized and redispersed in 0.5 mL deuterated solvent. An initial spectrum was acquired at 500 MHz with 64 scans and a relaxation delay of 1 second to confirm that all free ligands and synthetic byproducts were removed. The absence of sharp peaks (due to free ligands) and the presence of characteristic broad peaks indicated that all of the ligands were bound to the AuNP surface. Quantification of bound mixed ligands was initiated by adding approximately 2 mg of $I_2$ to the NMR tube directly. The mixture was shaken vigorously and allowed to react in ambient conditions for ~10 minutes. AuNP NMR spectra showed that the ligands had been oxidized to form the corresponding disulfides. Integration of peaks attributed to malonamide and of diluent ligand precursor 102 was performed to quantify mixed ligand ratios.

Nanoparticle Core Size Determination Using Small Angle X-Ray Scattering.

Nanoparticle sizes resulting from the direct syntheses performed were determined in solution at synthesis concentrations using small angle X-ray scattering (SAXS). Briefly, NP samples were exposed to monochromated X-rays from a Long Fine Focal spot (LFF) sealed X-ray tube (Cu 1.54 Å) powered by a generator at 2 kW focused by multilayer optics, measured with a Roper CCD in a Kratky camera. The Anton Paar SAXSess, in line collimation mode, was set to average a minimum of 50 scans for 20-40 second exposures. The corresponding dark current and background scans were subtracted from the data before desmearing using the beam profile in Anton Paar SAXSQuant software. Upon import to IGOR Pro the desmeared data were reduced to 200 points (with a 5 data point boxcar average) matching the number of bins to be fit. The size distribution of the sample was then determined by using the size distribution macro in the IRENA package. The SAXS patterns were fit using the maximum entropy method, assuming spherical particles (confirmed with TEM), to yield a histogram of volume distribution binned by diameter. For each sample, polydispersity and average core size were determined by fitting a Gaussian function to the histogram distribution.

Characterization of Sensing Behavior by UV-Vis Spectroscopy.

All measurements were performed using a Mikropack DH-2000 UV-vis-NIR light source equipped with an Ocean Optics USB2000 spectrophotometer. Absorbance of purified AuNPs was measured in a quartz cuvette cleaned with aqua regia and rinsed with nanopure water in between all measurements. Gold nanoparticles comprising mixed ligand systems (e.g., ligands generated from ligand precursors 122, 124, 140, and 144, and ligands generated from ligand precursor 102) were diluted (to 0.5 A.U. at 500 nm) to avoid exceeding the saturation limit of the instrument while the solution volume was maintained at 2 mL total and an initial absorption spectrum was obtained. For determination of colorimetric sensing capabilities, 10 µL of 4 mM $Eu(NO_3)_{3(aq.)}$ was added to the cuvette while stirring. Sensing occurred rapidly (seconds) and the resulting absorbance spectrum was recorded after 2 minutes. The change in absorbance at 550 nm from the original spectrum to the final $Eu^{3+}$ added spectrum was used for the optimization of the sensing response as a function of % malonamide. Reversibility of the prepared nanoparticle sensors that demonstrated a colorimetric sensing response for $Eu^{3+}$ was determined by recording the initial absorbance spectrum of a rapidly stirring solution containing 1.98 mL purified mixed ligand nanoparticles and 20 µL of 1M Tris buffer (pH=7.5). Tris buffer was utilized to improve the chelating ability of EDTA and increase the overall binding affinity. An addition of $Eu(NO_3)_3$ (aq., 20 µM) as indicated above was added followed by a subsequent addition of EDTA (aq., 20 µM).

Spectra were obtained after each addition. The recorded absorbance value at 550 nm versus the addition of $Eu^{3+}$ and then EDTA were reviewed. Reversibility was defined as the increase and subsequent decrease in absorbance at 550 nm (back to the original value) following the addition of $Eu^{3+}$ and EDTA, respectively. All samples containing EG-malonamides that yielded an original colorimetric response were found to be reversible. The detection limit of the nanoparticle materials was determined through a spectral titration of $Eu(NO_3)_3$. Increased sensitivity was found to occur with higher AuNP concentrations and thus starting absorbance values were fixed at ~1 A.U. (at 500 nm) for the samples, for higher concentrations while staying well within the saturation limits of the instrument. The absorbance spectrum of purified gold nanoparticles comprising mixed ligand systems (e.g., ligands generated from ligand precursors 122, 124, 140, and 144, and ligands generated from ligand precursor 102) was used as the blank. Successive 1 µL aliquots of appropriate $Eu^{3+}$ concentration were added until a measurable absorbance change at 550 nm was observed. The detection limit was defined as an increase >3× the noise of the instrument (~0.002 A.U.).

For upper sensing limit measurements, AuNPs were diluted to yield a starting absorbance of ~0.5 at 500 nm. The AuNPs were again used as a blank and successive 2 µL aliquots of 2 µM $Eu(NO_3)_3$ were added. Absorbance changes at 550 nm were then monitored and the upper limit was determined after an additional aliquot produced no further change in the absorbance value (FIG. 22).

Nanoparticle Cross-Linking Investigation with Transmission Electron Microscopy, SAXS, and Fourier Transform Infrared Spectroscopy.

TEM analysis of purified nanoparticle samples was performed on a FEI Tecnai G2 Spirit TEM operating at 120 kV. AuNP samples were prepared for analysis by floating amine-functionalized SMART grids (Dune Sciences) on top of a drop of diluted solution (either AuNPs only, AuNPs+20 µM $Eu^{3+}$, or AuNPs+20 µM $Eu^{3+}$+20 µM EDTA, pH 7.5 with Tris buffer) for ~60 s. The grids were allowed to dry in ambient conditions before imaging occurred.

SAXS agglomeration analyses of purified AuNPs were performed by first measuring the scattering pattern of gold nanoparticles comprising mixed ligand systems (e.g., ligands generated from ligand precupors 122, 124, 140, and 144, and ligands generated from ligand precursor 102), followed by a second measurement of AuNPs with $Eu^{3+}$ present in solution. Specifically, gold nanoparticles comprising mixed ligand systems (e.g., ligands generated from ligand precursors 122, 124, 140, and 144, and ligands generated from ligand precursor 102) (200 µL, 0.5 A.U. @ 500 nm) were exposed to line-collimated X-rays for 40 seconds exposure and averaged over 64 scans. To assess the solution phase agglomeration caused by malonamide binding interactions with $Eu^{3+}$ present, scattering patterns were obtained on the gold nanoparticle solutions at the same concentration as dispersed particles but also containing $Eu(NO_3)_3$ (20 µM final). The raw data was background and dark subtracted, desmeared, and imported into IGOR pro as indicated in the core size determination discussion. AuNPs only (dispersed) were fit using the Modelling II macro in IRENA assuming spherical particles, yielding a Gaussian distribution, and were successfully modeled using the LSQF method as a dilute system (with no contribution from a structure factor). $Eu^{3+}$+AuNP samples with >50% malonamide content in the ligand shell displayed little to no change to the scattering pattern and were also fit as dilute systems (FIG. 23). Scattering patterns of $Eu^{3+}$+AuNP samples with ≤50% malonamide content revealed a first diffraction peak indicative of regular ordering in solution and were fit using the Modeling II macro and LSQF method, again assuming spherical particles and Gaussian distribution, however with a hard sticky spheres structure factor.

FT-IR analyses of AuNPs were obtained using a Thermo Scientific Nicolet 6700 spectrometer. Lyophilized, purified AuNPs (~0.5 mg) were added to KBr and pressed into pellets. Measurements were recorded in transmittance mode under a stream of dry air with resolution of 8 cm$^{-1}$ averaged over 128 scans. For assessment of Eu$^{3+}$ binding, lyophilized AuNPs produced from the same batch were dissolved in 0.49 mL H$_2$O and aqueous Eu$^{3+}$ (10 µL, 1 mM Eu(NO$_3$)$_3$) for Eu$^{3+}$=20 04. The mixture was incubated for 30 min, lyophilized to a powder, pressed into a KBr pellet, and spectra were obtained.

Batch-Based Synthesis of Gold Nanoparticles Comprising Mixed Ligands from Ligand Precursors 144 and 102:

An aqua regia (3:1 HCl:HNO$_3$) cleaned 250 mL round-bottom flask equipped with a stir bar was charged with 100 mL of H$_2$O, 1 mL of HAuCl$_4$.H$_2$O solution (0.1 M), and 500 µL of an aqueous solutions of ligand precursors 144 and 102 (0.1 M). The reaction mixture was allowed to stir for 10 minutes, and then 2.0 mL of a freshly prepared aqueous 0.1 M NaBH$_4$ solution was added. The reaction mixture was allowed to stir for 3 hours. The resulting nanoparticles required filtration through a coarse-fritted glass funnel before collection and further purification using diafiltration as described in the methods section for AuNPs obtained by microfluidic synthesis.

Discussion of Synthetic Trials Resulting from Batch-Based Synthesis of Gold Nanoparticles Comprising Mixed Ligands from Ligand Precursors 144 and 102.

Of the 34 embodiments performed, 2 trials resulted in nanoparticles that showed spectral and colorimetric changes upon the addition of Eu$^{3+}$, but no changes were observed after EDTA addition (to induce reversibility). Nanoparticles that showed no spectral or colorimetric response after the addition of Eu$^{3+}$ or EDTA dominated the experiments (24 of 34 total). Nanoparticles functionalized primarily with ligands obtained from ligand precursor 144 responded both visually and spectrally from Eu$^{3+}$ addition. Particles containing only a few ligands obtained from ligand precursor 144 responded to both the Eu$^{3+}$ and EDTA additions. The inconsistency of the results suggested that despite consistent synthetic procedures, the ligand shell composition varied greatly from batch to batch. Furthermore, efforts to functionalize AuNPs with a small number of ligands obtained from ligand precursor 144 through introduction of low concentration solutions of 102 or through exposure of gold nanoparticles functionalized with ligands obtained from ligand precursor 144 to an excess of 102, led to nanoparticle solutions that aggregated upon exchange or during the purification process, preventing the nanoparticles to be captured for analysis. Both aggregation events suggest that the stability of the functionalized products were compromised during exchange. Reaction trials that led to the synthesis of functionalized AuNPs that showed reversible colorimetric response implied that fabrication of a reversible assembly was possible. The core sizes and polydispersities were also not consistent during the trials or as a function of input mixed ligand ratios. All of these factors contributed to the understanding how structural variations in the ligand shell influence cross-linking and sensing. The irreproducibility in the nanoparticles obtained tended to scale with the size of the reaction vessel (e.g. 250-mL round bottom flasks worked better than scintillation vials) that were used during synthesis.

Synthesis of Ligand Precursors

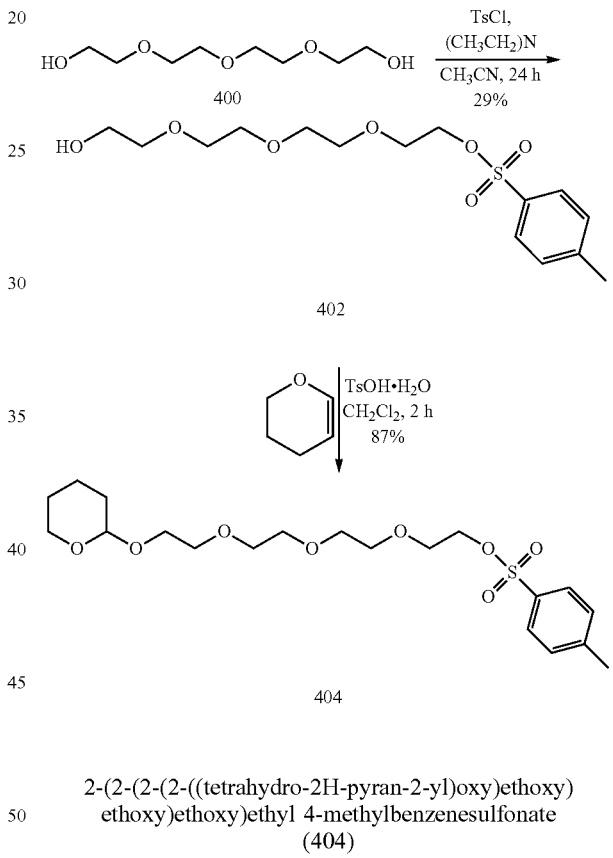

2-(2-(2-(2-((tetrahydro-2H-pyran-2-yl)oxy)ethoxy)ethoxy)ethoxy)ethyl 4-methylbenzenesulfonate (404)

To an ice cold solution of 2-(2-(2-(2-hydroxyethoxyl)ethoxy)ethyl 4-methylbenzenesulfonate2 (5.24 g, 15.0 mmol) dissolved in CH$_2$Cl$_2$ (150 mL), 3,4-Dihydro-2H-pyran (1.65 g, 19.7 mmol) was added slowly while stirring, followed by addition of p-toluenesulfonic acid monohydrate (0.69 g, 3.6 mmol). The solution was allowed to warm to room temperature and stirred for 2 hours. H$_2$O (50 mL) was added to the reaction mixture and the organic phase was separated. The organic phase was then washed with additional H$_2$O (100 mL) and brine (100 mL), dried over Na$_2$SO$_4$, and concentrated in vacuo to yield 404 (5.99 g, 87%) as an oil that did not require further purification. $^1$H-NMR: (CDCl$_3$): b=1.48-1.93 (m, 6H), 2.45 (s, 3H), 3.48-3.94 (m, 14H), 3.84-3.94 (m, 2H), 4.18 (t, 2H), 4.64 (m, 1H), 7.35 (d, 2H), 7.81 (d, 2H).

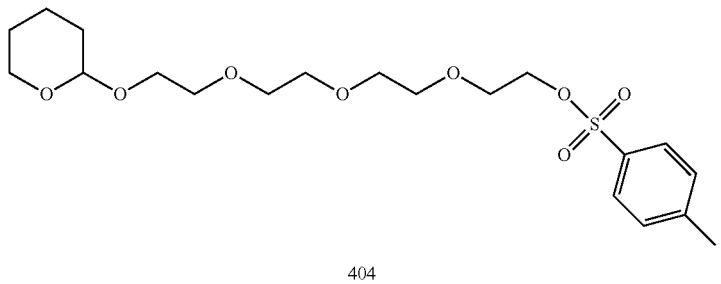 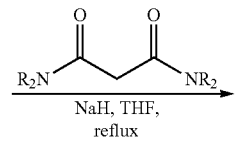

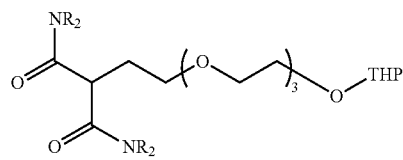

R = CH₃ (406), 31%
R = CH₂CH₃ (408), 85% (crude)

N',N',N³,N³-tetramethyl-2-(2-(2-(2-(2-((tetrahydro-2H-pyran-2-yl)oxy)ethoxy)ethoxy)ethoxy)ethyl) malonamide (406)

Sodium hydride (0.391 g, 16.3 mmol) was dissolved in dry THF (100 mL) under N₂ in a 3-neck round bottom flask with stir bar. N¹,N¹,N³,N³-tetramethylmalonamide (2.57 g, 16.2 mmol) dissolved in dry THF (10 mL) was added dropwise over the course of 10 minutes while stirring yielding a cloudy and viscous solution. The monotosylated and protected glycol 404 (5.98 g, 13.8 mmol) dissolved in dry THF (5 mL) was then added dropwise to the solution and the mixture was heated at reflux for 16 hours. A solid precipitate formed upon letting cool to room temperature, which was subsequently removed by filtration. THF was removed by rotary evaporation, and the oil was dissolved in CH₂Cl₂ (80 mL). The solution was washed with water (100 mL), brine (100 mL), dried with Na₂SO₄, and concentrated by rotary evaporation. Flash column chromatography (3:2 CH₂Cl₂/acetone) on silica gel was used to isolate 406 (1.78 g, 31%) as a colorless oil. ¹H-NMR (CDCl₃): δ=1.48-1.93 (m, 6H), 2.19 (q, 2H), 3.02 (d, 12H), 3.48-3.70 (m, 14H), 3.83-3.94 (m, 2H), 3.98 (t, 1H), 4.64 (m, 1H).

N¹,N¹,N³,N³-tetraethyl-2-(2-(2-(2-(2-((tetrahydro-2H-pyran-2-yl)oxy)ethoxy)ethoxy)ethoxy)ethyl) malonamide (408)

Sodium hydride (0.362 g, 15.0 mmol) was dissolved in freshly distilled THF (100 mL) under N₂. N¹,N¹,N³,N³-tetraethylmalonamide (2.73 g, 12.7 mmol, dissolved in 5 mL THF) was added dropwise, followed by addition of 404 (4.39 g, 10.6 mmol, dissolved in 10 mL THF). The orange/yellow mixture was heated at reflux for 20 hours. Upon letting cool to room temperature, precipitated material was removed by filtration and THF was removed by rotary evaporation. The crude residue was dissolved in CH₂Cl₂ (50 mL), washed with deionized water (2×100 mL) and brine (100 mL), dried using Na₂SO₄ and concentrated. A short silica plug (5:1 CH₂Cl₂/CH₃OH) was used to remove tosylate salts. Further purification was not performed and the crude product 408 was carried on to the THP deprotection step. H-NMR confirmed successful alkylation by presence of a quartet at 2.18 ppm (in CDCl₃), typical of methylene protons α to the central carbon of the TMMA functionality.

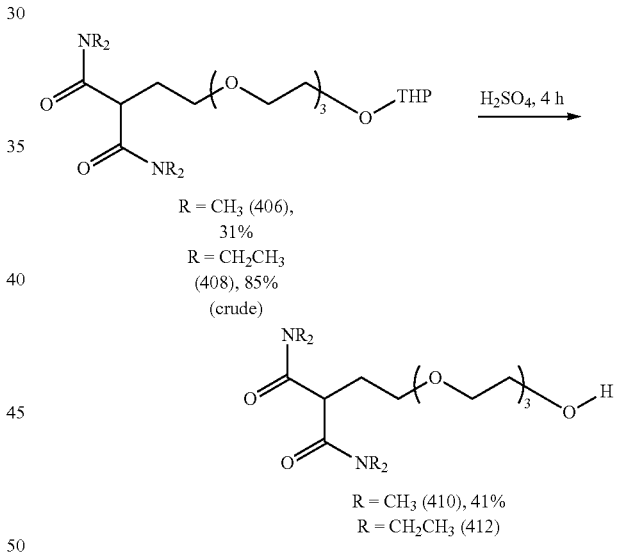

R = CH₃ (406), 31%
R = CH₂CH₃ (408), 85% (crude)

R = CH₃ (410), 41%
R = CH₂CH₃ (412)

2-(2-(2-(2-(2-hydroxyethoxyl)ethoxy)ethoxy)ethyl)-N¹,N¹,N³,N³-tetramethylmalonamide (410)

THP-protected 406 (1.77 g, 4.23 mmol) was dissolved in absolute ethanol (15 mL) in a 50 mL round bottom flask containing a stir bar. Concentrated sulfuric acid (5 drops) was added and the mixture was stirred at room temperature for 4 hours. Saturated NaHCO₃ (aq., 1 mL) was used to neutralize the solution. The solvent was then removed by rotary evaporation. The crude material was dissolved in CH₂Cl₂, causing precipitation of salt which was removed by filtration. The solution was concentrated in vacuo to yield 410 as a colorless oil (0.501 g, 41%). ¹H-NMR (D2O): δ=1.95 (q, 2H), 2.89 (d, 12H), 3.39 (t, 2H), 3.48-3.62 (m, 12H), 4.07 (t, 1H). ESI-MS (H$_2$O/CH$_3$OH): m/z calcd for C$_{15}$H$_{31}$N$_2$O$_6$ [M+H+] 335.22. found, 335.34.

N$^1$,N$^1$,N$^3$,N$^3$-tetraethyl-2-(2-(2-(2-(2-hydroxyethoxyl)ethoxy)ethoxy)ethyl)malonamide (412)

Concentrated H$_2$SO$_4$ (5 drops) was added to a 50 mL ethanolic solution of THP-protected diamide 408 (4.09 g, 8.61 mmol). The solution was stirred at room temperature for 4.5 hours before being neutralized with NaHCO$_3$ (1 mL, satd., aq.). Ethanol was removed by rotary evaporation and the residue was dissolved in CH$_2$Cl$_2$ (30 mL). The solution was washed with H$_2$O (100 mL) and brine (100 mL), dried over Na$_2$SO$_4$, and the solvent removed in vacuo. A silica plug (EtOAc) was used to obtain crude product 412 (0.412 g) as indicated by the loss of upfield THP signals (~1.48-1.93 ppm in CDCl$_3$). The product was carried onto the next step without further purification.

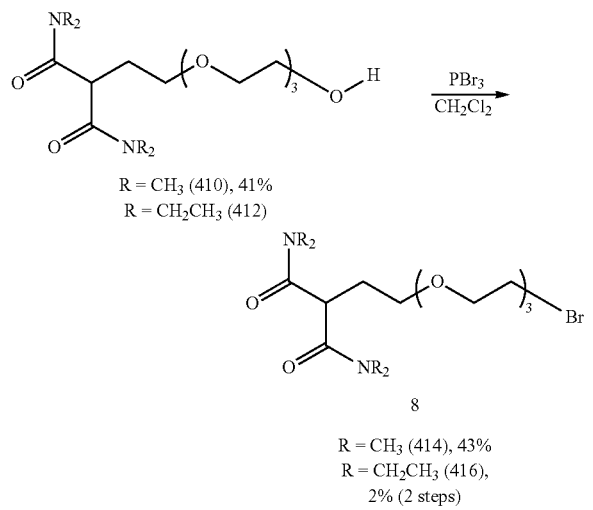

2-(2-(2-(2-(2-bromoethoxyl)ethoxy)ethoxy)ethyl)-N$^1$,N$^1$,N$^3$,N$^3$-tetramethylmalonamide (414)

Alcohol 410 (0.318 g, 0.95 mmol) was dissolved in dry CH$_2$Cl$_2$ (50 mL) under a N$_2$ atmosphere and cooled in an ice-water bath. Phosphorus tribromide (60 μL, 0.64 mmol) was added dropwise to the solution while stirring. The mixture was allowed warm to room temperature then stirred for 18 hours. The solution was then heated at reflux for 1 hour to complete the reaction, let cool back to room temperature before water (20 mL) was added to the solution. The aqueous phase was extracted with CH$_2$Cl$_2$ (3×20 mL). The combined organics were washed with 10% NaHCO$_3$ (aq., 25 mL), 5% H$_2$SO$_4$ (aq., 25 mL), brine (25 mL), dried with Na$_2$SO$_4$, and then concentrated in vacuo to yield 414 as an oil (160 mg, 43%). $^1$H-NMR (CDCl$_3$): δ=2.20 (q, 2H), 3.06 (d, 12H), 3.49 (t, 2H), 3.54 (t, 2H), 3.57-3.71 (m, 8H), 3.82 (t, 2H), 4.14 (t, 1H). ESI-MS (CH$_3$OH): m/z calcd for C$_{15}$H$_{30}$BrN$_2$O$_5$ [M+H+] 397.13. found, 397.31.

N$^1$,N$^1$,N$^3$,N$^3$-tetraethyl-2-(2-(2-(2-(2-bromoethoxyl)ethoxy)ethoxy)ethyl)malonamide (416)

To an ice-bath cooled and stirred solution of alcohol 412 (412 mg, 1.05 mmol) in dry CH$_2$Cl$_2$ (50 mL), phosphorus tribromide (230 mg, 0.850 mmol) was added and allowed to stir for 10 minutes before letting warm to room temperature. The mixture was heated at reflux for 24 hours, followed by addition of water (20 mL) upon cooling. The aqueous phase was extracted with CH$_2$Cl$_2$ (3×20 mL). The combined organics were washed with 10% NaHCO$_3$ (aq., 25 mL), 5% H$_2$SO$_4$ (aq., 25 mL), and brine (25 mL), dried with Na$_2$SO$_4$ and the solvent was removed by rotary evaporation. The crude residue was purified by flash column chromatography (9:1 CH$_2$Cl$_2$/CH$_3$OH) on silica gel to obtain 416 (79 mg, 2% (2 steps)). $^1$H-NMR (CDCl$_3$): δ=1.16 (dt, 12H), 2.19 (q, 2H), 3.31-3.54 (m, 8H), 3.58-3.68 (m, 12H), 3.80-3.86 (m, 3H). ESI-MS (CH$_3$OH): m/z calcd for C$_{19}$H$_{37}$BrN$_2$NaO$_5$ [M+Na+] 475.18; [M+2+Na+], 477.18. found 475.42, 477.42.

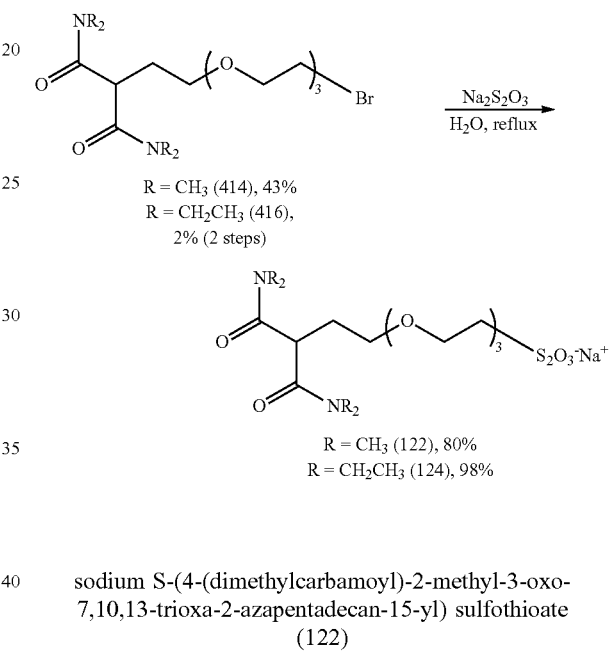

sodium S-(4-(dimethylcarbamoyl)-2-methyl-3-oxo-7,10,13-trioxa-2-azapentadecan-15-yl) sulfothioate (122)

Sodium thiosulfate (145 mg, 0.58 mmol) was dissolved in H$_2$O (20 mL) and added dropwise to a stirring solution of bromide 414 (155 mg, 0.39 mmol) dissolved in ethanol (20 mL). The mixture was heated at reflux for 24 hours before removing the solvents by rotary evaporation. The crude compound was dissolved in ethanol (50 mL) to precipitate out salt impurities, which were then removed by filtration. This process was repeated twice to obtain Bunte salt 122 as an oily solid upon concentration in vacuo (146 mg, 80%). $^1$H-NMR (D$_2$O): δ=1.96 (q, 2H), 2.90 (d, 12H), 3.16 (t, 2H), 3.43 (t, 2H), 3.49-3.64 (m, 8H), 3.75 (t, 2H), 4.08 (t, 1H). ESI-MS (CH3CN): m/z calcd for C$_{15}$H$_{29}$N$_2$O$_8$S$_2$ [M−Na+], 429.14. found, 429.22.

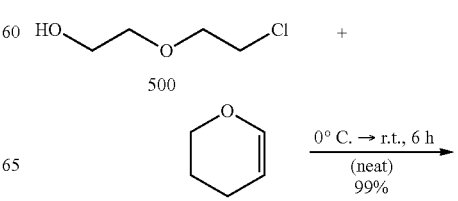

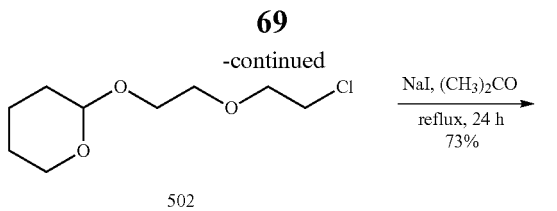

502

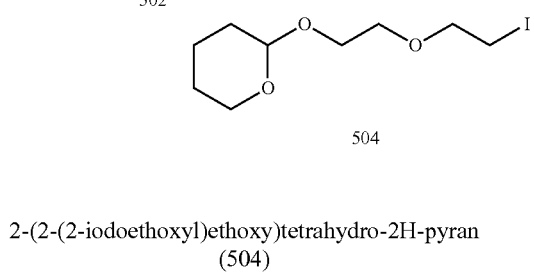

504

2-(2-(2-iodoethoxy)ethoxy)tetrahydro-2H-pyran (504)

Sodium iodide (4.49 g, 30.0 mmol) was dissolved in dry acetone (40 mL). 2-(2-(2-chloroethoxy)ethoxy)tetrahydro-2H-pyran (5.00 g, 24.0 mmol) was added and the mixture was heated at reflux while stirring for 24 hours. The white precipitate formed upon cooling to room temperature was filtered off and the acetone removed in vacuo. The crude yellow residue was dissolved in $CH_2Cl_2$ (40 mL) and the resulting precipitate was removed by filtration. The filtrate was washed with $H_2O$ (40 mL), dried with $Na_2SO_4$, and concentrated in vacuo to yield crude iodide product 504 (5.23 g, 73%). Product was used without further purification in the subsequent step.

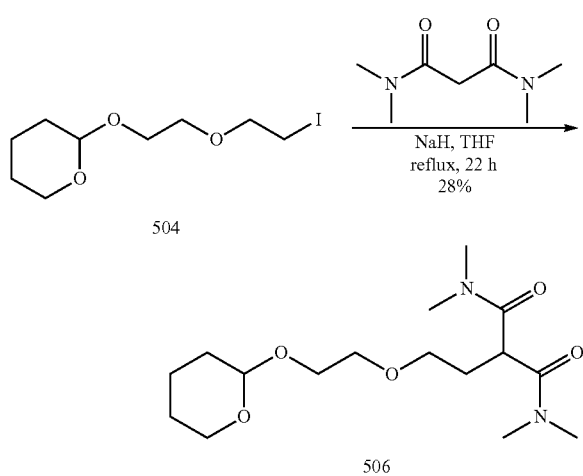

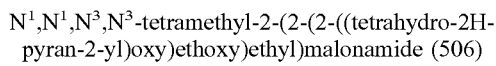

506

$N^1,N^1,N^3,N^3$-tetramethyl-2-(2-(2-((tetrahydro-2H-pyran-2-yl)oxy)ethoxy)ethyl)malonamide (506)

Sodium hydride (0.288 g, 12 mmol) was dissolved in distilled THF (100 mL) under $N_2$. $N^1,N^1,N^3,N^3$-tetramethylmalonamide (1.74 g, 11.0 mmol) was dissolved in 10 mL THF and added dropwise to the flask over 5 min upon which the mixture became thick and cloudy white. THP-protected iodide 504 (dissolved in 10 mL THF) was then added to the flask causing the solution to become less viscous and the resulting mixture was then heated at reflux while stirring for 22 hours. The solid precipitate present was filtered off and THF removed by rotary evaporation. The crude residue was dissolved in $CH_2Cl_2$ (75 mL), washed with $H_2O$ (2×100 mL), brine (100 mL), dried with $Na_2SO_4$ and then concentrated in vacuo. Flash column chromatography (12:1 $CH_2Cl_2/CH_3OH$) on silica gel was used to isolate 506 (934 mg, 28%). $^1$H-NMR (600 MHz, $CDCl_3$): b=4.63 (t, 1H), 4.00 (t, 1H), 3.85-3.89 (m, 2H), 3.51-3.63 (m, 6H), 3.05 (d, 6H), 2.99 (s, 6H), 2.19 (q, 2H), 1.80-1.87 (m, 1H), 1.70-1.75 (m, 1H), 1.53-1.63 (m, 4H). ESI-MS ($CH_3OH$): m/z calcd for $C_{16}H_{30}N_2NaO_5$ [M++Na+], 353.20. found, 353.33.

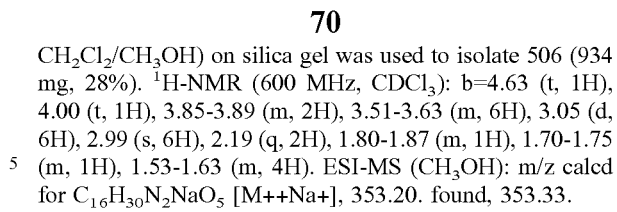

506

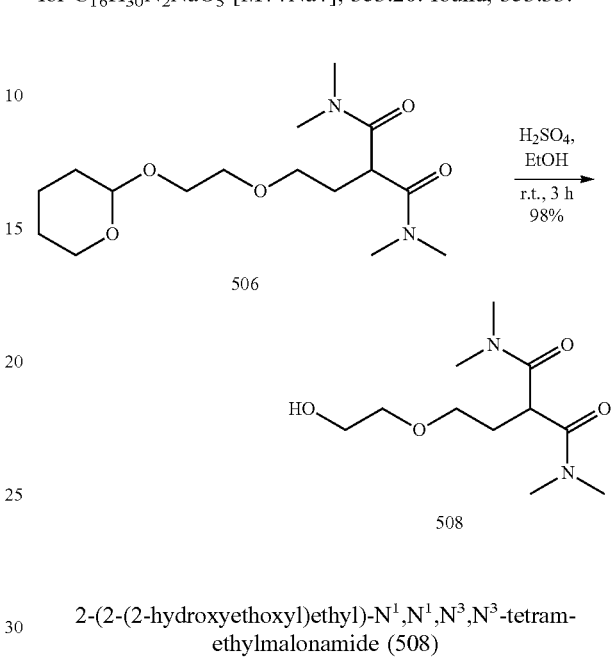

508

2-(2-(2-hydroxyethoxyl)ethyl)-$N^1,N^1,N^3,N^3$-tetramethylmalonamide (508)

Concentrated $H_2SO_4$ (5 drops) was added to a solution of THP-protected malonamide 13 (924 mg, 2.80 mmol) dissolved in absolute EtOH (10 mL). The mixture was stirred for 3 hours at room temperature before being neutralized with saturated $NaHCO_3$ (aq., 1 mL). The solvent was removed by rotary evaporation and the crude oil was dissolved in $CHCl_3$ (25 mL) to precipitate a white solid that was removed by filtration. The filtrate was concentrated in vacuo to yield pure deprotected 508 (675 mg, 98%). $^1$H-NMR ($CDCl_3$): δ=3.92 (t, 1H), 3.72 (m, 1H), 3.60 (t, 2H), 3.55 (t, 2H), 3.02 (d, 12H), 2.36 (br s, 1H), 2.21 (q, 2H). ESI-MS: ($CH_3OH$): m/z calcd for $C_{11}H_{23}N_2O_4$ [M+H+], 247.17. found, 247.13.

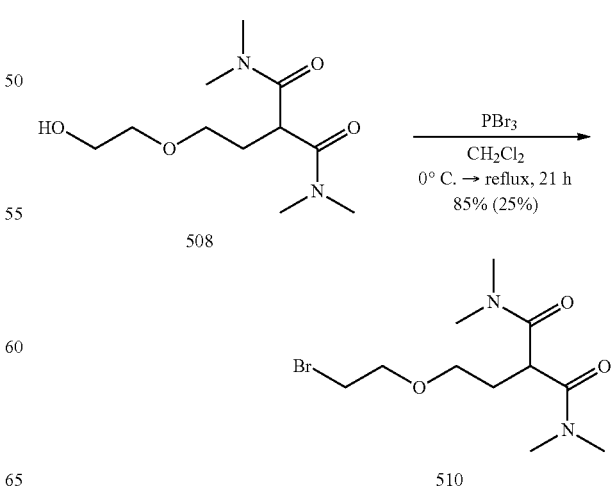

510

2-(2-(2-bromoethoxy)ethyl)-N¹,N¹,N³,N³-tetramethylmalonamide (510)

Alcohol 508 (670 mg, 2.70 mmol) was dissolved in dry $CH_2Cl_2$ (25 mL) under $N_2$. Phosphorus tribromide (590 mg, 2.20 mmol) was then added slowly (over 3 minutes) to an ice-bath cooled flask while stirring. The mixture was then allowed to warm back to room temperature over 10 minutes and then heated at reflux for 19 hours. After cooling back to r.t., $H_2O$ (20 mL) was added. The aqueous phase was extracted with $CH_2Cl_2$ (3×20 mL). The combined organics were washed with 10% $NaHCO_3$ (aq., 25 mL) and brine (25 mL), dried with $Na_2SO_4$, and the solvent was removed with rotary evaporation. $^1$H-NMR ($CDCl_3$) analysis indicated 85% conversion to the bromide in the crude mixture. Flash column chromatography (3:2 $CH_2Cl_2$/acetone) on silica gel was used to isolate 510 (207 mg, 25%) as an oil. $^1$H-NMR ($CDCl_3$): δ=4.07 (t, 1H), 3.76 (t, 2H), 3.57 (t, 2H), 3.49 (t, 2H), 3.02 (d, 12H), 2.20 (q, 2H). ESI-MS ($CH_3OH$): m/z calcd for $C_{11}H_{22}BrN_2O_3$, [M+H+], 309.08, [M+2+H+], 311.08. found 309.10, 311.06.

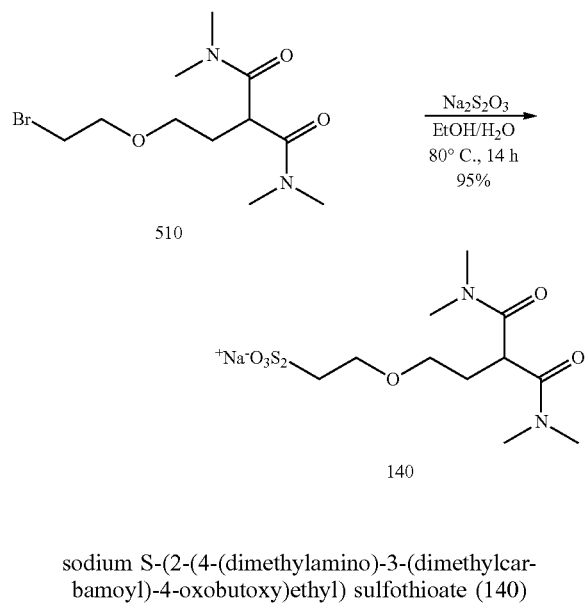

sodium S-(2-(4-(dimethylamino)-3-(dimethylcarbamoyl)-4-oxobutoxy)ethyl) sulfothioate (140)

Brominated malonamide 510 (202 mg, 0.65 mmol) was dissolved in a mixture of water (10 mL) and ethanol (25 mL). Sodium thiosulfate (124 mg, 0.78 mmol) dissolved in water (5 mL) was added to the flask and the mixture was heated at reflux for 14 hours. Upon letting cool to room temperature, ethanol and water were removed in vacuo. The crude residue was dissolved in ethanol and the resulting insoluble salts were filtered off. This salt removal process was repeated two additional times. The dried residue was then dissolved in acetonitrile for final precipitation and filtration of salt impurities. Solvents were removed from the filtrate in vacuo to yield crystalline white solid 140 (223 mg, 95%). $^1$H-NMR (D2O): δ=4.13 (t, 1H), 3.70 (t, 2H), 3.46 (t, 2H), 3.15 (t, 2H), 2.90 (d, 12H), 1.95 (q, 2H).

Quantifying AuNP Mixed Ligand Precursor Compositions for Gold Nanoparticles Having Mixed Ligand Systems:

An exemplary $^1$H-NMR (300 MHz) spectrum of purified gold nanoparticles with ligands obtained from ligand precursor 122 in $D_2O$ showing broad characteristic peaks without free-ligands present is illustrated in FIG. 24A. In the NMR spectrum of the ligand precursor 122, in $D_2O$, the methyl protons are present as a doublet at 2.85 and 2.95 ppm which each integrate to 6 protons (FIG. 24 B). In the iodine decomposed gold nanoparticle proton spectra of the gold nanoparticle comprising ligands obtained from ligand precursor 122, the peak produced from the two methylene protons a to sulfur (S—S—$CH_2$) shift upfield relative to the Bunte salt precursor in the disulfide and combine with the methyl peak at 2.85 ppm (FIG. 24C), which changes the integration values for the peaks at 2.85 and 2.95 ppm to 8 and 6 respectively (assuming one half of the disulfide). In the case of gold nanoparticles functionalized with mixed ligand systems obtained from ligand precursors 102 and 122 mixed ligand AuNPs, both ligands have methylene protons (S—S—$CH_2$) α to the disulfide which shift upfield and combine with the TMMA peak at 2.85 ppm. Setting the peak at 2.95 ppm to an integration value of 6 causes the peak at 2.85 ppm to change to an integration value of N, which is due to 6 protons from the 122 methyl groups, 2 protons from the 122 disulfide peak and N-8 protons from the 102 disulfide peak. Therefore, the percentage of 122 can be found by equation 1. Example spectra of decomposed gold nanoparticles with mixed ligands formed from ligand precursors 122 and 102 with varying ratios of 1 from 10-100% of the ligand shell are shown in FIG. 25.

$$\%TMMA(122) = 100 \times \frac{2}{2+(N-8)} \quad (1)$$

Initially, the $^1$H-NMR spectra in $D_2O$ of gold nanoparticles comprising mixed ligands obtained from ligand precursors 144 and 102 upon $I_2$ addition showed that no alkyl malonamides were previously present on the NP surface in the samples at multiple feed ratios. However, upon further investigation of only the disulfide ligand of 144, it was found that the disulfide was not soluble in pure water. To aid in quantification, NMR analyses of these compounds were performed in a mixture of 90% $D_2O$/10% DMSO-$d_6$. Alkyl TMMA-AuNPs (containing ligands obtained from ligand precursor 144) yield alkyl proton peaks in the disulfide peak that are no longer convoluted with the TMMA peaks at 2.85 and 2.95 ppm. Setting the peak at 2.95 ppm to an integration value of 6 causes the peak at 2.85 ppm to assume an integration value of N, which is due to 6 protons from TMMA and N-6 protons due to EG-disulfide peak. Therefore, the percentage of ligands obtained from ligand precursor 144 can be found by equation 2.

$$\% TMMA(144) = 100 \times \frac{2}{2+(N-6)} \quad (2)$$

Quantification of gold nanoparticles functionalized with ligands derived from ligand precursor 102 and ligands obtained from ligand precursor 124 was performed by acquiring spectra before (to confirm successful purification, FIG. 26A) and after the addition of $I_2$ to release surface bound ligands as disulfides in $D_2O$ (FIG. 26B). The methyl protons on the tetraethylmalonamide functionality of 124 are split into two triplets at ~0.1.05 ppm, each representing 6 protons (from each half of the disulfide). The integral of one triplet was fixed at 6. Similar to gold nanoparticles functionalized with ligands derived from ligand precursor 102 and ligands obtained from ligand precursor 122, both ligands have methylene protons (S—S—CH$_2$) α to the disulfide that have identical chemical shifts at 2.85 ppm and their combined integral is indicated as N. The % of TEMA 124 disulfide could then readily be determined by dividing 2/N (Equation 3).

$$\% \ TEMA(124) = 100 \times \frac{2}{N} \quad (3)$$

SAXS Modelling and Analysis for Measuring Regular Spaced NP Agglomerates in Solution:

The data was modeled using the Modeling II macro in IRENA as polydisperse spherical particles including a hard spheres structure factor (FIG. 15, line "A") utilizing the Percus-Yevick approximation:

$$S(q) = \frac{1}{1 + 24\eta G(2qR_{HS})/(2qR_{HS})}.$$

Incorporation of the structure factor into the SAXS modeling allowed determination of the hard-sphere radius RHS and the mean sphere volume fraction η. These parameters were used to ascertain the correlation distance between two nanoparticles that are agglomerated by Eu$^{3+}$ cross-linking and the probability to find nanoparticles in close promixity to another (extent of agglomeration). For ligands obtained from ligand precursor 122, it was expected that the maximum NP-NP fully extended distance was 4.2 nm from Au—Au based upon PM3 calculations of the ethylene glycol chain, average Au—S bond lengths, and Eu$^{3+}$-malonamide bond distances (FIG. 27). A correlation distance of 3.6 nm was determined experimentally for the cross-linked AuNPs. The ethylene glycol linker of the malonamide ligand is flexible and contributes to this shortened cross-link distance. The solution scattering result supports the formation of AuNP bridged through central Eu$^{3+}$-malonamide interactions when diluted down to 10% in the ligand shell. The mean sphere volume fraction (η) was found to be 0.37, indicating that the probability to find a nanoparticle near another or multiple others is high. For comparison, a non-interacting sample has a η value of 0, whereas an η value for a body centered cubic arrangement (often observed for AuNP arrangements) is 0.68.

Ligand Preparation:

The Bunte salt analog of 2-[2-(2-mercaptoethoxy)-ethoxy]ethanol (102) was synthesized by dissolving the appropriate organohalide precursor and sodium thiosulfate (0.80 mol equiv) in 150 mL of water and heated to reflux for 4 hours. The water was then removed by rotary evaporation and drying on a vacuum line. The crude products were purified by dissolution in ethanol, followed by gravity filtration.

The length of ligands obtained from ligand precursor 122 was determined from an optimized structure of the thiol analog by semi-emperical methods (PM3). The dicarbonyl of the tetramethylmalonamide (TMMA) moiety was locked by using an ethylene bridge to the oxygen atoms in the carbonyl to achieve a more planar conformation that is known to exist when bound to a lanthanide ion. The S—O (carbonyl) distance was found to be 16.50 Å in the lowest energy structure. The Au—S bond length used was 2.32 Å, and the O (carbonyl) to Eu$^{3+}$ distance with TMMA is known by crystallography to be 2.41 Å at a maximum. In total, the estimated Au—Eu$^{3+}$ length with ligands obtained from ligand precursor 122 is 21.2 Å. Therefore, in a 2:1 (L: Eu$^{3+}$) binding conformation, the fully extended AuNP-AuNP distance is estimated to be 42.4 Å.

In this embodiment, exemplary gold nanoparticles were prepared using flow synthesis and results from such methods were compared to batch syntheses of gold nanoparticles. In one embodiment, gold nanoparticles functionalized with ligands derived from ligand precursor 102 and ligands obtained from ligand precursor 144 were prepared using through batch synthetic methods including direct synthesis and place exchange reactions. A total of 34 trials using various ratios of ligand precursors 102 and 144 were performed. The direct synthesis of gold nanoparticles functionalized with ligands obtained from ligand precursor 102 and ligands obtained from ligand precursor 144 using mixtures of the two ligand solutions resulted in preparing nanoparticle solutions that were stable and water-soluble; however, inconsistent particle assembly was obtained in the presence of Ln$^{3+}$. These results likely occurred due to inadequate mixing of the reagents, which thereby can lead to differing compositions in the final NP product and hence vary their ability to cross-link and function as a sensor.

To address this issue, the synthesis of nanoparticles with rapid mixing at high-flow rates in a microfluidic reactor to minimize compositional variability was explored. This approach was motivated by the need to increase batch to batch reproducibility in terms of core sizes and composition and minimize polydispersity. Furthermore, the aim was to quickly evaluate products with minor structural variation. AuNPs were thus synthesized in a direct fashion at flow rates of 60 mL/min using a microfluidic reactor with diluent ligand precursor 102 at varying input ratios from premixed Bunte salt precursors to tune the concentration of ligand precursor 144. The functionalization ratio of the mixed ligands present on the NP surface was evaluated and compared to the feed ratio. Table 7 summarizes results from particular disclosed embodiments. In some embodiments, the mixed ligands could be incorporated readily by simply premixing the ligands at the desired feed ratio to obtain a similar actual composition on the nanoparticle surface. After extensive purification of the synthesized nanoparticles using diafiltration, concentration by lyopholization, and redispersion into deuterated solvent, I$_2$ was added to oxidize surface bound ligands and release them as the corresponding disulfides.

TABLE 7

| Mixed Ligand precursor compositions | |
|---|---|
| Feed Ratio | AuNP composition: |
| 102:144 | |
| 10:90 | 12:88 |
| 50:50 | 24:76 |
| 75:25 | nanoparticles unstable |

$^a$Composition determined by I$_2$-decomposition and $^1$H-NMR analysis

Quantification by $^1$H-NMR of characteristic peaks determined that successful dilution of ligand precursor 144 matching the feed ratio could be achieved at low ratios, whereas moderate amounts (24%, feed ratio=50%) can be introduced at higher feed ratios (Table 7). AuNPs fully functionalized with ligand obtained from ligand precursor 144 or at high feed ratios (75%) irreversibly aggregated after lyophilization and could not be redispersed for NMR analyses indicating the poor extent of steric stabilization. Without being limited to a particular theory, it is currently believed that the ligands self-associate prior to AuNP formation within the mixed-ligand solution or the rates of incorporation of the ligands with different tethers vary.

Additionally, nanoparticle average core sizes resulting from the direct syntheses performed were determined in solution at synthesis concentrations using small angle X-ray scattering (SAXS). This method allowed rapid screening of nanomaterial products and provided insight on how a given set of ligands dictated the rate and uniformity of passivation and thus the core size and polydispersity. Average nanoparticle diameters for gold nanoparticles functionalized with ligands derived from ligand precursor 102 and ligands obtained from ligand precursor 144 are shown in FIG. 28. The core size diameter rose from 2.6-5.9 nm as the feed % of ligand precursor 144 rose from 10 to 100%. Ligands obtained from ligand precursor 144 provide water solubility to the AuNPs despite the hydrophobic contribution of the linker; however, it was evident even upon purification and removal of free ligands, that only modest solubility of the nanoparticles in water was reached, particularly with higher feed ratios of ligand precursor 144. The combination of poor size control across a range of mixed ligand ratios, the difficulty of incorporating large amounts of malonamide, and the poor stability during manipulation when using an alkyl tether with an EG diluent ligand prompted redesign of the malonamide ligand for further ligand shell architecture optimization.

Increasing Compatibility Between Malonamide and Diluent Ligands for Control Over Mixed Ligand Ratios on the NP Surface.

In some embodiments, increasing the hydrophilicity of the malonamide linker to enhance the compatibility of the malonamide with the diluent EG ligand was evaluated. Without being limited to a single theory of operation, it is currently believed that installation of an EG linker on the malonamide would not only aid in construction of the nanoparticles during direct synthesis with regards to core size and final composition but also increase the steric stabilization and solubility in water. Short EG-linker functionalities with well-defined thicknesses could also be used to position the malonamide head group relative to the diluent ligand for assessment of sensing capabilities with differing local malonamide environments. The synthesis of a malonamide Bunte salt precursor with a triethylene glycol tether (ligand precursor 122) was performed in an attempt to provide the maximum compatibility with diluent ligand precursor 102 and subsequently position the malonamide head group just beyond the diluent ligand.

To assess the effects of malonamide ligand redesign, direct microfluidic syntheses of gold nanoparticles functionalized with ligands derived from ligand precursor 102 and ligands obtained from ligand precursor 122 were performed as described for those using ligand precursor 144. SAXS analyses of AuNPs with feed ratios of ligand precursor 122 ranging from 10%-100% indicated monomodal distributions of particles. The core size diameter varied only from 2.6-3.3 nm over the range of feed ratios with excellent reproducibility (low standard deviation) and polydispersity values ranging from 19-26% in all syntheses (FIG. 29A). $^1$H-NMR analysis of the $I_2$ decomposed nanoparticles revealed a remarkable direct correlation between the feed ratios of the input ligands to the actual composition on the nanoparticles (FIG. 29B). These data indicate that the kinetics of the Bunte salt passivation with the Au surface, given an identical linker, are similar regardless of the terminal headgroup present. Matching the linker of the functional malonamide to the diluent ligand precursor 102 proved essential for assembly of mixed ligand AuNPs with readily tunable ligand ratios and greatly increased their stability. All particles including ligands obtained from ligand precursor 122 were easily concentrated, lyophilized to dryness, and readily redispersed as necessary.

Mixed Malonamide/Ethylene Glycol AuNPs for Reversible Assembly Induced by Trivalent Lanthanide Ions.

A combination of favorable physical properties including increased steric stabilization and enhanced water solubility of gold nanoparticles functionalized with ligands derived from precursor 102 and ligands obtained from ligand precursor 122, and easily tunable malonamide surface concentrations prompted investigation of a potentially reversible NP assembly process. In some embodiments, the sensing event for trivalent lanthanides was irreversible and the nanoparticles would undergo irreversible aggregation when in close proximity due to the poor steric stabilization afforded by the heptyl linked malonamide. This binding induced NP aggregation event was the original basis for sensing but affected the upper limit of sensing (only 500 nM). Any further attempt to broaden the dynamic range of the sensor or reverse the interaction was not possible.

Initially, the assembly response of gold nanoparticles functionalized with ligands derived from ligand precursor 102 and ligands obtained from ligand precursor 122 (23: 77)-AuNPs was probed by monitoring UV-vis absorption changes upon introduction of Eu(NO$_3$)$_3$ to the nanoparticles. Other Ln$^{3+}$ salts were assessed and produced similar binding characteristics, with some embodiments exhibiting a lack of selectivity for particular Ln(NO$_3$)$_3$. In some embodiments, the presence of Eu$^{3+}$ (20 μM, aq.) caused an immediate red-shift and increase in absorption of the SPR band indicative of NP cross-linking and successful sensing (FIG. 15, line "A"). No precipitation of particles was observed over the course of several hours and the solution maintained similar absorption characteristics indicating no further NP transformations were occurring (such as core fusion). An assessment of reversibility of the sensor was subsequently performed by introducing EDTA, a strong chelator. EDTA is known to have a strong affinity for Eu$^{3+}$ (log K=17.35)[40] and was selected to facilitate ionic transfer from the malonamide functionality to EDTA and subsequently break the cross-linked structure on the nanoparticles. After EDTA introduction (aq., 20 μM, pH=7.5 buffered with Tris), the SPR absorption band blue-shifted and decreased in intensity back to the original optical spectrum of individual non-agglomerated AuNPs (FIG. 15, dotted line "C").

Transmission electron microscopy (TEM) was used to corroborate the reversible, induced by Eu$^{3+}$, assembly shown with UV-vis. FIG. 30A shows individual gold nanoparticles functionalized with ligands derived from ligand precursor 102 and ligands obtained from ligand precursor 122 (10:90) prior to sensing. The NP solution was then exposed to 20 μM Eu$^{3+}$ and large agglomerates were shown to be present (FIG. 30B). EDTA was then added to a solution of AuNPs and Eu$^{3+}$. Imaging revealed (FIG. 30C) no clusters of nanoparticles were present across the grid surface indicating all of the cross-links between AuNPs were broken and the Eu$^{3+}$ ions were successfully sequestered with EDTA.

To avoid any ambiguity from distinguishing single particles from agglomerated AuNPs caused by deposition effects in TEM imaging, the agglomeration behavior was probed in solution by SAXS. Unlike TEM, SAXS can rapidly determine interparticle interactions if present, at higher concentrations analogous to optical measurements in solution and without the use of a tethering substrate. SAXS agglomeration measurements were conducted on a lab-scale instrument. Scattering patterns were obtained for an aqueous solution of nanoparticles having a mixed ligand system of ligands derived from ligand precursor 102 and ligands obtained from ligand precursor 122 (10:90) where reversible sensing was observed by both UV-vis and TEM. The original purified nanoparticle sample displayed a monomodal distribution with no apparent ordering in solution and was modeled as a dilute system (FIG. 31, fit represented by dotted line). The same AuNP sample in the presence of 20 µM Eu$^{3+}$ (concentration matching UV-vis measurements), displayed regular ordering of nanoparticles as evidenced by a first diffraction peak ($q_1$) at 0.17 Å$^{-1}$.

In summary, the redesigned nanoparticle with a diluted malonamide (122) ligand shell senses trivalent lanthanide ions, provides high stability to the nanoparticle, and the resulting cross-linking process initiated by Eu$^{3+}$ addition was found to be reversible. In addition, the assembly of mixed malonamide/EG AuNPs with a functional EG linker and a diluted ligand shell allows for significant improvement in the dynamic range for sensing Eu$^{3+}$. Despite the fact that the Eu$^{3+}$ binding induced aggregation and core fusion event is prevented with these materials (resulting in smaller NP networks) and that the malonamide functionality has been diluted, the lower limit for detection was still found to be 250 nM. The increase in the upper limit of sensing was determined by performing a UV-vis spectral titration. The upper limit was found to be 30 µM for Eu$^{3+}$ before all of the binding sites were saturated and no further increases in absorption were found, a 60× increase in upper limit as a result of the increased stability relative to our originally reported system with 144 (100%)-AuNPs.

Relationship Between the Degree of Malonamide Multivalency and Linker Length on AuNPs and the Eu$^{3+}$ Sensing Response.

With core size variation minimized from 0-100% malonamide 122 on gold nanoparticles having mixed ligands obtained from ligand precursors 122 and 102, stable products throughout sensing as indicated by reversible sensing of Eu$^{3+}$, and improved solubility as initial criteria, the next step was to determine if the extent of cross-linking could be tuned as a function of the malonamide concentration on the AuNP surface. With malonamide 122 and diluent ligand precursor 102, the EG linker is presumed to position the dicarbonyl binding site beyond the periphery of the diluent ligand. It was initially hypothesized that an increase in malonamide content within the ligand shell would result in increased cross-linking and a linear response in sensing.

The colorimetric response quantified by UV-vis was used to probe Eu$^{3+}$ induced assembly behavior. AuNPs with ligand shells ranging from 0.5-100% 122 (verified by $^1$H-NMR above 5%) diluted with ligand precursor 102 were first all brought to approximately the same NP concentration. The solution was then exposed to 10 µL of 4 mM Eu$^{3+}$ (final conc.=20 µM) and the change in absorbance at 550 nm was plotted as a function of % malonamide 122 (FIG. 33B, "squared" trace). An increase in absorbance at this wavelength is indicative of NP cross-linking due to plasmon-plasmon coupling of individual nanoparticles and was defined as the extent of colorimetric sensing (FIG. 33A). Three sensing regimes were found in these experiments. The first at 0.5-1% 122, a ratio expected to be an average of 0.5-1 malonamide/AuNP, where the AuNPs assemble but too few malonamide ligands are present for further agglomeration. The strongest colorimetric sensing response was found with ratios of 122 from 10-33%. Lastly, the assembly upon Eu$^{3+}$ addition was surprisingly weak or completely inhibited at >50%. SAXS measurements were performed on gold nanoparticles having mixed ligands obtained from ligand precursors 122 and 102 (74:26), and the scattering patterns show minimal change to the form factor when Eu$^{3+}$ is added and no apparent NP-NP correlation indicating that no agglomerates are formed to corroborate the lack of assembly and subsequent colorimetric response by UV-vis (FIG. 22). In all cases where colorimetric sensing occurred, the response could be reversed with the addition of EDTA. It was unexpected that at higher ratios, where larger quantities of malonamide were present, no sensing of Eu$^{3+}$ was found.

Furthermore, it was hypothesized that the intensity of the colorimetric sensing response of these nanomaterials could be improved by reducing the length of the functional malonamide. This was rationalized from the fact that plasmonic coupling increases as the distance between two particles decreases. To address these hypotheses, a Bunte salt precursor malonamide featuring a single ethylene glycol unit tether, 140, was synthesized in an analogous fashion to 122 (Scheme 5). Gold nanoparticles having mixed ligand systems derived from ligands 102 and 140 were synthesized over a range of feed ratios. Core sizes varied only slightly from 2.6-2.8 nm from feed ratios of 10-100% 140 (FIG. 34) and all particles were readily soluble and stable during further manipulation. $I_2$ decomposition and $^1$H-NMR were used to determination ligand precursor compositions and both ligands were incorporated readily similar to the feed ratio.

The sensing behavior of these nanomaterials towards Eu$^{3+}$ was probed as a function of % malonamide 140 and shown in FIG. 33B ("diamond" trace). At ratios of 1-14% of 140, the sensing response was strong and transitioned from too few malonamides (1-5%) to a peak assembly at intermediate binding density (14%). The shorter EG-tether is thought to bring the AuNPs closer together and enhance the colorimetric response relative to 122 in these cases. However, a decline in the assembly was found from 27-49%. High ratios of 140 (72-100%)-AuNPs, did not respond to Eu$^{3+}$. As more malonamides were introduced into the mixed ligand shell with a shorter ligand, the malonamide head group likely is partially buried in the ligand shell, contributing to the poorer sensing of Eu$^{3+}$ relative to 122 from 27-49% and complete attenuation at the highest surface concentrations. The attenuation of Eu$^{3+}$ colorimetric sensing as the number of malonamides increased with both malonamides 122 and 140 was unexpected.

Influence of Sterics at the Periphery of a Malonamide-Functionalized AuNP Ligand Shell on Ln$^{3+}$ Triggered Assembly.

Cross-linking of the nanoparticles requires accommodation of a malonamide functionality from adjacent nanoparticles. Acyclic malonamides, such as tetramethylmalonamide (TMMA) are known to have a preferred trans orientation of the dicarbonyls in a free state, but require a cis geometry (overcoming moderate steric strain) for binding Ln$^{3+}$. As more malonamides were loaded on the nanoparticle surface, it was hypothesized that increasing dipolar interactions of neighboring diamides would make the barrier for a single Ln$^{3+}$ to cross-link two neighboring AuNPs in a >2:1 fashion challenging to overcome.

The carbonyl signatures of nanoparticles that strongly permit reversible colorimetric sensing of Eu$^{3+}$ (140/102 (27:73)-AuNPs) and a homofunctionalized AuNP material (140 (100%)-AuNPs) where no sensing occurs were assessed. To probe the malonamide's interaction with Eu$^{3+}$ on the nanomaterials, FT-IR spectroscopy of lyophilized AuNPs was used to study energy shifts in the C=O stretch of the diamides after the lanthanide ion was introduced. It has been demonstrated using DFT calculations and experimentally that the carbonyl stretch at ~1650 cm$^{-1}$ of TMMA undergoes a red-shift upon binding Ln$^{3+}$ towards 1600 cm$^{-1}$. Lyophilized particles were pressed into a pellet with KBr and IR spectra were obtained. FIG. 16A shows the expected red-shift in the carbonyl stretch indicative of binding that aligns with the observed sensing behavior from UV-vis on diluted malonamide nanoparticles. The diamide region on homofunctionalized nanoparticles (FIG. 16B), however, shows a similar red-shift in the carbonyl stretch upon addition of Eu$^{3+}$, indicating that binding of the ligand to the lanthanide ion is still occurring. However, the steric crowding of the increased number of malonamides prohibits interparticle cross-linking and multiple coordination to the ion from neighboring nanoparticles.

To place further steric demands near the binding site of the diamide and inhibit NP-NP cross-linking through Eu$^{3+}$ when high ratios are present on a nanoparticle surface, malonamide ligand 124 with tetraethyl groups, a terminal Bunte salt functionality, and an identical EG linker as with tetramethylmalonamide ligand 122, was synthesized (Scheme 4). When coupled with ligand precursor 102 in a direct synthesis, the resulting AuNPs ranged in size from 2.5-3.6 nm as the feed ratio of 124 (FIG. 32) varied from 10-100%. $^1$H-NMR analyses again indicated that matching the EG tether structure to the diluent ligand allows incorporation of both ligands directly relating to the input feed ratio with the neutral malonamide class of ligands. UV-vis sensing experiments on purified nanoparticles show that colorimetric sensing of Eu$^{3+}$ is strong at low ratios of 124 (10%) (FIG. 33C, "circle" trace). However, with only 45% 124, no sensing was observed. This did not occur until the surface concentration of malonamide ligands reached 75% with the less sterically bulky 122. Coupled with the FT-IR analysis of the diamide binding site during Eu$^{3+}$ detection, it appears that a single malonamide ligand can still interact with a lanthanide ion regardless of surface concentration but accommodating malonamides from multiple AuNPs only occurs when the active malonamide is diluted in the ligand shell.

Example 5

In this embodiment, methods of further functionalizing gold nanoparticle embodiments were explored.

Materials:

Column chromatography was performed using 40-63 μM silia-P flash silica gel (Silicycle). Deionized water (18.2 MΩ·cm) was obtained using a Barnstead Nanopure Diamond system. Flow nanoparticle syntheses were driven using Kloehn syringe pumps (P/N 54022) and Kloehn 10 and 25 mL syringes. The flow system was created using IDEX Teflon tubing (0.75 mm ID, WO#0554152) and Teflon T-mixers. Lengths of tubing were used in assembling the reactor, to keep residence and mixing constant for all flow rates.

Nanoparticle Core Size Determination Using Small Angle X-Ray Scattering (SAXS):

Nanoparticle sizes resulting from the direct syntheses performed were determined in solution at synthesis concentrations using small angle X-ray scattering (SAXS). Briefly, NP samples were exposed to monochromated X-rays from a Long Fine Focal spot (LFF) sealed X-ray tube (Cu 1.54 Å) powered by a generator at 2 kW focused by multilayer optics, measured with a Roper CCD in a Kratky camera. The Anton Paar SAXSess, in line collimation mode, was set to average a minimum of 50 scans of 40 second exposures. The corresponding dark current and background scans were subtracted from the data before desmearing using the beam profile in Anton Paar SAXSQuant software. The size distribution of the sample was then determined by using the size distribution macro in the IRENA package. The SAXS patterns were fit using the modeling II macro and best model fits were determined using a nonlinear least squares method, assuming spherical particles (confirmed with TEM), to yield a Gaussian size volume distribution binned by core diameter. For each sample, percent polydispersity was then also determined relative to the average core size.

TEM Microoscopy of Purified Nanoparticles Comprising Mixed Ligands Obtained from Ligand Precursors 100 and 102 ("EG3-Azide/EG3 (5:95)-AuNPs") and Further Modified Functionalized Nanoparticles (e.g., "EG3-Triazole-DBCO-1/EG3 (5:95)-AuNPs"):

TEM analysis of purified nanoparticle samples was performed on a FEI Tecnai G2 Spirit TEM operating at 120 kV. AuNP samples were prepared for analysis by floating holey carbon TEM grids (Ted Pella) on top of a drop of diluted AuNP solution of either EG$_3$-azide/EG$_3$ (5:95)-AuNPs or EG$_3$-triazole-DBCO-1/EG$_3$ (5:95)-AuNPs for ~5 minutes. The grids were lifted from the drop and excess solution wicked away using a Kim wipe before being allowed to dry in ambient conditions prior to imaging.

NMR Spectroscopy of Purified Nanoparticle Samples for Analysis of Purity and of Decomposed Nanoparticles for Quantifying Mixed Ligand Precursor Compositions:

Approximately 7-10 mg of purified lyophilized nanoparticles was redispersed in 0.6 mL D$_2$O or a D$_2$O/DMSO-d$_6$ mixture as specified in the experimental. An initial spectrum was acquired at 600 MHz with 128 scans and a relaxation delay of 1 second to confirm that all free ligands and synthetic byproducts were removed. The absence of sharp peaks (due to free ligands) and the presence of the broad peaks characteristic of quadrupolar broadening due to the size of the AuNPs indicated that all of the ligands were bound to the surface. Characterization of the bound mixed ligands before and after coupling reactions was initiated by adding approximately 2 mg of I$_2$ directly to the NMR tube. The mixture was shaken vigorously and allowed to react in ambient conditions for ~10-15 minutes. The solid I$_2$ was then removed from the NMR tube prior to acquiring another spectrum at 600 Mhz with 512 scans. All AuNP NMR spectra showed that the ligands had been oxidized to form the corresponding disulfides. Identification of characteristic peaks attributed to the coupled product was then performed to verify successful reactions.

UV-Visible Spectroscopy of Purified 100/102 (5:95) Functionalized-AuNPs and EG3-Triazole-DBCO-1/EG3 (5:95)-AuNPs:

All measurements were performed using an HP 8453 UV-visible spectroscopy system. Absorbance of purified AuNPs solutions were measured in a quartz cuvette cleaned with aqua regia and rinsed copiously with nanopure water between all measurements.

Fluorescence Spectroscopy of Purified 100/102 (5:95) Functionalized-AuNPs and EG3-Triazole-DBCO-1/EG3 (5:95)-AuNPs to Verify the Efficacy of the Strain Promoted AAC Reaction:

Nanoparticle solutions were first diluted with nanopure water to give yield absorbance at $\lambda_{max}$ of 0.6. All fluorescence measurements were performed using the Horiba Jobin Yvon Fluoromax-4 spectrofluorometer with excitation at 525 nm and emission collected from 540-700 nm, slit widths were set to 5 nm. The quartz cuvette was cleaned with aqua regia and rinsed copiously with nanopure water in between all measurements.

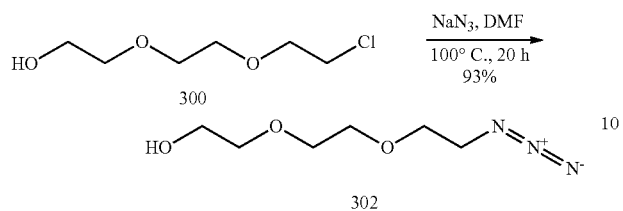

1-azido-2-(2-(2-chloroethoxyl)ethoxy)ethane (302)

Chloride 300 (4.00 g, 0.0237 mol) was dissolved in anhydrous DMF (100 mL) under $N_2$. Sodium azide (3.07 g, 0.0472 mol) was added and the mixture was heated to 100° C. for 20 hours while stirring. The mixture was cooled down to room temperature and DMF removed under reduced pressure in a rotary evaporator condensed over NaOH pellets to trap any $HN_3$ potentially produced. The crude residue was then suspended in diethyl ether (100 mL), filtered through a medium fritted funnel, and concentrated in vacuo to yield 302 (3.85 g, 93%) as a colorless liquid. $^1$H-NMR (300 MHz, $CDCl_3$): δ=3.62-3.77 (m, 10H), 3.42 (t, 2H), 2.28 (t, 1H).

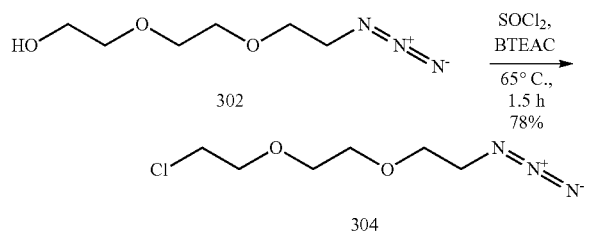

1-azido-2-(2-(2-chloroethoxyl)ethoxy)ethane (304)

A mixture of azide 302 (3.50 g, 0.0200 mol) and benzyltriethylammonium chloride (BTEAC) (0.137 g, 0.0600 mmol) were heated in a 3-neck RB flask to 65° C. Thionyl chloride (4.78 g, 0.0402 mol) was then added dropwise from an addition funnel equipped with a pressure-equalization arm, and the reaction mixture was further stirred at 65° C. for 1.5 hours while maintaining a continuous $N_2$ flow (to remove HCl generated). The mixture was let cool to room temperature and excess thionyl chloride removed by rotary evaporation. The crude product suspended in phosphate buffer (50 mM, pH=7.0, 15 mL) and extracted with 1:1 EtOAc/hexane (15 mL total). The organic layer was washed with phosphate buffer (4×15 mL), dried with $Na_2SO_4$, filtered using a coarse fritted funnel, and concentrated in vacuo to yield 304 (3.02 g, 78%) as a yellow liquid. $^1$H-NMR (300 MHz, $CDCl_3$): δ=3.64-3.81 (m, 10H), 3.42 (t, 2H).

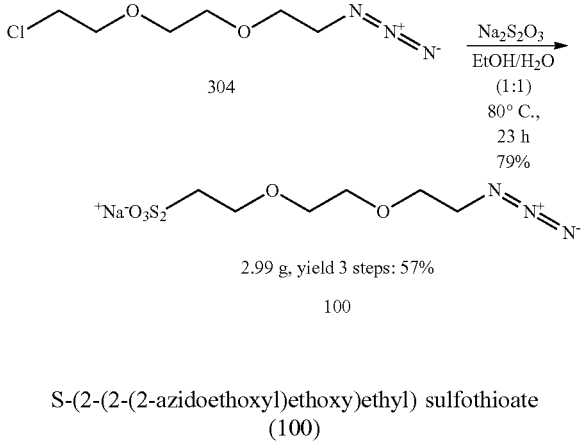

S-(2-(2-(2-azidoethoxyl)ethoxy)ethyl) sulfothioate (100)

Chloro compound 304 (2.51 g, 0.0130 mol) dissolved in a 4:3 EtOH/$H_2O$ (70 mL total). Anhydrous sodium thiosulfate (2.47 g, 0.0156 mol) (dissolved in 10 mL deionized water) was added over ~2 minutes. The resulting mixture was heated at 80° C. for 23 hours. Upon letting cool to room temperature, EtOH and $H_2O$ were removed by rotary evaporation. The crude material was dissolved in $CH_3CN$ (20 mL) to precipitate salts which were subsequently removed by filtering using a medium fritted funnel. $CH_3CN$ was removed by rotary evaporation to produce a crude yellow liquid which was then redissolved in deionized $H_2O$ (10 mL) to separate unreacted starting material as a yellow oily residue. The water solution was decanted and subsequently filtered through a fine fritted funnel to remove residual trace starting material. Concentration in vacuo produced 100 (2.99 g, 79%) as an oily pale yellow solid. $^1$H-NMR (300 MHz, D2O): δ=3.78 (t, 2H), 3.57-3.65 (m, 6H), 3.39 (t, 2H), 3.18 (t, 2H). The $^1$H-NMR of this ligand precursor is illustrated in FIG. 35. Additional characterization data is provided in FIGS. 36, 37A, 37B, and 38. FIG. 36 is a UV-vis spectrum of a gold nanoparticle before (line A) and after (line B) a coupling reaction of the gold nanoparticle with a compound comprising a clickable group capable of reacting with a clickable functional group of a gold nanoparticle ligand. FIGS. 37A and 37B are raw SAXS patters for these gold nanoparticles before (FIG. 37A) and after (FIG. 37B) coupling. FIG. 38 is a combined $^1$HNMR spectrum of a gold nanoparticle before (top spectrum) and after $I_2$ decomposition (bottom spectrum).

Calculation of Moles of Azide Ligand for a Given Mass of 100/102 (5:95) Functionalized-AuNPs:

For a 3.5 nm AuNP, there are 1580 Au atoms (obtained from $N_{Au}=10\hat{}(LOG(diameter-0.2177)-LOG(0.225/0.3639))$ and 180 $EG_3$ ligands (#$EG_3$ ligands=(surface area*$0.826_{maximum\ packing\ density\ on\ a\ sphere}$)/($0.1775\ nm^2$)$_{footprint\ of\ an\ EG3\ molecule}$. Therefore, the average molecular weight for 3.5 nm EG3-azide/EG3 (5:95)-AuNPs [$Au_{1580}$(EG3-azide)$_9$(EG$_3$)$_{171}$] is 3.41×10$^5$ g/mol. The moles of AuNPs can then be calculated from $g_{AuNPs}$*(1 mol/3.41×10$^5$ $g_{AuNPs}$). For every mole of AuNPs, there are 9 molar equivalents of azide-ligand, therefore mol$_{AuNPs}$*9=mol$_{azides}$.

EG3-triazole-DBCO-804/EG3 (5:95)-AuNPs

Lyophilized 100/102 (5:95) functionalized-AuNPs (15.59 mg, 4.1×10-7 mol 100) were dissolved in $H_2O$ (1.72 mL) in a scintillation vial. DBCO-PEG4-Alexafluor-545

(804) (1.40 mg, 1.5×10-6 mol) (dissolved in 0.28 mL H$_2$O) was added to the vial, capped, and the mixture was stirred at room temperature for 24 hours. The reaction mixture was then purified and lyophilized to isolate EG3-triazole-DBCO-804/EG3 (5:95)-AuNPs as a black powder. Confirmation of the successful coupling reaction was obtained by I$_2$ decomposition followed by NMR analysis.

EG3-triazole-DBCO-806/EG3 (5:95)-AuNPs

Lyopholized 100/102 (5:95) functionalized-AuNPs (15.04 mg, 4.0×10-7 mol 100) were dissolved in H$_2$O (1 mL) in a scintillation vial. DBCO-PEG4-OH (806) (1.53 mg, 3.0×10-6 mol) (dissolved in 1 mL t-BuOH) was added to the vial, capped, and the mixture was stirred at room temperature for 24 hours. The reaction mixture was then purified and lyophilized to isolate EG3-triazole-DBCO-806/EG3 (5:95)-AuNPs as a black powder. Confirmation of the successful coupling reaction was obtained by I$_2$ decomposition followed by NMR analysis, which is illustrated in FIG. 39.

EG3-triazole-DBCO-808/EG3 (5:95)-AuNPs

Lyopholized 100/102 (5:95) functionalized-AuNPs (16.70 mg, 4.4×10-7 mol 100) were dissolved in H$_2$O (1 mL) in a scintillation vial. DBCO-PEG4-NHS-ester (808) (1.16 mg, 2.9×10-6 mol) (dissolved in 1 mL DMSO) was added to the vial, capped, and the mixture was stirred at room temperature for 24 hours. The reaction mixture was then purified and lyophilized to isolate EG3-triazole-DBCO-808/EG3 (5:95)-AuNPs as a black powder. Confirmation of the successful coupling reaction was obtained by I$_2$ decomposition followed by NMR analysis, which is illustrated in FIG. 40.

EG3-triazole-902/EG3 (5:95)-AuNPs

Lyopholized 100/102 (5:95) functionalized-AuNPs (10.0 mg, 2.6×10-7 mol 100) were dissolved in H$_2$O (489 µL) in a scintillation vial. Sodium ascorbate (38 µL, 0.01 M in H$_2$O, 3.8×10-7 mol) was added to the vial, followed by tert-butyl alcohol as a co-solvent (985 µL), 1-ethynl-1-cyclohexanol (902) (15 µL, 0.1 M in tert-butyl alcohol, 1.5×10-6 mol), and CuBr (474 µL, satd., aq. 3.8×10-8 mol) The resulting solution was capped and stirred at room temperature for 48 hours. The reaction mixture was then purified and lyophilized to isolate EG3-triazole-902/EG3 (5:95)-AuNPs as a black powder. For $^1$H-NMR analysis, AuNPs were dissolved in D$_2$O/DMSO-d6 (80:20, 500 µL total) to confirm successful purification and decomposed with I$_2$, as illustrated in FIG. 41.

EG3-triazole-904/EG3 (5:95)-AuNPs

Lyopholized 100/102 (5:95) functionalized-AuNPs (14.5 mg, 3.8×10-7 mol 100) were dissolved in H$_2$O (489 µL) in a scintillation vial. Sodium ascorbate (37.5 µL, 0.01 M in H$_2$O, 3.8×10-7 mol) was added to the vial, followed by tert-butyl alcohol (985 µL), ethynylferrocene (904) (15 µL, 0.1 M in tert-butyl alcohol, 1.5×10-6 mol), and CuBr (474 µL, satd., aq. 3.8×10-8 mol). The resulting solution was capped and stirred at room temperature for 48 hours. The reaction mixture was then purified and lyophilized to isolate EG3-triazole-6/EG3 (5:95)-AuNPs as a black powder. For $^1$H-NMR analysis, AuNPs were dissolved in D$_2$O/DMSO-d6 (80:20, 500 µL total) to confirm successful purification, decomposed with I$_2$ (as illustrated in FIG. 43), then extracted into CDCl$_3$ (500 µL) and the organic phase was washed with brine (500 µL).

EG3-triazole-906/EG3 (5:95)-AuNPs

Lyopholized 100/102 (5:95) functionalized-AuNPs (14.6 mg, 3.9×10-7 mol 100) were dissolved in H$_2$O (489 µL) in a scintillation vial. Sodium ascorbate (37.5 µL, 0.01 M in H$_2$O, 3.75×10-7 mol) was added to the vial, followed by tert-butyl alcohol as a co-solvent (985 µL), phenylacetylene (906) (15 µL, 0.1 M in tert-butyl alcohol, 1.5×10-6 mol), and CuBr (474 µL, satd., aq. 3.8×10-8 mol). The resulting solution was capped and stirred at room temperature for 48 hours. The reaction mixture was then purified and lyophilized to isolate EG3-triazole-5/EG3 (5:95)-AuNPs as a black powder. For $^1$H-NMR analysis, AuNPs were dissolved in D$_2$O/DMSO-d6 (80:20, 500 µL total) to confirm successful purification and decomposed with I$_2$ (as illustrated in FIG. 42), then extracted into CD$_2$Cl$_2$ (500 µL) and the organic phase was washed with brine (500 µL).

EG3-triazole-908/EG3 (5:95)-AuNPs

Lyopholized 100/102 (5:95) functionalized-AuNPs (13.1 mg, 3.5×10-7 mol 100) were dissolved in H$_2$O (489 µL) in a scintillation vial. Sodium ascorbate (37.5 µL, 0.01 M in H$_2$O, 3.8×10-7 mol) was added to the vial, followed by tert-butyl alcohol (985 µL), 5-ethynyl-2'-deoxyuridine (908) (15 µL, 0.1 M in tert-butyl alcohol, 1.5×10-6 mol), and CuBr (474 µL, satd., aq. 3.8×10-8 mol). The resulting solution was capped and stirred at room temperature for 48 hours. The reaction mixture was then purified and lyophilized to isolate EG3-triazole-908/EG3 (5:95)-AuNPs as a black powder. For $^1$H-NMR analysis, AuNPs were dissolved in D$_2$O/DMSO-d6 (91:9, 550 µL total) to confirm successful purification and decomposed with I$_2$ (as illustrated in FIG. 44)

In this example, the gold nanoparticles had tailored reactive group densities and small (<5 nm) core diameters. Also, azide functionalized AuNPs were made and had good water solubility and biocompatibility. Water solubility and biocompatibility could be improved by including a ligand shell derived from a triethylene glycol terminated ligand. A triethylene glycol azide Bunte salt (100) was used to introduce the reactive azide group because the identical, or substantially similar tethering chain would afford comparable kinetics of incorporation into the ligand shell. It was confirmed that the azide group is not reduced during nanoparticle synthesis under these mild synthetic conditions (in water at room temperature). The direct synthesis method illustrated in FIG. 13 shows the approach to introduce a small amount of azide ligand within a PEG shell so that the particles will be water soluble and azides dilute enough for efficient coupling reactions.

Azide functionalized AuNPs with a mixed monolayer ligand shell were prepared in a single step using Bunte salt ligand precursors in a microfluidic reactor. Although the direct synthesis of AuNPs with Bunte salt precursors is compatible with traditional batch reactions, the formation of AuNPs occurs rapidly and mixing, in some embodiments, can have an effect on system dynamics in these cases. The microfluidic reactor afforded excellent reproducibility (SD of core diameter <0.1 nm) across multiple batches as well as low (<15%) polydispersity of the AuNPs produced (Tables 8 and 9). Through control of the pH of the gold precursor solution prior to reduction, it is possible to control the diameter of the AuNPs. In this example, 3.5±0.4 nm AuNPs were prepared by using a precursor solution pH of 5. AuNP samples were purified using tangential flow filtration and isolated as easily redispersible powders following lyophilization. In some embodiments, the AuNP reagent can be synthesised and purified within 2.5 h.

TABLE 8

$EG_3$-azide/$EG_3$ (5:95) - Multiple batches of AuNPs, core size determined by SAXS.

| | Diameter (nm) | Polydispersity (nm) | % Polydispersity |
|---|---|---|---|
| Batch 1 | 3.5 | 0.4 | 12% |
| Batch 2 | 3.7 | 0.3 | 9% |
| Batch 3 | 3.5 | 0.4 | 13% |
| Batch 4 | 3.4 | 0.5 | 14% |
| Batch 5 | 3.5 | 0.5 | 14% |
| Batch 6 | 3.5 | 0.5 | 13% |
| Average | 3.5 | 0.4 | 13% |
| Std Dev | 0.08 | 0.05 | |

TABLE 9

$EG_3$-azide/$EG_3$ (10:90) - AuNPs core size determined by SAXS

| | Diameter (nm) | Polydispersity (nm) | % Polydispersity |
|---|---|---|---|
| Batch 1 | 3.5 | 0.5 | 15% |
| Batch 2 | 3.5 | 0.6 | 16% |
| Batch 3 | 3.5 | 0.5 | 14% |
| Batch 4 | 3.5 | 0.5 | 15% |
| Batch 5 | 3.6 | 0.3 | 8% |
| Batch 6 | 3.5 | 0.4 | 12% |
| Batch 7 | 3.5 | 0.5 | 14% |
| Batch 8 | 3.5 | 0.5 | 14% |
| Batch 9 | 3.5 | 0.5 | 13% |
| Average | 3.5 | 0.5 | 13% |
| Std Dev | 0.04 | 0.07 | |

To verify that the composition of the AuNPs ligand shell was substantially similar to the feed ratio of ligands used, AuNPs with 10% of the 100 and 90% of the 102 diluent ligand ($EG_3$-azide/$EG_3$ (10:90)-AuNPs) were made. The composition of the AuNP ligand shell was determined by $I_2$ decomposition and subsequent NMR analysis and found to be comparable to the ratio expected from the feed ratio (FIG. 45). In some embodiments, click reactions were performed using AuNPs with 5% $EG_3$-azide and 95% $EG_3$ ($EG_3$-azide/$EG_3$ (5:95)-AuNPs).

To illustrate the reactivity of the azide functionalized AuNPs a strain promoted alkyne-azide cycloaddition (SPAAC) was first used. DBCO-$PEG_4$-Alexa545 (804) was chosen as a model reactant as the long PEG tether and terminal fluorophore provide a ready handle for the characterization of a successful click reaction. The fluorescent AuNPs ($EG_3$-triazole-DBCO-804) were obtained by reacting 15.59 mg of $EG_3$-azide/$EG_3$ (5:95)-AuNPs with 3 eq. of DBCO-$PEG_4$-Alexa545 in 2 mL of $H_2O$ for 24 hours.

The nanoparticle solution was then purified and isolated as a black powder. The removal of any unreacted DBCO-$PEG_4$-Alexa545 was verified by NMR, and TLC and fluorescence measurements showed that the coupling reaction was effective (FIG. 46A). $I_2$ decomposition and further NMR analysis also showed the presence of the coupled product. The reactant and product AuNP solutions were visualized by TEM under identical experimental conditions (FIG. 46B and FIG. 46C). In some embodiments, the behaviour of the nanoparticles as deposited is indicative of the change in surface chemistry following the coupling reaction. To avoid any ambiguity caused by deposition effects in TEM imaging, the size of the AuNPs was determined by SAXS. Unlike TEM, SAXS can rapidly determine nanoparticle size information while in solution in high statistics, probing the bulk of the material analogous to optical measurements in solution. The azide functionalized AuNPs were found to remain stable, with the average core diameter of $EG_3$-triazole-DBCO-804 (3.4±0.7 nm) the same as $EG_3$-azide/$EG_3$ (5:95)-AuNPs (3.4±0.4 nm) in contrast to other azide functionalized AuNPs.

The versatility of the AuNPs made in this example was further shown by coupling the gold nanoparticles to a variety of hydrophobic and hydrophilic moieties with alkyne functionalities (Scheme 6), including organometallic species and a modified thymidine analog using low loadings (~10 mol %) of a simple copper catalyst (CuBr) in air. Also tested were coupling partners that are of interest for electrochemistry (see, for example, Scheme 9) as well as those that could be used for biological imaging, or coupling to biomacromolecules (such as in Schemes 7 and 8). In some embodiments, even when the incoming species was hydrophobic (e.g., as is the case of the phenyl group illustrated in Scheme 9), the AuNPs remained water-soluble, making the $EG_3$-azide/$EG_3$ (5:95)-AuNP reagent of potential interest for other biomedical applications such as the delivery of hydrophobic drug molecules.

Synthesis of $EG_3$-azide/$EG_3$ (5:95)-AuNPs and $EG_3$-azide/$EG_3$ (10:90)-AuNPs Mixed monolayer protected AuNPs with a core diameter of 3.5±0.4 nm (by SAXS) were synthesized using a microfluidic reactor. In this example, aqueous solutions of each reagent were prepared in quantities to enable three successive syntheses using a single T-mixer. Accordingly, 1 mM stock solutions of $EG_3$ Bunte Salt and $EG_3$-azide Bunte Salt were prepared and used in a ratio of 27:3 or 24:6 depending on the desired AuNP monolayer composition, for a total volume of 30 mL. Then, 30 mL of 5 mM $HAuCl_4$ was prepared and 320 µL of 0.1 M NaOH was added raising the pH to 5. Finally, 505 µL of 1M NaOH was added to 60 mL of 1 mM $NaBH_4$. Reagents were mixed in Teflon T-mixers at a total flow rate of 60 mL/minute and the reaction mixture was purified using 30 volume equivalents of 18.2 MΩ water passed through a 10 kDa Pall Minimate tangential flow filtration capsule. The AuNPs were then isolated as a black powder following lyophilization before use in subsequent AAC reactions.

In view of the many possible embodiments to which the principles of the present disclosure may be applied, it should be recognized that the illustrated embodiments are only preferred examples of the disclosure and should not be taken as limiting the scope of the present disclosure. Rather, the scope of the present disclosure is defined by the following claims.

We claim:

1. A method for making a gold nanoparticle, comprising:
    adding a reducing composition comprising a reducing agent into a flow reactor;
    adding a pre-determined amount of a first ligand precursor composition comprising at least one first ligand precursor having a thiosulfate terminal functional group, a polar linker, and a reactive moiety selected from polar functional group, a clickable functional group, a detectable label, or an enzyme-reactive moiety into the flow reactor;
    adding a pre-determined amount of a second ligand precursor composition comprising at least one second ligand precursor different from the first ligand precursor and having a thiosulfate terminal functional group, a polar linker, and a clickable functional group into the flow reactor;

adding a gold nanoparticle precursor composition comprising a gold nanoparticle precursor into the flow reactor; and isolating a functionalized gold nanoparticle coupled to at least one ligand precursor of the second ligand precursor composition.

2. The method of claim 1, wherein the method further comprises adding a base to the reducing composition, the gold nanoparticle precursor composition, or a combination thereof so as to change the speciation of the gold nanoparticle precursor, change the pH of the reducing composition, or a combination thereof.

3. The method of claim 2, wherein the base is selected from NaOH, LiOH, KOH, and combinations thereof.

4. The method of claim 1, wherein the reducing composition is added to the flow reactor at a flow rate that results in turbulent mixing, chaotic flow, transition flow, or combinations thereof of the reducing composition, the first ligand precursor composition, the second ligand precursor composition, the gold nanoparticle composition, or any combination thereof.

5. The method of claim 1, wherein:
the at least one first ligand precursor has a formula

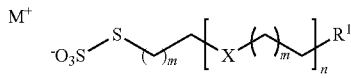

wherein each X independently is selected from oxygen or sulfur; $R^1$ is selected from —OH; —N$(R^2)_2$; —CO$_2R^2$; —P(O)(OR$^2)_3$; —PO$_4^{-3}$; —P(OR$^2)_3$; —SO$_4$; —CH(C(O)N$(R^2)_2)_2$; —N$_3$; alkynyl; a fluorophore; an enzyme; a hapten; enalapril; ramipril; losartan; or captopril, lisinopril, or an ester thereof; wherein each $R^2$ independently is selected from hydrogen, alkyl, alkenyl, alkynyl, or aryl; each m independently is 0 to 5; and n is 1 to 10;

the at least one second ligand precursor has a formula

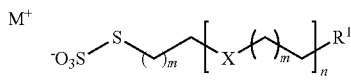

wherein each X independently is selected from oxygen or sulfur; $R^1$ is —N$_3$ or alkynyl; each m independently is 0 to 5; and n is 1 to 10; and wherein the at least one first ligand precursor is different from the at least one second ligand precursor.

6. The method of claim 1, wherein the reducing composition, the first ligand precursor composition, the second ligand precursor composition, and the gold nanoparticle precursor composition are added to a main flow channel of the flow reactor sequentially.

7. The method of claim 1, wherein the reducing composition is first added into the flow reactor followed by the first ligand precursor composition and/or the second ligand precursor composition, and the gold nanoparticle precursor composition, sequentially or simultaneously.

8. The method of claim 1, wherein the gold nanoparticle precursor composition is first added into the flow reactor followed by the first ligand precursor composition and/or the second ligand precursor composition and the reducing composition, sequentially or simultaneously.

9. The method of claim 1, wherein the gold nanoparticle precursor composition has a pH ranging from 2 to 9.

10. The method of claim 1, wherein the pH of the gold nanoparticle precursor composition is 3, 5, or 7.

11. The method of claim 1, wherein a gold nanoparticle comprises a core diameter ranging from 1.5 nm to 10 nm.

12. The method of claim 1, wherein the method comprises adding the first ligand precursor composition and the second ligand precursor composition simultaneously or sequentially, and wherein the first ligand precursor composition and the second ligand precursor composition are added at a feed ratio of first ligand precursor composition to second ligand precursor composition ranging from 80:20 to 99:1.

13. The method of claim 1, wherein the method further comprises reacting an isolated gold nanoparticle comprising a clickable functional group with a compound comprising a clickable functional group capable of reacting with the clickable functional group of the isolated gold nanoparticle.

14. The method of claim 1, wherein the method further comprises using SAXS analysis to characterize gold nanoparticles prior to isolation to determine the gold nanoparticles' core size.

15. The method of claim 1, wherein:
the reducing composition is added to a main flow channel of the flow reactor at a total flow rate of 40 mL/minute to 80 mL/minute;
the at least one first ligand precursor of the first ligand precursor composition comprises a thiosulfate terminal functional group, a polar linker, and a polar functional group;
the at least one second ligand precursor of the second ligand precursor composition comprises a thiosulfate terminal functional group, a polar linker, and a clickable functional group and wherein the first ligand precursor composition and the second ligand precursor composition are added at a feed ratio of first ligand precursor composition to second ligand precursor composition ranging from 80:20 to 99:1;
the gold nanoparticle precursor composition has a pH ranging from 2 to 9; and
the functionalized gold nanoparticle has a functionalization ratio of the at least one first ligand of the first ligand precursor composition to the at least one second ligand of the second ligand precursor composition equal to the feed ratio.

16. A combination, comprising:
a gold nanoparticle precursor composition comprising a gold nanoparticle precursor;
a first ligand precursor composition comprising a first ligand precursor having a thiosulfate terminal functional group, a polyethylene linker, and a clickable functional group; and
a second ligand precursor composition comprising a second ligand precursor having a thiosulfate terminal functional group, a polyethylene linker, and a polar functional group.

17. The combination of claim 16, further comprising a composition comprising a reducing agent.

18. The combination of claim 16, wherein the gold nanoparticle precursor has a formula HAuCl$_{4-x}$(OH)$_x$ wherein x is 0, 1, 2, 3, or 4; the second ligand precursor is a hydroxy-terminated polyethylene glycol thiosulfate ligand precursor; and the first ligand precursor is an azide-terminated polyethylene glycol thiosulfate ligand precursor.

* * * * *